(12) United States Patent
Lemieux et al.

(10) Patent No.: US 8,575,360 B2
(45) Date of Patent: Nov. 5, 2013

(54) DERIVATIVES OF 6,7-DIHYDRO-5H-IMIDAZO[1,2-A]IMIDAZOLE-3-CARBOXYLIC ACID AMIDES

(75) Inventors: Rene Marc Lemieux, Plantsville, CT (US); Steven Richard Brunette, New Milford, CT (US); Joshua Courtney Horan, Danbury, CT (US); Jennifer A. Kowalski, New Milford, CT (US); Michael David Lawlor, Seymour, CT (US); Bryan McKibben, New Milford, CT (US); Craig Andrew Miller, Mount Vernon, NY (US); Antonio J. M. Barbosa, Bonita Springs, FL (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/375,767

(22) PCT Filed: May 26, 2010

(86) PCT No.: PCT/US2010/036094
§ 371 (c)(1),
(2), (4) Date: Apr. 20, 2012

(87) PCT Pub. No.: WO2010/141273
PCT Pub. Date: Dec. 9, 2010

(65) Prior Publication Data
US 2012/0252817 A1    Oct. 4, 2012

Related U.S. Application Data

(60) Provisional application No. 61/183,098, filed on Jun. 2, 2009.

(51) Int. Cl.
*A61K 31/4188* (2006.01)
*C07D 487/04* (2006.01)
*C07D 403/12* (2006.01)
*C07D 401/12* (2006.01)
*C07D 401/14* (2006.01)

(52) U.S. Cl.
USPC .................. 548/303.1; 546/273.1; 546/113; 546/256; 546/270.4; 546/272.1; 544/238; 544/333; 548/131

(58) Field of Classification Search
USPC ...................................... 548/303.1
See application file for complete search history.

(56) References Cited

U.S. PATENT DOCUMENTS

| | | | |
|---|---|---|---|
| 3,668,217 A | 6/1972 | Fujinami et al. | |
| 3,741,981 A | 6/1973 | Fujinami et al. | |
| 3,846,441 A | 11/1974 | Mine et al. | |
| 4,911,748 A | 3/1990 | Prisbylla | |
| 4,944,791 A | 7/1990 | Schroder et al. | |
| 4,977,270 A | 12/1990 | Wee | |
| 5,208,250 A | 5/1993 | Cetenko et al. | |
| 5,306,822 A | 4/1994 | Cetenko et al. | |
| 5,334,606 A | 8/1994 | MacLeod | |
| 5,464,856 A | 11/1995 | Cetenko et al. | |
| 5,750,553 A | 5/1998 | Claussner et al. | |
| 6,063,628 A | 5/2000 | Loeb et al. | |
| 6,350,763 B1 | 2/2002 | Kelly et al. | |
| 6,353,013 B1 | 3/2002 | Kelly et al. | |
| 6,355,664 B1 | 3/2002 | Kelly et al. | |
| 6,365,615 B1 | 4/2002 | Kelly et al. | |
| 6,414,153 B1 | 7/2002 | Kelly et al. | |
| 6,492,408 B1 | 12/2002 | Wu et al. | |
| 6,689,804 B2 | 2/2004 | Wu et al. | |
| 6,844,360 B2 | 1/2005 | Kelly et al. | |
| 6,852,748 B1 | 2/2005 | Kelly et al. | |
| 7,304,067 B2 | 12/2007 | Kelly et al. | |
| 7,345,074 B2 | 3/2008 | Kelly et al. | |
| 7,462,637 B2 | 12/2008 | Kelly et al. | |
| 7,517,897 B2 | 4/2009 | Eriksson et al. | |
| 7,550,494 B2 | 6/2009 | Wu et al. | |
| 7,572,921 B2 | 8/2009 | Kim et al. | |
| 7,589,114 B2 | 9/2009 | Brunette | |
| 7,589,115 B2 | 9/2009 | Kelly et al. | |
| 2003/0008848 A1 | 1/2003 | Fleck et al. | |
| 2003/0232817 A1 | 12/2003 | Fleck et al. | |
| 2004/0006011 A1 | 1/2004 | Gour et al. | |
| 2006/0025447 A1 | 2/2006 | Wang et al. | |
| 2006/0229287 A1 | 10/2006 | Brunette | |
| 2011/0022418 A1 | 1/2011 | He et al. | |
| 2011/0224188 A1 | 9/2011 | Barbosa et al. | |
| 2012/0178734 A1 | 7/2012 | Kowalski et al. | |

FOREIGN PATENT DOCUMENTS

| | | |
|---|---|---|
| EP | 0343643 A2 | 11/1989 |
| EP | 0545478 A1 | 6/1993 |
| JP | 63270665 | 11/1988 |
| JP | 63270667 A | 11/1988 |
| JP | 04273877 A | 9/1992 |
| JP | 5188631 A | 7/1993 |

(Continued)

OTHER PUBLICATIONS

Golub et al., Science, vol. 286, Oct. 15, 1999, pp. 531-537.*
International Search Report, Form PCT/ISA/210, and Written Opinion, Form PCT/ISA/237, for corresponding PCT/US2010/036094: date of mailing: Aug. 5, 2010.
Anderson et al., Leukocyte LFA-1, p150,95 Deficiency Syndrome: Functional and Biosynthetic Studies of Three Kinds 1,2, Fed. Proc. 1985, 44, pp. 2671-2677.
Anderson et al., Targeting ICAM-1/LFA-1 interaction for controlling autoimmune diseases: designing peptide and small molecule inhibitors, Peptides, 24, pp. 487-501,2003.
Anderson et al., The Severe and Moderate Phenotypes of Heritable Mac-1, LFA-1 Deficiency: Their Quantitative Definition and Relation to Leukocyte Dysfunction and Clinical Features, J. Infect. Dis. 1985, 152, pp. 668-689.

(Continued)

*Primary Examiner* — Laura L. Stockton
(74) *Attorney, Agent, or Firm* — Michael P. Morris; Philip I. Datlow

(57) ABSTRACT

Derivatives of 6,7-dihydro-5H-imidazo[1,2-a]imidazole-3-carboxylic acid amide exhibit good inhibitory effect upon the interaction of CAMs and Leukointegrins and are thus useful in the treatment of inflammatory disease.

34 Claims, No Drawings

(56) References Cited

FOREIGN PATENT DOCUMENTS

| | | |
|---|---|---|
| WO | 9518794 A1 | 7/1995 |
| WO | 9839303 A1 | 9/1998 |
| WO | 9911258 A1 | 3/1999 |
| WO | 9949856 A2 | 10/1999 |
| WO | 2001/007440 A1 | 2/2001 |
| WO | 0130781 A2 | 5/2001 |
| WO | 2004/041827 A2 | 5/2004 |
| WO | 2004041273 A1 | 5/2004 |
| WO | 2009/070485 A1 | 6/2009 |
| WO | 2009070485 A1 | 6/2009 |

OTHER PUBLICATIONS

Becker et al., Soluble Intercellular Adhesion Molecule-1 Inhibits MHC-Restricted Specific T Cell/Tumor Interation; the Journal of Immunol. Dec. 1993, 151, pp. 7224-7232.

Beers et al., Crohn's Disease; Ulcerative Colitis; Psoriasis; Adult respiratory distress syndrome, The Merck Manual of Diagnosis and Therapy, Seventeenth Edition (online), 1999.

Boschelli, D. H., et al; "3-Alkoxybenzo[b]thiophene-2-carboxamides as Inhibitors of Neutrophil-Endothelial Cell Adhesion"; J. Med. Chem, 1994., 37, 717.

Boschelli, D. H., et al; "Inhibition of E-Selectin-, ICAM-1-, and VCAM-1-Mediated Cell Adhesion by Benzo[b] thiophene-, Benzofuran-, Indole-, and Naphthalene-2-carboxamides: Identification of PD 144795 as an Antiinflammatory Agent"; J. Med. Chem., 1995, 38, 4597-4614.

Bremner et al.. Therapy of Crohn's Disease in childhood, Expert Opinion Pharmacother. 3(7). pp. 809-825.2002.

Cosimi et al., In Vivo Effects of Monoclonal Antibody to ICAM-1 (CD54) in Nonhuman Primates With Renal Allografts 1; Journal of Immunology; 1990; vol. 144; pp. 4604-4612.

Diamond, MS., The dynamic regulation of integrin adhesiveness; Current Biology; 1994; vol. 4; No. 6; pp. 506-517.

Elgert, Autoimmunity, Immunology: Understanding the Immune System, pp. 315-330, 1996.

English translation of JP 63270665, 1988.

Gorski et al., The role of cell adhesion molecules in immunopathology; Immunology Today; 1994; vol. 15; pp. 251-255.

Halim, et al; "3-[2-(3,5-Dimethylpyrazolyl)} Succinic Anhydride: Synthone for the Synthesis of Some Heterocycles with Potential Pharmaceutical Activity"; Monatshefte fuer Chemie, 1994, 125 1437-1442.

Kavanaugh et al., UGH, et al; Treatment of Refractory Rheumatoid Arthritis with a Monoclonal Antibody to Intercellular Adhesion Molecule 1; Arthritis & Rheumatism; Jul. 1994; vol. 37; No. 7; pp. 992-1004.

Kishimoto et al; Integrins, ICAMs, and Selectins: Role and Regulation of Adhesion Molecules in Neutrophil Recruitment to Inflammatory Sites; Advances in Pharmacology; 1994; Vol. 25; pp. 117-138.

LeMAUFF et al., Effect of Anti-LFA1 (CD11a) Monoclonal Antibodies in Acute Regection inHuman Kidney Transplantation, Transplantation, Aug. 1991, 52, pp. 291-295.

Makagiansar et al., Inhibition of LFA-1/ICAM-1 and VLA-4/VCAM-1 as a Therapeutic Approach to Inflammation and Autoimmune Diseases, Medicinal Research Reviews, vol. 22, No. 2, 146-167, 2002.

Musza, L. L., et al, "Potent New Cell Adhesion Inhibitory Compounds from the Root of Trichilia rubra"; Tetrahedron, 1994, 50, 11369-11378.

Patent Abstract of Japan; Publication No. 4273877; Publication Date: Sep. 30, 1992; Applicant: Sumitomo Pharma.

Patent Abstract of Japan; Publication No. 5188631; Publication Date: Jul. 30, 1993; Applicant: Mita Industrial Co. Ltd.

Patent Abstract of Japan; Publication No. 63270665; Publication Date: Aug. 11, 1998; Applicant: Wakamoto Pharmacuet Co. Ltd.

Robinson et al., Medical Therapy of Inflammatory Bowel Disease for the 21st Century. Eur. J. Surg. Suppl 582: 90-98. 1998.

Roep et al., Soluble forms of intercellular adhesion molecule-I in insulin-dependent diabetes mellitus; The Lancet, 1994, 343, pp. 1590-1593.

Rothlein et al; Leukocyte Adhesion in Inflammation: From Discovery to the Clinic; Adhesion Molecules; Wegner, C. D., ed.; 1994; pp. 1-8.

Sanfilippo, P. J., et al; "Novel Thiazole Based Heterocycles as Inhibitors of LFA-1/ICAM-1 Mediated Cell Adhesion"; J. Med. Chem. 1995, 38, 1057-1059.

Singh et al., Immune Therapy in inflammatory bowel disease and models of colitis, British Journal of Surgery, 88, 1558-1569, 2001.

Springer, et al., Adhesion receptors of the immune system; Nature; 1990; vol. 346; pp. 425-434.

Takayama, et al; "Quantitative Structure-activity Relationships of Antifungal 1-(3,5- Dichlorophenyl)-2,5- pyrrolidinediones and 3-(3,5-Diochlorophenyl)-2,4-oxazolidinediones"; Agric. Biol. Chem. 1982, 46, 2755-8.

Tanaka et al., Potential Immunosuppressive and Antiinflammatory Activities of Malaysian Medicinal Plants Characterized by Reduced Cell Surface Expression of Cell Adhesion Molecules, Phytotherapy Research, 15, pp. 681-686 (2001).

Toyofuku et al., CA 111:7403, 1989.

Wachlin et al., IL-1beta, IFN-1gamma and TNF-alpha increase vulnerability of pancreatic beta cells to autoimmune destruction, Journal of Autoimmunity, 20, pp. 303-312, 2003.

Wu, et al; Second-Generation Lymphocyte Function-Associated Antigen-I Inhibitors: 1H-Imidazo[1,2-a] imidazol-2-one Derivatives; Journal of Medicinal Chemistry, American Chemical Society, Washington, US; vol. 47; Sep. 29, 2004; pp. 5356-5366.

* cited by examiner

DERIVATIVES OF 6,7-DIHYDRO-5H-IMIDAZO[1,2-A]IMIDAZOLE-3-CARBOXYLIC ACID AMIDES

BACKGROUND OF THE INVENTION

1. Technical Field

The present invention relates generally to a series of novel derivatives of 6,7-dihydro-5H-imidazo[1,2-a]imidazole-3-carboxylic acid amides, the synthesis of these compounds their use in the treatment of inflammatory disease and pharmaceutical compositions comprising these compounds.

2. Background Information

Research spanning the last decade has helped to elucidate the molecular events attending cell-cell interactions in the body, especially those events involved in the movement and activation of cells in the immune system (see generally, von Andrian U H, et al. *N Engl J Med* 2000; 343(14):1020-1034). Cell surface proteins, and especially the Intercellular Cellular Adhesion Molecules ("ICAMs") and "Leukointegrins", including LFA-1, MAC-1 and p150,95 (referred to in WHO nomenclature as CD18/CD11a, CD18/CD11b, and CD18/CD11c, respectively) have correspondingly been the subject of pharmaceutical research and development having as its goal the intervention in the processes of leukocyte extravasation to sites of injury and leukocyte movement to distinct targets. For example, it is presently accepted that prior to the leukocyte extravasation, which is a mandatory component of the inflammatory response, activation of integrins constitutively expressed on leukocytes occurs and is followed by a tight ligand/receptor interaction between integrins (e.g., LFA-1) and one or several distinct intercellular adhesion molecules (ICAMs) designated ICAM-1, ICAM-2 or ICAM-3 which are expressed on blood vessel endothelial cell surfaces and on other leukocytes. The interaction of the ICAMs with the Leukointegrins is a vital step in the normal functioning of the immune system. Immune processes such as antigen presentation, T-cell mediated cytotoxicity and leukocyte extravasation all require cellular adhesion mediated by ICAMs interacting with the Leukointegrins. See generally Kishimoto, T. K.; Rothlein; R. R. *Adv. Pharmacol.* 1994, 25, 117-138 and Diamond, M.; Springer, T. *Current Biology,* 1994, 4, 506-532.

A group of individuals has been identified which lack the appropriate expression of Leukointegrins, a condition termed "Leukocyte Adhesion Deficiency I" (Anderson, D. C.; et al., *Fed. Proc.* 1985, 44, 2671-2677 and Anderson, D. C.; et al., *J. Infect. Dis.* 1985, 152, 668-689). These individuals are unable to mount a normal inflammatory and/or immune response(s) due to an inability of their cells to adhere to cellular substrates. These data show that immune reactions are mitigated when lymphocytes are unable to adhere in a normal fashion due to the lack of functional adhesion molecules of the CD18 family. By virtue of the fact that LAD patients who lack CD18 cannot mount an inflammatory response, it was believed that antagonism of CD18/CD11/ICAM interactions will also inhibit an inflammatory response. The role of LFA-1 in immune cell trafficking and activation is well established and supported by studies with LFA-1 deficient mice and blocking anti-LFA-1 antibodies. In vitro, LFA-1 deficient lymphocytes are characterized by defects in aggregation and proliferation. In vivo parallel deficits in delayed type hypersensitivity (DTH) responses are observed. In animal models of organ transplantation, anti-LFA-1 antibodies have shown efficacy. Taken together these studies provide support for the role of LFA-1 in initiating and/or propagating inflammatory responses (Giblin, P. A. et al. *Curr. Pharm. Design,* 2006, 12: 2771-2795).

It has been demonstrated that the antagonism of the interaction between the ICAMs and the Leukointegrins can be realized by agents directed against either component. Specifically, blocking of the CAMs, such as for example ICAM-1, or the Leukointegrins, such as for example LFA-1, by antibodies directed against either or both of these molecules effectively inhibits inflammatory responses. In vitro models of inflammation and immune response inhibited by antibodies to ICAMs or Leukointegrins include antigen or mitogen-induced lymphocyte proliferation, homotypic aggregation of lymphocytes, T-cell mediated cytolysis and antigen-specific induced tolerance. The relevance of the in vitro studies is supported by in vivo studies with antibodies directed against ICAM-1 or LFA-1. In numerous models of transplant, including cardiac, bowel, islet and cornea, prolongation of graft survival was observed following treatment with anti-LFA-1, alone or in combination anti-ICAM-1 (see for example Nakakura E K et al., *Transplantation* 1993; 55(2):412-417). Anti-LFA-1 antibodies have also shown benefit in animal models of multiple sclerosis, lupus and inflammatory arthritis (see for example Kobayashi Y et al., *Cell Immunol* 1995; 164(2):295-305). The first LFA-1-targeted therapeutics to be tested clinically were anti-LFA-1 antibodies. Odulimomab showed efficacy in clinical trials of bone marrow transplant (Stoppa A M et al., *Transpl Int* 1991; 4(1):3-7) and in kidney transplant clinical trials (Hourmant M et al. *Transplantation* 1994; 58(3):377-380). The humanized anti-LFA-1 antibody Raptiva® (anti-CD11a, hu1124, efalizumab), marketed for psoriasis has provided the clinical proof of concept for the role of LFA-1 (Leonardi C L et al., *J Am Acad Dermatol* 2005; 52(3 Pt 1):425-433).

Thus, the prior art has demonstrated that large protein molecules which antagonize the binding of the ICAMs to the Leukointegrins have therapeutic potential in mitigating inflammatory and immunological responses often associated with the pathogenesis of many autoimmune or inflammatory diseases. However proteins have significant deficiencies as therapeutic agents, including the inability to be delivered orally and potential immunoreactivity which limits the utility of theses molecules for chronic administration. Furthermore, protein-based therapeutics are generally expensive to produce.

It follows that small molecules having the similar ability as large protein molecules to directly and selectively antagonize the binding of the ICAMs to the Leukointegrins would make preferable therapeutic agents.

Several small molecules have been described in the literature that affect the interaction of ICAMs and Leukointegrins. For example, U.S. Pat. Nos. 6,355,664 (and the corresponding WO 98/39303), 6,710,664, 6,977,267, 7,199,125 and WO 2006065908 disclose a class of small molecules, having a hydantoin core, that are inhibitors of the interaction of LFA-1 and ICAM-1. U.S. Pat. No. 6,492,408 (and corresponding WO 01/07440 A1), U.S. Pat. No. 6,844,360, U.S. Pat. No. 6,852,748, U.S. Pat. No. 7,517,897 and US Patent Application Publication 2006/0229287 all disclose compounds having this same activity that instead have a 6,7-dihydro-5H-imidazo[1,2-a]imidazole core and inhibitors with a 1H-imidazo-[1,2-a]imidazol-2-one core are disclosed by J-P Wu, et al., *J. Med Chem.* 2004; 47(22) 5356-5366. In addition, U.S. Pat. Nos. 6,673,825 and 6,974,815 and US Patent Application Publication 2006/0052434 disclose small molecules having a urazole, hexahydrobenzimidazole and pyrrolizine core respectively that are inhibitors of the interaction of LFA-1 and ICAM-1.

BRIEF SUMMARY OF THE INVENTION

The invention comprises a novel class of derivatives of 6,7-dihydro-5H-imidazo[1,2-a]imidazole-3-carboxylic acid amides and methods for making the same. These compounds are useful for the treatment of inflammatory conditions in that they exhibit good inhibitory effect upon the interaction of ICAMs and Leukointegrins. They are also expected to have an improved metabolic profile over known LFA-1 antagonists while maintaining good functional LFA-1 antagonism in a whole blood environment. Thus, the invention further comprises the use of these compounds for the treatment of inflammatory conditions and pharmaceutical compositions comprising the same as active ingredients.

DETAILED DESCRIPTION OF THE INVENTION

All terms as used herein in this specification, unless otherwise stated, shall be understood in their ordinary meaning as known in the art. For example, "$C_{1-4}$alkyl" is a saturated aliphatic hydrocarbon monovalent radical containing 1-4 carbons such as methyl, ethyl, n-propyl, 1-methylethyl (isopropyl), n-butyl or t-butyl. All alkyl groups shall be understood as being branched or unbranched, where structurally possible and unless otherwise specified. Other more specific definitions are as follows:

The term "$C_{3-6}$cycloalkyl" means a cyclic saturated hydrocarbon monovalent radical containing 3-6 carbons in the cyclic ring, such as cyclopropyl, cyclobutyl, cyclopentyl and cyclohexyl.

The terms "heterocycle" or "heterocyclyl" refers to a stable nonaromatic 4-8 membered (but preferably, 5 or 6 membered) monocyclic or nonaromatic 8-11 membered bicyclic heterocycle radical which may be either saturated or unsaturated. Each heterocycle consists of carbon atoms and one or more, preferably from 1 to 4 heteroatoms chosen from nitrogen, oxygen and sulfur. The heterocycle may be attached by any atom of the cycle, which results in the creation of a stable structure. Unless otherwise stated, heterocycles include but are not limited to, for example pyrrolidinyl, pyrrolidinonyl, pyrrolinyl, morpholinyl, thiomorpholinyl, thiomorpholinyl sulfoxide, thiomorpholinyl sulfone, dioxalanyl, piperidinyl, piperazinyl, tetrahydrofuranyl, tetrahydropyranyl, tetrahydrofuranyl, 1,3-dioxolanone, 1,3-dioxanone, 1,4-dioxanyl, piperidinonyl, tetrahydropyrimidonyl, pentamethylene sulfide, 5-oxo-4,5-dihydroisoxazol-3-yl, pentamethylene sulfoxide, pentamethylene sulfone, tetramethylene sulfide, tetramethylene sulfoxide and tetramethylene sulfone.

The term "aryl" refers to an aromatic hydrocarbon ring(s) containing from six to ten carbon ring atoms (e.g., a $C_{6-10}$ aryl). The term aryl includes monocyclic rings and bicyclic rings where at least one of the rings is aromatic. Non-limiting examples of aryls include phenyl, indanyl, indenyl, benzocyclobutanyl, dihydronaphthyl, tetrahydronaphthyl, naphthyl, benzocycloheptanyl and benzocycloheptenyl.

The term "heteroaryl" shall be understood to mean an aromatic 5-8 membered monocyclic or 8-11 membered bicyclic ring containing 1-4 heteroatoms such as N,O and S. Unless otherwise stated, such heteroaryls include thienyl, furanyl, isoxazolyl, oxazolyl, thiazolyl, thiadiazolyl, oxadiazolyl, 3-hydroxy-1H-pyrazol-5-yl, 5-oxo-4,5-dihydro-1,2,4-oxadiazol-3-yl, 5-oxo-4,5-dihydro-1,2,4-thiadiazol-3-yl, 3-hydroxyisoxazol-5-yl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl, naphthyridinyl, indazolyl, triazolyl, pyrazolo[3,4-b]pyrimidinyl, purinyl, pyrrolo[2,3-b]pyridinyl, pyrazolo[3,4-b]pyridinyl, tubercidinyl, oxazo[4,5-b]pyridinyl and imidazo[4,5-b]pyridinyl. Any nitrogen heteroatom in the heteroaryl ring can be an oxidized nitrogen atom, e.g., forming a quaternized nitrogen atom.

The term "halogen" as used in the present specification shall be understood to mean bromine, chlorine, fluorine or iodine, preferably fluorine or chlorine.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

In general, all tautomeric and isomeric forms and mixtures thereof, for example, the individual geometric isomers, stereoisomers, enantiomers, diastereomers, racemates, racemic or non-racemic mixtures of stereoisomers, mixtures of diastereomers, or mixtures of any of the foregoing, of a depicted chemical structure or compound is intended, unless the specific stereochemistry or isomeric form is specifically indicated in the compound name or structure. Any compound of this invention containing one or more asymmetric carbon atoms may occur as a racemate or racemic mixture, single enantiomer, diastereomeric mixture and individual diastereomer, or mixtures of any of the foregoing. All such isomeric forms of these compounds are expressly included in the present invention. Each stereogenic carbon may be in the R or S configuration, or a combination of configurations. Some of the compounds of formula (I) can exist in more than one tautomeric form. The invention includes methods using all such tautomers.

In further detail, the compounds of the invention and their salts include asymmetric carbon atoms and may therefore exist as single stereoisomers, racemates, and as mixtures of enantiomers and diastereomers. Typically, such compounds will be prepared as a racemic mixture. If desired, however, such compounds can be prepared or isolated as pure stereoisomers, i.e., as individual enantiomers or diastereomers, or as stereoisomer-enriched mixtures using methods well know in the art. For example, individual stereoisomers of compounds may be prepared by synthesis from optically active starting materials containing the desired chiral centers or by preparation of mixtures of enantiomeric products followed by separation or resolution, such as conversion to a mixture of diastereomers followed by separation or recrystallization, chromatographic techniques, use of chiral resolving agents, or direct separation of the enantiomers on chiral chromatographic columns Starting compounds of particular stereochemistry are either commercially available or are made by the methods described below and resolved by techniques well-known in the art.

Preparation of pure enantiomers or mixtures of desired enantiomeric excess (ee) or enantiomeric purity are accomplished by one or more of the many methods of (a) separation or resolution of enantiomers, or (b) enantioselective synthesis known to those of skill in the art, or a combination thereof. These resolution methods generally rely on chiral recognition and include, for example, chromatography using chiral stationary phases, enantioselective host-guest complexation, resolution or synthesis using chiral auxiliaries, enantioselective synthesis, enzymatic and nonenzymatic kinetic resolution, or spontaneous enantioselective crystallization. Such methods are disclosed generally in *Chiral Separation Techniques: A Practical Approach* (2nd Ed.), G. Subramanian (ed.), Wiley-VCH, 2000; T. E. Beesley and R. P. W. Scott, *Chiral Chromatography*, John Wiley & Sons, 1999; and Satinder Ahuja, *Chiral Separations by Chromatography*, Am. Chem. Soc., 2000. Furthermore, there are equally well-known methods for the quantitation of enantiomeric excess or purity, for example, GC, HPLC, CE, or NMR, and assignment of absolute configuration and conformation, for example, CD ORD, X-ray crystallography, or NMR.

The compounds of the invention are meant to embrace compounds of Formula (I) as herein described, as well as the pharmaceutically acceptable salts thereof. The term "salt" means an ionic form of the parent compound or the product of the reaction between the parent compound with a suitable acid or base to make the acid salt or base salt of the parent compound. Salts of the compounds of the present invention can be synthesized from the parent compounds which contain a basic or acidic moiety by conventional chemical methods. Generally, the salts are prepared by reacting the free base or acid parent compound with stoichiometric amounts or with an excess of the desired salt-forming inorganic or organic acid or base in a suitable solvent or various combinations of solvents.

The term "pharmaceutically acceptable salt" means a salt of a compound of the invention which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically acceptable acid addition salts and pharmaceutically acceptable base addition salts. As the compounds of the present invention are useful in both free base and salt form, in practice, the use of the salt form amounts to use of the base form. Lists of suitable salts are found in, e.g., S. M. Birge et al., J. Pharm. Sci., 1977, 66, pp. 1-19, which is hereby incorporated by reference in its entirety.

Examples of suitable acids for preparing salts include hydrochloric, hydrobromic, carbonic, sulfuric, nitric, perchloric, fumaric, maleic, phosphoric, glycolic, lactic, salicylic, succinic, toluene-p-sulfonic, tartaric, acetic, citric, methanesulfonic, formic, benzoic, malonic, naphthalene-2-sulfonic and benzenesulfonic acids. Other acids, such as oxalic acid, while not themselves pharmaceutically acceptable, may be employed in the preparation of salts useful as intermediates in obtaining the compounds of this invention and their pharmaceutically acceptable acid addition salts. Salts derived from appropriate bases include alkali metal (e.g., sodium), alkaline earth metal (e.g., magnesium), ammonium and $N-(C_{1-4}\text{ alkyl})_4^+$ salts.

In an embodiment, there is provided a compound of formula I

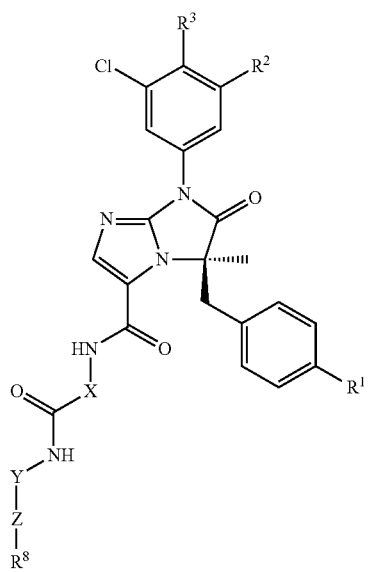

I wherein:
$R^1$ is selected from —CN, —OCF$_3$, —CF$_3$, halogen, heteroaryl optionally substituted with halogen or $C_{1-3}$ alkyl and phenyl optionally substituted with halogen.

$R^2$ is —Cl or —CF$_3$;
$R^3$ is H or halogen;
X is a group

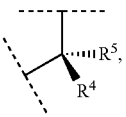

wherein
$R^4$ is selected from:
(A) —H;
(B) $C_{1-3}$ alkyl optionally substituted with one or two groups selected from:
 a) $C_{3-6}$cycloalkyl;
 b) —OR$^9$;
 c) —NR$^9$R$^{10}$;
 d) —SOR$^9$;
 e) —SO$_2$R$^9$;
 f) —C(O)NR$^9$R$^{10}$;
 g) —C(O)OR$^9$;
 h) heteroaryl, optionally substituted with $C_{1-3}$ alkyl;
 i) heterocycyl, optionally substituted with $C_{1-3}$ alkyl; and
 j) phenyl optionally substituted with $C_{1-3}$ alkyl;
(C) $C_{3-6}$cycloalkyl;
(D) heteroaryl; and
(E) phenyl, optionally substituted with halogen, —OR$^9$, —CN or —CF$_3$;
$R^5$ is H or $C_{1-3}$alkyl; or
$R^4$ and $R^5$, together with the carbon they are bonded to, form a saturated hydrocarbon ring with 3-7 carbon atoms and wherein one carbon atom in said hydrocarbon ring may be optionally replaced by —O—, —S—, —S(O)—, —SO$_2$—, —NH—, —NCH$_3$—, or —NC(O)CH$_3$—;
Y is a group

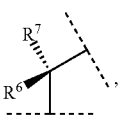

wherein
$R^6$ is H or $C_{1-3}$alkyl;
$R^7$ is H or $C_{1-3}$alkyl; or
$R^6$ and $R^7$, together with the carbon they are bonded to, form a saturated hydrocarbon ring with 3-7 carbon atoms wherein one carbon atom in said hydrocarbon ring may be optionally replaced by —O—, —S—, —S(O)—, —SO$_2$—, —NH—, —NCH$_3$—, or —NC(O)CH$_3$—;
Z is aryl or heteroaryl;
$R^8$ is selected from:
(A) aryl optionally substituted with one or two groups selected from:
 (a) $C_{1-3}$alkyl optionally substituted with —OR$^6$, —NR$^9$R$^{10}$ or —NR$^9$SO$_2$R$^{10}$;
 (b) $C_{3-7}$cycloalkyl optionally substituted with —OR$^9$ or —NR$^9$R$^{10}$;
 (a) —OR$^9$;
 (c) halogen;
 (d) —C(O)NR$^9$R$^{10}$;
 (e) —SO$_2$NR$^9$R$^{10}$;
 (f) —NR$^9$(CO)R$^{10}$;
 (g) —SO$_2$R$^9$;
 (h) —NR$^9$R$^{10}$;
 (i) —CN;
 (j) —C(O)OR$^9$;
 (k) —NR$^9$SO$_2$R$^{10}$; and
 (l) —C(O)R$^9$;

(B) heteroaryl optionally substituted with one to two groups selected from:
(a) $C_{1-3}$alkyl optionally substituted with —$OR^9$, $NR^9R^{10}$ or halogen;
(b) $C_{3-7}$cycloalkyl optionally substituted with —$OR^9$, $NR^9R^{10}$;
(a) —$OR^9$;
(c) halogen;
(d) —$C(O)NR^9R^{10}$;
(e) —$SO_2NR^9R^{10}$;
(f) —$NR^9(CO)R^{10}$;
(g) —$SO_2R^9$;
(h) —$NR^9R^{10}$; and
(i) —CN;
$R^9$ is selected from H, $C_{1-5}$alkyl or $C_{3-7}$cycloalkyl;
$R^{10}$ is selected from H, $C_{1-5}$alkyl or $C_{3-7}$cycloalkyl;
or a pharmaceutically acceptable salt thereof.

In another embodiment, is a compound of the formula I wherein:
$R^1$ is selected from —CN, —$OCF_3$, —Br, —Cl or —$CF_3$;
$R^2$ is —Cl or —$CF_3$;
$R^3$ is —F or H;
X is a group

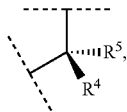

wherein
$R^4$ is selected from:
(A) $C_{1-2}$alkyl optionally substituted with —OH;
(B) (1-methyl-1H-imidazol-5-yl)methyl; and
(C) (1-methyl-1H-imidazol-4-yl)methyl;
$R^5$ is H, or —$CH_3$; or
$R^4$ and $R^5$, together with the carbon they are bonded to, form a saturated hydrocarbon ring of 3 atoms;
Y is a group

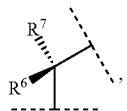

wherein
$R^6$ is H or —$CH_3$;
$R^7$ is H, or —$CH_3$; or
$R^6$ and $R^7$, together with the carbon they are bonded to, form a saturated hydrocarbon ring of 3 or 4 atoms;
Z is selected from:
(A) pyridinyl;
(B) pyrimidinyl;
(C) naphthyridinyl;
(D) pyridazinyl; and
(E) oxadiazolyl;
$R^8$ is selected from:
(A) phenyl optionally substituted with one or two groups selected from:
(a) —$OR^9$;
(b) —$CH_2OR^9$;
(c) —C(O)OH;
(d) —$C(O)NR^9R^{10}$;
(e) —$SO_2CH_3$;
(f) —$NHSO_2CH_3$;
(g) —$SO_2NR^9R^{10}$;
(h) —F;
(i) —$NHC(O)CH_3$;
(j) —$CH_2NHSO_2CH_3$;
(k) —$C(O)CH_3$;
(l) —Cl;
(m) —CN;
(n) —$CH_3$;
(o) —$CH_2N(CH_3)_2$; and
(p) 1-hydroxycyclopropyl;
(B) pyridinyl optionally mono or di substituted with —$CH_3$, —$CH_2OH$, —$NH_2$, —OH, —Cl, —F, —CN, —$CF_3$ or cyclopropyl;
(C) 1H-pyrazolyl optionally mono, di or tri substituted with —$CH_3$ or cyclopropyl;
(D) pyrimidinyl optionally substituted with —$CH_3$;
(E) isoxazolyl optionally substituted with —$CH_3$;
(F) imidazo[1,2-a]pyridinyl optionally substituted with —$CH_3$;
(G) 1H-pyrrolo[2,3-b]pyridinyl;
(H) thiazolyl optionally mono or di substituted with —$CH_3$ or —Cl;
(I) oxadiazolyl optionally substituted with cyclopropyl;
(J) furanyl;
(K) quinolinyl;
(L) 1H-imidazolyl optionally substituted with —$CH_3$;
(M) 1H-triazolyl;
(N) 1H-pyrrolyl optionally substituted with —$CH_3$;
(O) oxazolyl;
(P) 2-oxo-2H-pyridin-1-yl; and
(Q) 1H-indolyl;
$R^9$ is H or —$CH_3$;
$R^{10}$ is H or —$CH_3$;
or a pharmaceutically acceptable salt thereof.

In another embodiment is a compound of the formula I wherein:
$R^1$ is selected from —CN, —$OCF_3$, —Br, —Cl or —$CF_3$;
$R^2$ is —Cl or —$CF_3$;
$R^3$ is —F or —H;
X is a group

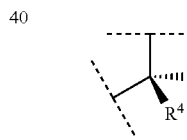

wherein
$R^4$ is selected from:
(A) —$CH_3$;
(B) —$CH_2OH$;
(C) —$CH(OH)CH_3$;
(D) (1-methyl-1H-imidazol-5-yl)methyl; and
(E) (1-methyl-1H-imidazol-4-yl)methyl;
$R^5$ is H or —$CH_3$; or
$R^4$ and $R^5$, together with the carbon they are bonded to, form a saturated hydrocarbon ring of 3 atoms;
Y is a group

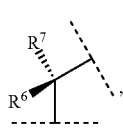

wherein
$R^6$ is —$CH_3$;
$R^7$ is H or —$CH_3$; or
$R^6$ and $R^7$, together with the carbon they are bonded to, form a saturated hydrocarbon ring of 3 or 4 atoms;

Z is selected from:

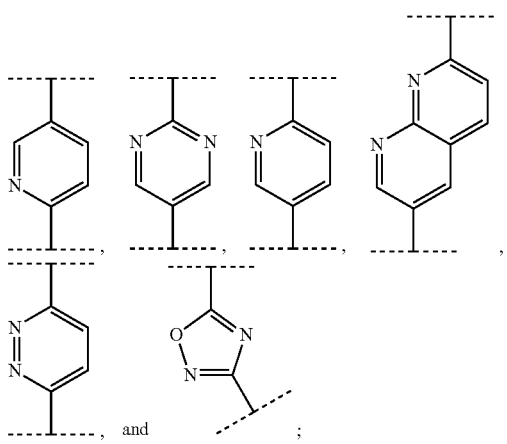
, and ;

R⁸ is selected from:
(A) phenyl substituted with one group selected from:
(a) —OH;
(b) —CH₂OR⁹;
(c) —C(O)OH;
(d) —C(O)NR⁹R¹⁰;
(e) —SO₂CH₃;
(f) —NHSO₂CH₃;
(g) —SO₂NH₂;
(h) —F;
(i) —NHC(O)CH₃;
(j) —CH₂NHSO₂CH₃; and
(k) —C(O)CH₃;
(B) pyridinyl optionally substituted with —CH₃, —CH₂OH, —NH₂, —OH, —Cl, —F; —CN or cyclopropyl;
(C) 1H-pyrazol-4-yl optionally mono, di or tri substituted with —CH₃ or cyclopropyl;
(D) pyrimidin-5-yl optionally substituted with —CH₃;
(E) isoxazol-4-yl optionally substituted with —CH₃;
(F) 2-imidazo[1,2-a]pyridin-6-yl optionally substituted with —CH₃;
(G) 1H-pyrrolo[2,3-b]pyridin-5-yl;
(H) 1H-pyrazol-3-yl;
(I) thiazol-5-yl optionally substituted with —CH₃;
(J) thiazol-4-yl;
(K) 2-cyclopropyl-1,3,4-oxadiazol-5-yl;
(L) furan-3-yl;
(M) quinolin-3-yl;
(N) 1H-imidazol-2-yl optionally substituted with —CH₃;
(O) 1-methyl-1H-imidazol-5-yl;
(P) 1H-imidazolyl; and
(Q) 1H-1,2,4-triazolyl;
R⁹ is H or —CH₃;
R¹⁰ is H or —CH₃;
or a pharmaceutically acceptable salt thereof.

In yet a further embodiment is a compound of the formula I wherein:
R¹ is selected from —CN, —OCF₃ or —Br;
R² is —Cl or —CF₃;
R³ is —F or H;
X is a group

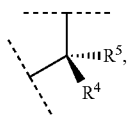

wherein
R⁴ is selected from:
(A) —CH₃;
(B) —CH₂OH; and
(C) —CH(OH)CH₃;
R⁵ is H; or
R⁴ and R⁵, together with the carbon they are bonded to, form a saturated hydrocarbon ring of 3 atoms;
Y is a group

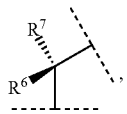

wherein
R⁶ is —CH₃;
R⁷ is H; or
R⁶ and R⁷, together with the carbon they are bonded to, form a saturated hydrocarbon ring of 3 or 4 atoms;
Z is selected from:

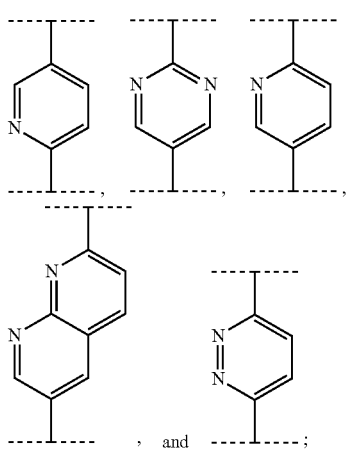
, and ;

R⁸ is selected from:
(A) phenyl substituted with one group selected from:
(a) —OH;
(b) —CH₂OH;
(c) —C(O)OH;
(d) —C(O)NR⁹R¹⁰;
(e) —SO₂CH₃;
(f) —NHSO₂CH₃; and
(g) —SO₂NH₂;
(B) pyridinyl optionally substituted with —CH₃, —CH₂OH, —NH₂, —OH, —Cl, —F;
(C) 1H-pyrazol-4-yl optionally mono, di or tri substituted with —CH₃ or cyclopropyl;
(D) 2-methyl-pyrimidin-5-yl;
(E) isoxazol-4-yl;
(F) imidazo[1,2-a]pyridin-6-yl; and
(G) 1H-pyrrolo[2,3-b]pyridin-5-yl;
R⁹ is H or —CH₃;
R¹⁰ is H or —CH₃;
or a pharmaceutically acceptable salt thereof.

In yet a further embodiment is a compound of the formula I wherein:
R¹ is selected from —CN and —OCF₃;
R² is —Cl;
R³ is —F;

X is a group

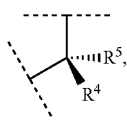

wherein

R⁴ is —CH₃ or —CH(OH)CH₃;

R⁵ is H; or

R⁴ and R⁵, together with the carbon they are bonded to, form a saturated hydrocarbon ring of 3 atoms;

Y is a group

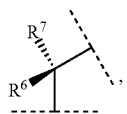

wherein

R⁶ is —CH₃;

R⁷ is H; or

R⁶ and R⁷, together with the carbon they are bonded to, form a saturated hydrocarbon ring of 3 or 4 atoms;

Z is selected from:

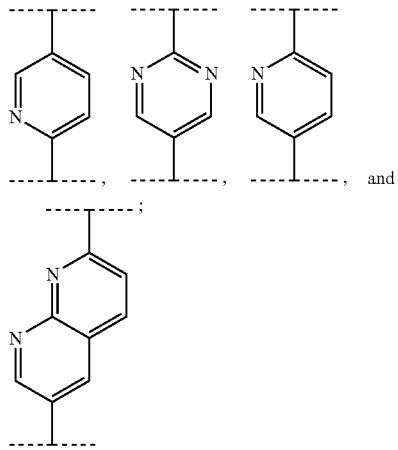

R⁸ is selected from:
(A) phenyl substituted with one group selected from:
 (a) —OH; and
 (b) —CH₂OH;
(B) pyridin-3-yl substituted in the 6-position with —CH₃ or —CH₂OH; and
(C) 1H-pyrazol-4-yl optionally mono or disubstituted with —CH₃;

or a pharmaceutically acceptable salt thereof.

The following are representative compounds of the invention which can be made by the methods described in the general synthetic schemes, the synthetic examples, and known methods in the art.

TABLE 1

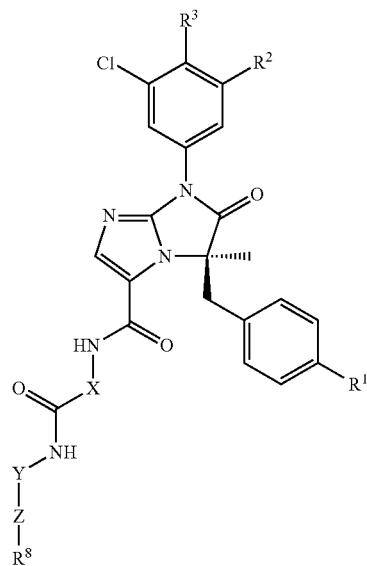

| Compound | R¹ | R² | R³ | X | Y | Z | R⁸ |
|---|---|---|---|---|---|---|---|
| 1 | CN | Cl | F | ▲ | ▲ | pyridyl | methylpyrazolyl |

TABLE 1-continued
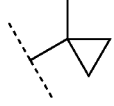
| Compound | R¹ | R² | R³ | X | Y | Z | R⁸ |
|---|---|---|---|---|---|---|---|
| 2 | CN | Cl | F | 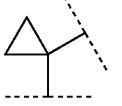 | 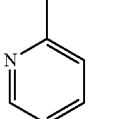 | 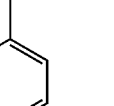 | 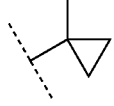 |
| 3 | CN | Cl | F | 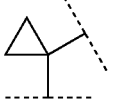 | 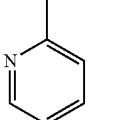 | 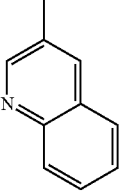 | 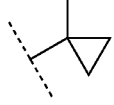 |
| 4 | OCF₃ | Cl | F | 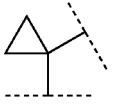 | 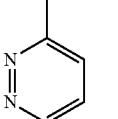 | 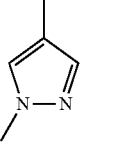 |  |
| 5 | CN | Cl | F | 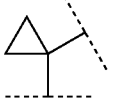 | 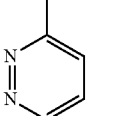 | 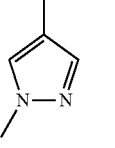 | 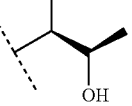 |
| 6 | CN | Cl | F | 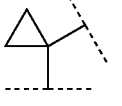 | 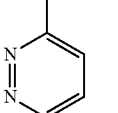 | 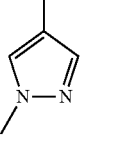 |  |

TABLE 1-continued
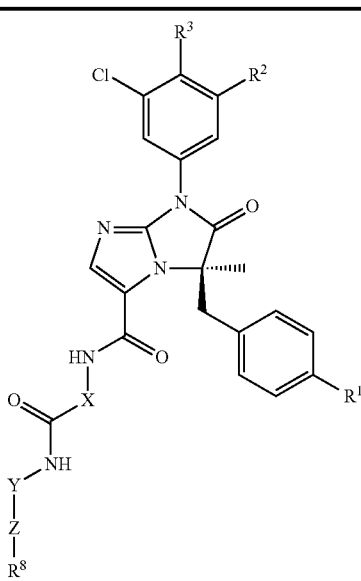
| Compound | R¹ | R² | R³ | X | Y | Z | R⁸ |
|---|---|---|---|---|---|---|---|
| 7 | OCF₃ | Cl | F | 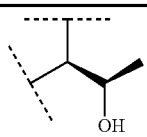 | 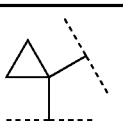 | 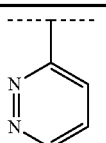 | 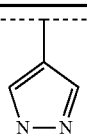 |
| 8 | OCF₃ | Cl | F | 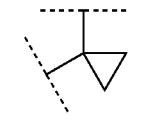 | 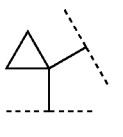 | 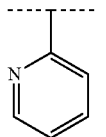 | 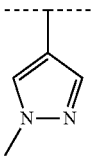 |
| 9 | CN | Cl | H | 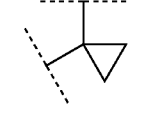 | 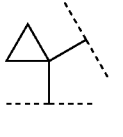 | 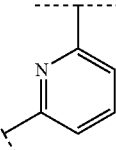 | 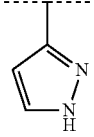 |
| 10 | CN | Cl | F |  | 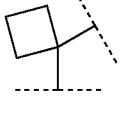 | 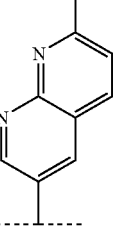 | 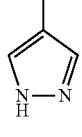 |
| 11 | CN | Cl | F | 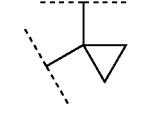 | 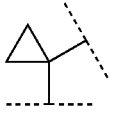 | 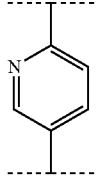 | |

TABLE 1-continued

| Compound | R¹ | R² | R³ | X | Y | Z | R⁸ |
|---|---|---|---|---|---|---|---|
| 12 | OCF₃ | Cl | F | 1,1-cyclopropyl | 1,1-cyclopropyl | pyridin-2,5-diyl | 1H-pyrazol-4-yl |
| 13 | CN | Cl | F | 1,1-cyclopropyl | 1,1-cyclopropyl | pyridin-2,5-diyl | 5-cyclopropyl-1-methyl-1H-pyrazol-4-yl |
| 14 | CN | Cl | F | 1,1-cyclopropyl | 1,1-cyclopropyl | pyridin-2,5-diyl | 3-cyclopropyl-1-methyl-1H-pyrazol-4-yl |
| 15 | CN | Cl | F | 1,1-cyclopropyl | 1,1-cyclopropyl | pyridazin-3,6-diyl | 3-cyclopropyl-1-methyl-1H-pyrazol-4-yl |
| 16 | CN | Cl | F | 1,1-cyclopropyl | 1,1-cyclopropyl | pyridin-2,5-diyl | imidazo[1,2-a]pyridin-6-yl |

TABLE 1-continued

| Compound | R¹ | R² | R³ | X | Y | Z | R⁸ |
|---|---|---|---|---|---|---|---|
| 17 | OCF₃ | Cl | F | (S)-CH₂-(1-methylimidazol-5-yl)methyl | cyclopropane-1,1-diyl | pyridine-2,5-diyl | 1-methylpyrazol-4-yl |
| 18 | CN | Cl | F | cyclopropane-1,1-diyl | cyclopropane-1,1-diyl | pyridine-2,5-diyl | 6-methylpyridin-3-yl |
| 19 | CN | Cl | F | cyclopropane-1,1-diyl | cyclopropane-1,1-diyl | pyridine-2,5-diyl | 2-methylimidazo[1,2-a]pyridin-6-yl |
| 20 | OCF₃ | Cl | F | cyclopropane-1,1-diyl | spiro[2.2]pentane-diyl | pyridine-2,5-diyl | 6-aminopyridin-3-yl |
| 21 | CN | Cl | F | cyclopropane-1,1-diyl | isopropylidene | pyridine-2,5-diyl | 1,3-dimethylpyrazol-4-yl |

TABLE 1-continued
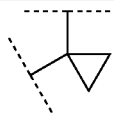
| Compound | R¹ | R² | R³ | X | Y | Z | R⁸ |
|---|---|---|---|---|---|---|---|
| 22 | CN | Cl | H | 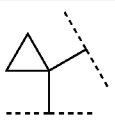 | 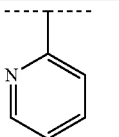 | 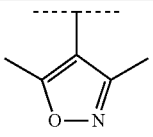 | 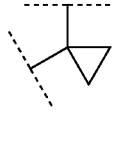 |
| 23 | CN | Cl | F | 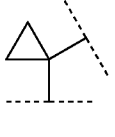 | 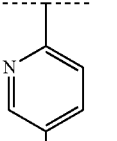 | 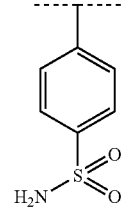 | 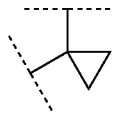 |
| 24 | OCF₃ | Cl | H | 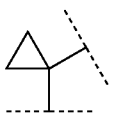 | 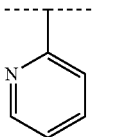 | 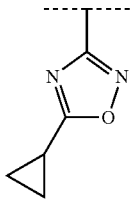 | 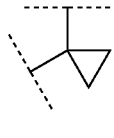 |
| 25 | CN | Cl | F | 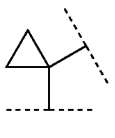 | 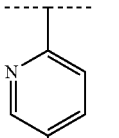 | 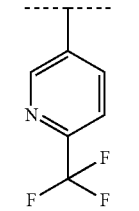 | 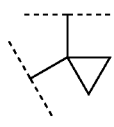 |
| 26 | CF₃ | Cl | H | 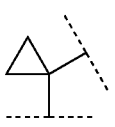 | 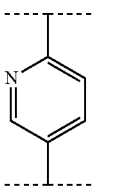 | | 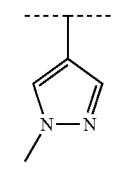 |

TABLE 1-continued
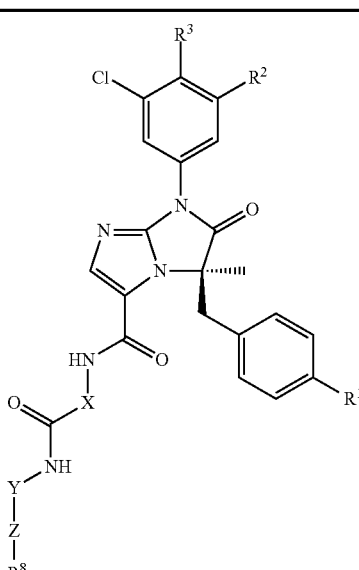
| Compound | R¹ | R² | R³ | X | Y | Z | R⁸ |
|---|---|---|---|---|---|---|---|
| 27 | CN | Cl | F | 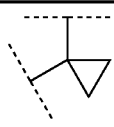 | 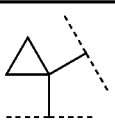 | 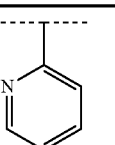 | 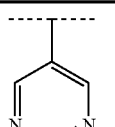 |
| 28 | OCF₃ | Cl | F | 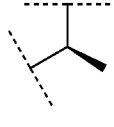 | 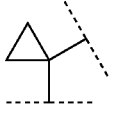 | 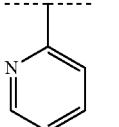 | 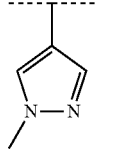 |
| 29 | CN | Cl | F | 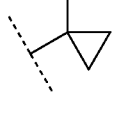 | 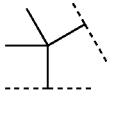 | 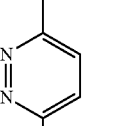 | 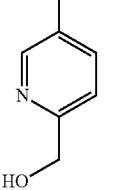 |
| 30 | CN | Cl | F | 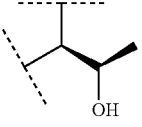 | 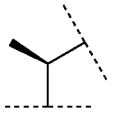 | 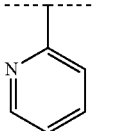 | 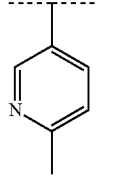 |
| 31 | CN | Cl | F | 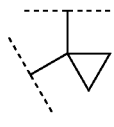 | 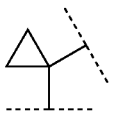 | 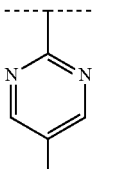 | 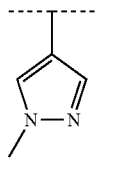 |

TABLE 1-continued

| Compound | R¹ | R² | R³ | X | Y | Z | R⁸ |
|---|---|---|---|---|---|---|---|
| 32 | CN | Cl | F | cyclopropyl | cyclopropyl | pyrimidine-2,5-diyl | 4-(hydroxymethyl)phenyl |
| 33 | CN | Cl | F | cyclopropyl | cyclopropyl | pyrimidine-2,5-diyl | 1H-pyrazol-4-yl |
| 34 | CN | Cl | F | cyclopropyl | cyclopropyl | pyrimidine-2,5-diyl | 4-hydroxyphenyl |
| 35 | CN | Cl | F | cyclopropyl | cyclopropyl | pyridazine-3,6-diyl | 1-methyl-1H-pyrazol-4-yl |
| 36 | CN | Cl | F | cyclopropyl | cyclopropyl | pyridazine-3,6-diyl | 4-fluorophenyl |

TABLE 1-continued

| Compound | R¹ | R² | R³ | X | Y | Z | R⁸ |
|---|---|---|---|---|---|---|---|
| 37 | CN | Cl | F | cyclopropyl | cyclopropyl | pyridazine-3,6-diyl | 4-(hydroxymethyl)phenyl |
| 38 | CN | Cl | F | cyclopropyl | cyclopropyl | pyridine-2,5-diyl | 1-cyclopropyl-1H-pyrazol-4-yl |
| 39 | OCF₃ | Cl | F | cyclopropyl | cyclopropyl | pyrimidine-2,5-diyl | 4-(hydroxymethyl)phenyl |
| 40 | OCF₃ | Cl | F | cyclopropyl | cyclopropyl | pyrimidine-2,5-diyl | 1-methyl-1H-pyrazol-4-yl |

TABLE 1-continued
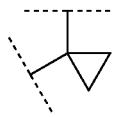
| Compound | R¹ | R² | R³ | X | Y | Z | R⁸ |
|---|---|---|---|---|---|---|---|
| 41 | OCF₃ | Cl | F | 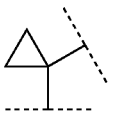 | 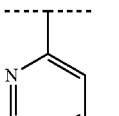 | 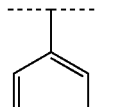 | 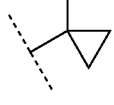 |
| 42 | OCF₃ | Cl | F | 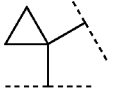 | 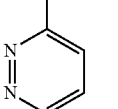 | 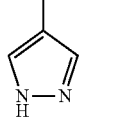 | 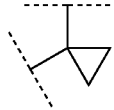 |
| 43 | CN | Cl | F | 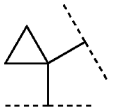 | 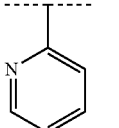 | 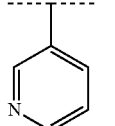 | 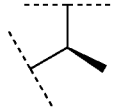 |
| 44 | CN | Cl | F | 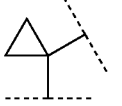 | 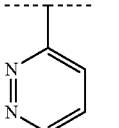 | 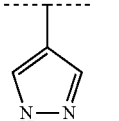 | 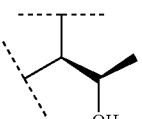 |
| 45 | CN | Cl | F |  | 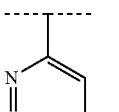 | 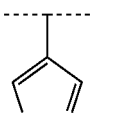 | |

TABLE 1-continued

| Compound | R¹ | R² | R³ | X | Y | Z | R⁸ |
|---|---|---|---|---|---|---|---|
| 46 | OCF₃ | Cl | F | isopropyl | cyclopropyl | pyridazine | pyrazole |
| 47 | OCF₃ | Cl | F | CH(OH)CH(CH₃) | cyclopropyl | pyridazine | pyrazole |
| 48 | OCF₃ | Cl | F | CH₂CH(1-methylimidazol-4-yl)methyl | cyclopropyl | pyridazine | pyrazole |
| 49 | OCF₃ | Cl | F | isopropyl | cyclopropyl | pyridine | pyridine-CH₂OH |
| 50 | CN | Cl | F | isopropyl | cyclopropyl | pyridine | pyridine-CH₂OH |

TABLE 1-continued
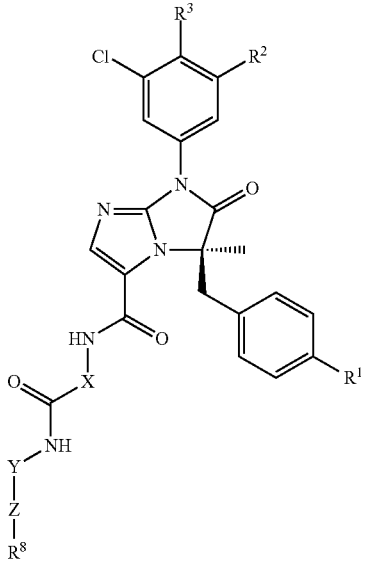
| Compound | R¹ | R² | R³ | X | Y | Z | R⁸ |
|---|---|---|---|---|---|---|---|
| 51 | CN | CF₃ | H | 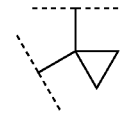 | 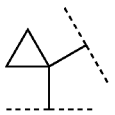 | 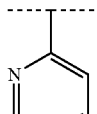 | 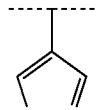 |
| 52 | CN | Cl | H | 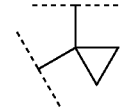 | 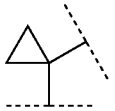 | 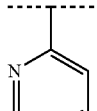 | 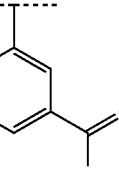 |
| 53 | CN | Cl | H | 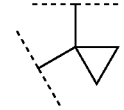 | 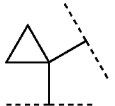 | 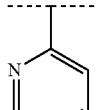 | 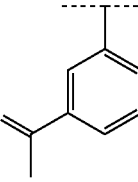 |
| 54 | CN | Cl | H | 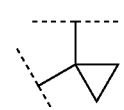 | 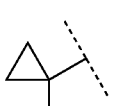 | 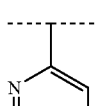 | 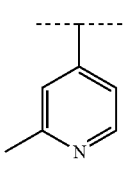 |
| 55 | CN | Cl | H | 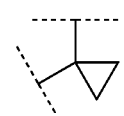 |  | 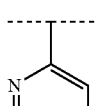 | 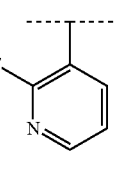 |

TABLE 1-continued

| Compound | R¹ | R² | R³ | X | Y | Z | R⁸ |
|---|---|---|---|---|---|---|---|
| 56 | CN | Cl | H | cyclopropane-1,1-diyl | cyclopropane-1,1-diyl | pyridine-2,5-diyl | 3-(N,N-dimethylcarbamoyl)phenyl |
| 57 | CN | Cl | H | cyclopropane-1,1-diyl | cyclopropane-1,1-diyl | pyridine-2,5-diyl | 4-methylpyridin-3-yl |
| 58 | CN | Cl | H | cyclopropane-1,1-diyl | cyclopropane-1,1-diyl | pyridine-2,5-diyl | 6-fluoropyridin-3-yl |
| 59 | CN | Cl | H | cyclopropane-1,1-diyl | cyclopropane-1,1-diyl | pyridine-2,5-diyl | 3-(N-methylcarbamoyl)phenyl |
| 60 | CN | Cl | H | cyclopropane-1,1-diyl | cyclopropane-1,1-diyl | pyridine-2,5-diyl | 3,5-dimethyl-1H-pyrazol-4-yl |

TABLE 1-continued
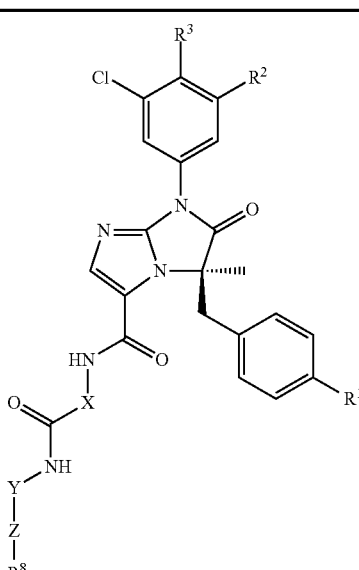
| Compound | R¹ | R² | R³ | X | Y | Z | R⁸ |
|---|---|---|---|---|---|---|---|
| 61 | CN | Cl | H | 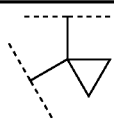 | 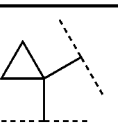 | 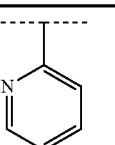 | 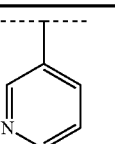 |
| 62 | CN | Cl | H | 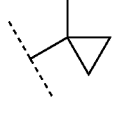 | 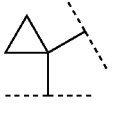 | 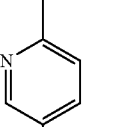 | 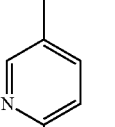 |
| 63 | CN | Cl | H | 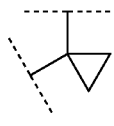 | 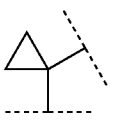 | 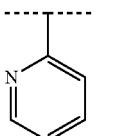 | 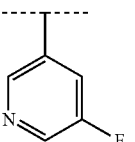 |
| 64 | CN | Cl | F | 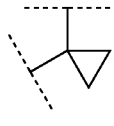 | 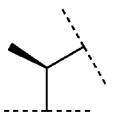 | 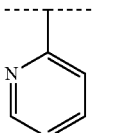 | 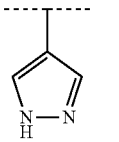 |
| 65 | CN | Cl | F | 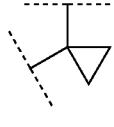 | 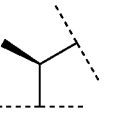 | 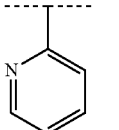 | 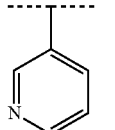 |

TABLE 1-continued

| Compound | R¹ | R² | R³ | X | Y | Z | R⁸ |
|---|---|---|---|---|---|---|---|
| 66 | CN | Cl | H | cyclopropyl | cyclopropyl | pyridyl | 3-benzamide |
| 67 | CN | Cl | H | cyclopropyl | cyclopropyl | pyridyl | 3-furyl |
| 68 | CN | Cl | F | cyclopropyl | cyclopropyl | pyridyl | 4-pyridyl |
| 69 | CN | Cl | F | cyclopropyl | cyclopropyl | pyridyl | 3-pyridyl |
| 70 | CN | Cl | F | cyclopropyl | cyclopropyl | pyridyl | 3-benzamide |

TABLE 1-continued

| Compound | R¹ | R² | R³ | X | Y | Z | R⁸ |
|---|---|---|---|---|---|---|---|
| 71 | CN | Cl | H | cyclopropane-1,1-diyl | cyclopropane-1,1-diyl | pyridine-2,5-diyl | 5-cyanopyridin-3-yl |
| 72 | CN | Cl | F | cyclopropane-1,1-diyl | cyclopropane-1,1-diyl | pyridine-2,5-diyl | 4-carbamoylphenyl |
| 73 | CN | Cl | F | cyclopropane-1,1-diyl | cyclopropane-1,1-diyl | pyridine-2,5-diyl | 6-cyclopropylpyridin-3-yl |
| 74 | CN | Cl | F | cyclopropane-1,1-diyl | cyclopropane-1,1-diyl | pyridine-2,5-diyl | 6-cyanopyridin-3-yl |

TABLE 1-continued

| Compound | R¹ | R² | R³ | X | Y | Z | R⁸ |
|---|---|---|---|---|---|---|---|
| 75 | Br | Cl | H | cyclopropyl | cyclopropyl | pyridine (2,5) | 1-methylpyrazol-4-yl |
| 76 | Cl | Cl | H | cyclopropyl | cyclopropyl | pyridine (2,5) | 1-methylpyrazol-4-yl |
| 77 | CN | Cl | F | cyclopropyl | cyclopropyl | 1,2,4-oxadiazole (3,5) | 1-methylpyrazol-4-yl |
| 78 | CN | Cl | F | CH(CH₃) | cyclopropyl | pyrimidine (2,5) | 6-(hydroxymethyl)pyridin-3-yl |
| 79 | CN | Cl | H | cyclopropyl | cyclopropyl | pyridine (2,5) | 1H-imidazol-2-yl |

TABLE 1-continued

| Compound | R¹ | R² | R³ | X | Y | Z | R⁸ |
|---|---|---|---|---|---|---|---|
| 80 | CN | Cl | H | cyclopropyl | cyclopropyl | pyridyl | 1-methyl-imidazol-2-yl |
| 81 | CN | Cl | H | cyclopropyl | cyclopropyl | pyridyl | 1H-1,2,4-triazol-1-yl |
| 82 | CN | Cl | H | cyclopropyl | cyclopropyl | pyridyl | 1H-pyrazol-1-yl |
| 83 | CN | Cl | H | cyclopropyl | cyclopropyl | pyridyl | 1H-imidazol-1-yl |
| 84 | CN | Cl | H | cyclopropyl | cyclopropyl | pyridyl | 1-methyl-imidazol-5-yl |

TABLE 1-continued
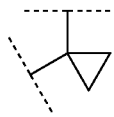
| Compound | R¹ | R² | R³ | X | Y | Z | R⁸ |
|---|---|---|---|---|---|---|---|
| 85 | CN | Cl | F | 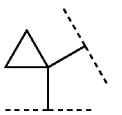 | 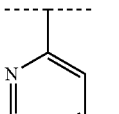 | 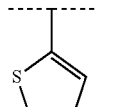 | 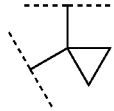 |
| 86 | OCF₃ | Cl | F | 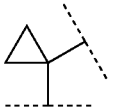 | 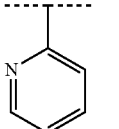 | 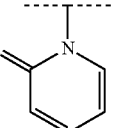 |  |
| 87 | CN | Cl | F | 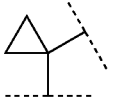 | 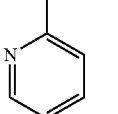 | 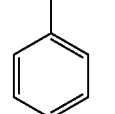 | 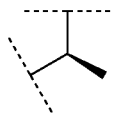 |
| 88 | CN | Cl | F | 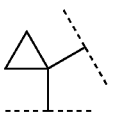 | 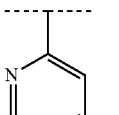 | 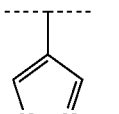 | 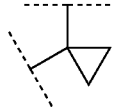 |
| 89 | OCF₃ | Cl | F | 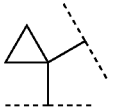 | 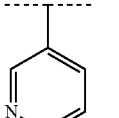 | 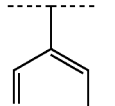 |  |

TABLE 1-continued
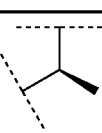
| Compound | R¹ | R² | R³ | X | Y | Z | R⁸ |
|---|---|---|---|---|---|---|---|
| 90 | CN | Cl | F |  | 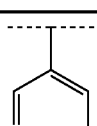 | 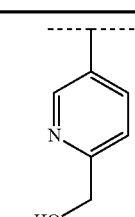 | 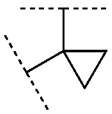 |
| 91 | CN | Cl | H |  | 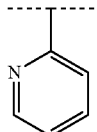 | 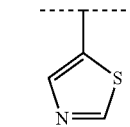 | 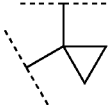 |
| 92 | CN | Cl | H | 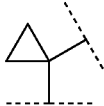 | 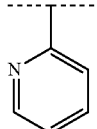 | 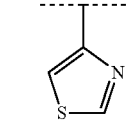 | 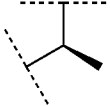 |
| 93 | CN | Cl | F | 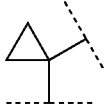 | 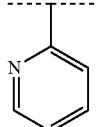 | 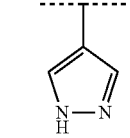 | 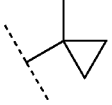 |
| 94 | CN | Cl | F | 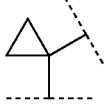 | 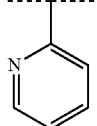 | 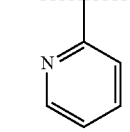 |  |

TABLE 1-continued

| Compound | R¹ | R² | R³ | X | Y | Z | R⁸ |
|---|---|---|---|---|---|---|---|
| 95 | CN | Cl | F | cyclopropyl | cyclopropyl | pyridyl | 2,4-dimethylthiazol-5-yl |
| 96 | CN | Cl | F | cyclopropyl | cyclopropyl | pyridyl | 6-(hydroxymethyl)pyridin-3-yl |
| 97 | OCF₃ | Cl | H | cyclopropyl | cyclopropyl | pyridyl | 3-cyclopropyl-1,2,4-oxadiazol-5-yl |
| 98 | CN | Cl | H | cyclopropyl | cyclopropyl | pyridyl | 5-cyclopropyl-1,3,4-oxadiazol-2-yl |
| 99 | OCF₃ | Cl | F | cyclopropyl | cyclopropyl | pyridyl | 1H-pyrazol-3-yl |

TABLE 1-continued

| Compound | R¹ | R² | R³ | X | Y | Z | R⁸ |
|---|---|---|---|---|---|---|---|
| 100 | CN | Cl | F | cyclopropyl | cyclopropyl | pyridine | 4-(hydroxymethyl)phenyl |
| 101 | CN | Cl | F | cyclopropyl | cyclopropyl | pyridine | 1,3,5-trimethylpyrazol-4-yl |
| 102 | CN | Cl | F | cyclopropyl | cyclopropyl | pyridine | 4-(1-hydroxycyclopropyl)phenyl |
| 103 | OCF₃ | Cl | H | cyclopropyl | cyclopropyl | pyridine | 6-oxo-1,6-dihydropyridin-3-yl |
| 104 | OCF₃ | Cl | F | CH(OH)CH(CH₃) | cyclopropyl | pyridine | 1-methylpyrazol-4-yl |

TABLE 1-continued

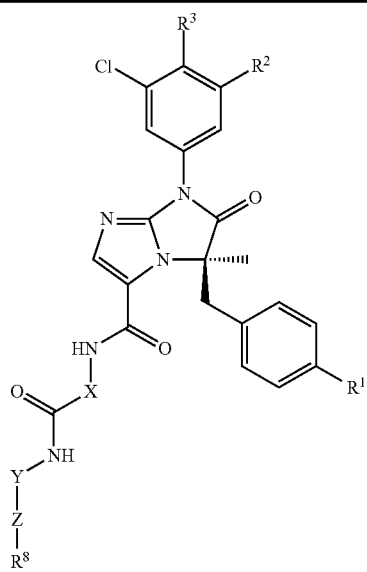

| Compound | R¹ | R² | R³ | X | Y | Z | R⁸ |
|---|---|---|---|---|---|---|---|
| 105 | CN | Cl | F | 1,1-cyclopropyl | 1,1-cyclopropyl | pyridin-2,5-diyl | 6-oxo-1,6-dihydropyridin-3-yl |
| 106 | CN | Cl | F | CH(CH₃) | 1,1-cyclopropyl | pyridazin-3,6-diyl | 4-(hydroxymethyl)phenyl |
| 107 | CN | Cl | F | CH(CH₃) | 1,1-cyclopropyl | pyridin-2,5-diyl | 1-methyl-1H-pyrazol-4-yl |
| 108 | OCF₃ | Cl | F | 1,1-cyclopropyl | 1,1-cyclopropyl | pyridin-2,5-diyl | 6-oxo-1,6-dihydropyridin-3-yl |
| 109 | CN | Cl | F | 1,1-cyclopropyl | 1,1-cyclopropyl | pyrimidin-2,5-diyl | 6-(hydroxymethyl)pyridin-3-yl |

TABLE 1-continued
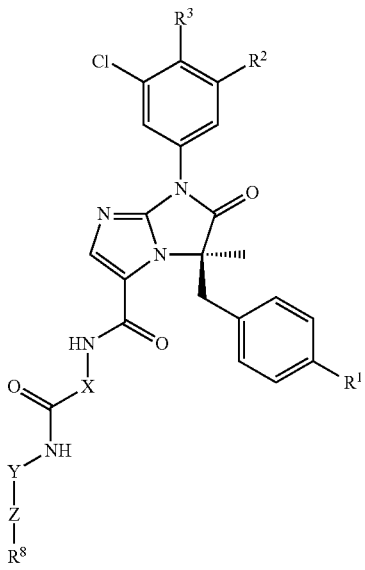
| Compound | R¹ | R² | R³ | X | Y | Z | R⁸ |
|---|---|---|---|---|---|---|---|
| 110 | OCF₃ | Cl | F | 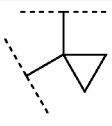 | 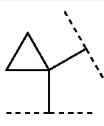 | 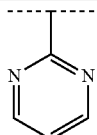 | 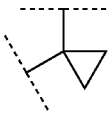 |
| 111 | CN | Cl | F | 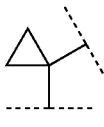 | 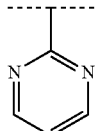 | 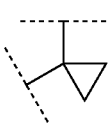 |  |
| 112 | CN | Cl | F | 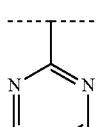 | 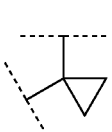 | 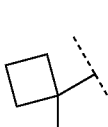 | 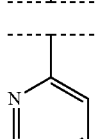 |
| 113 | CN | Cl | F |  |  | 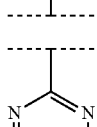 | 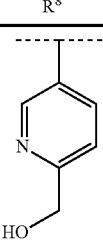 |
| 114 | CN | Cl | F | 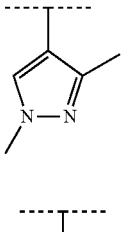 | 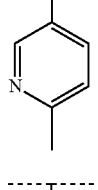 | 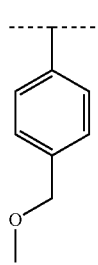 | (4-methoxymethyl-phenyl) |

TABLE 1-continued
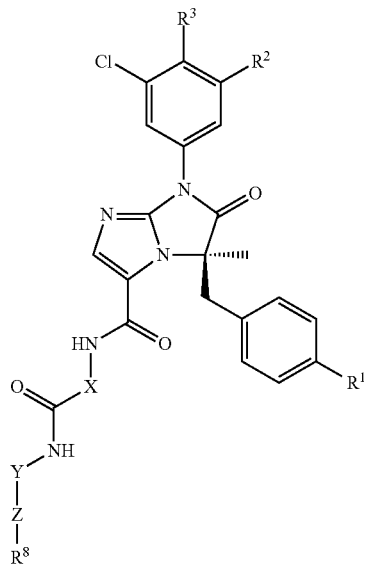
| Compound | R¹ | R² | R³ | X | Y | Z | R⁸ |
|---|---|---|---|---|---|---|---|
| 115 | CN | Cl | F | cyclopropyl | cyclopropyl | pyridyl | phenyl-SO₂NH₂ |
| 116 | OCF₃ | Cl | F | cyclopropyl | CH(CH₃) | pyridyl | pyridyl-CH₂OH |
| 117 | CN | Cl | F | CH(CH₃) | CH(CH₃) | pyridyl | pyridyl-CH₂OH |
| 118 | OCF₃ | Cl | F | CH(CH₃) | CH(CH₃) | pyridyl | pyridyl-CH₂OH |

TABLE 1-continued

| Compound | R¹ | R² | R³ | X | Y | Z | R⁸ |
|---|---|---|---|---|---|---|---|
| 119 | CN | Cl | F | CH(OH)CH(CH₃)– (stereo) | CH(CH₃)– (stereo) | pyridin-2,5-diyl | 6-(hydroxymethyl)pyridin-3-yl |
| 120 | OCF₃ | Cl | F | CH(OH)CH(CH₃)– (stereo) | CH(CH₃)– (stereo) | pyridin-2,5-diyl | 6-(hydroxymethyl)pyridin-3-yl |
| 121 | CN | Cl | F | CH(OH)CH(CH₃)– (stereo) | CH(CH₃)– (stereo) | pyridin-2,5-diyl | 1,3-dimethyl-1H-pyrazol-4-yl |
| 122 | CN | Cl | F | 1,1-cyclopropylene | CH(CH₃)– (stereo) | pyridin-2,5-diyl | 1-methyl-1H-pyrazol-4-yl |
| 123 | CN | Cl | F | 1,1-cyclopropylene | 1,1-cyclopropylene | pyridin-2,5-diyl | 1,3-dimethyl-1H-pyrazol-4-yl |

TABLE 1-continued

| Compound | R¹ | R² | R³ | X | Y | Z | R⁸ |
|---|---|---|---|---|---|---|---|
| 124 | CN | Cl | H | 1,1-cyclopropyl | 1,1-cyclopropyl | pyridin-2,4-diyl | 1H-pyrazol-4-yl |
| 125 | OCF₃ | Cl | F | CH(CH(OH)CH₃) | 1,1-cyclopropyl | pyrimidin-2,5-diyl | 6-(hydroxymethyl)pyridin-3-yl |
| 126 | CN | Cl | H | 1,1-cyclopropyl | 1,1-cyclopropyl | pyridin-2,5-diyl | 3-((dimethylamino)methyl)phenyl |
| 127 | CN | Cl | H | 1,1-cyclopropyl | 1,1-cyclopropyl | pyridin-2,5-diyl | isoxazol-4-yl |
| 128 | CN | Cl | H | 1,1-cyclopropyl | 1,1-cyclopropyl | pyridin-2,5-diyl | 1-methyl-1H-pyrrol-2-yl |

TABLE 1-continued
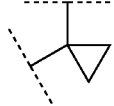
| Compound | R¹ | R² | R³ | X | Y | Z | R⁸ |
|---|---|---|---|---|---|---|---|
| 129 | CN | Cl | H | 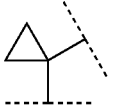 | 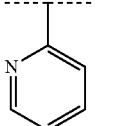 | 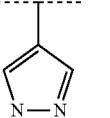 | 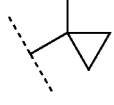 |
| 130 | CN | Cl | H | 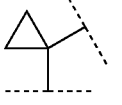 | 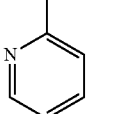 | 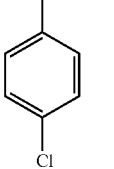 | 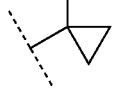 |
| 131 | CN | Cl | H | 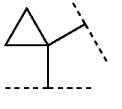 | 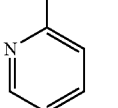 | 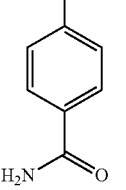 | 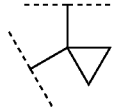 |
| 132 | CN | Cl | H | 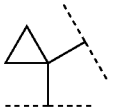 | 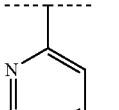 | | 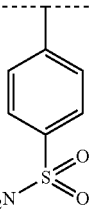 |

TABLE 1-continued

| Compound | R¹ | R² | R³ | X | Y | Z | R⁸ |
|---|---|---|---|---|---|---|---|
| 133 | CN | Cl | H | cyclopropane-1,1-diyl | cyclopropane-1,1-diyl | pyridine-2,5-diyl | 4-(methylsulfonamido)phenyl |
| 134 | CN | Cl | H | cyclopropane-1,1-diyl | cyclopropane-1,1-diyl | pyridine-2,5-diyl | 4-(methylsulfonyl)phenyl |
| 135 | CN | Cl | H | cyclopropane-1,1-diyl | cyclopropane-1,1-diyl | pyridine-2,5-diyl | 4-hydroxyphenyl |
| 136 | CN | Cl | H | cyclopropane-1,1-diyl | cyclopropane-1,1-diyl | pyridine-2,5-diyl | 4-(hydroxymethyl)phenyl |

TABLE 1-continued

| Compound | R¹ | R² | R³ | X | Y | Z | R⁸ |
|---|---|---|---|---|---|---|---|
| 137 | CN | Cl | H | cyclopropyl | cyclopropyl | pyridine (2,5) | 4-cyanophenyl |
| 138 | CN | Cl | H | cyclopropyl | cyclopropyl | pyridine (2,5) | 3-(sulfamoyl)phenyl |
| 139 | CN | Cl | H | cyclopropyl | cyclopropyl | pyridine (2,5) | 4-(acetamido)phenyl |
| 140 | CN | Cl | H | cyclopropyl | cyclopropyl | pyridine (2,5) | 3-(methylsulfonamido)phenyl |

TABLE 1-continued
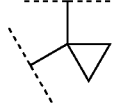
| Compound | R¹ | R² | R³ | X | Y | Z | R⁸ |
|---|---|---|---|---|---|---|---|
| 141 | CN | Cl | H | 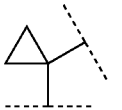 | 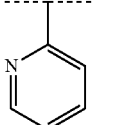 | 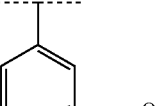 | 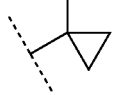 |
| 142 | CN | Cl | H | 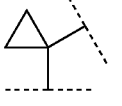 | 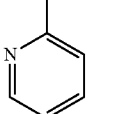 | 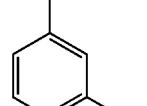 | 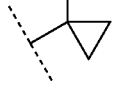 |
| 143 | CN | Cl | H | 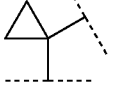 | 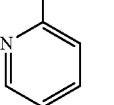 | 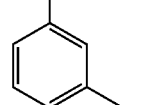 |  |
| 144 | CN | Cl | H | 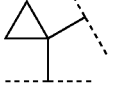 | 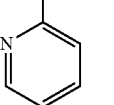 | 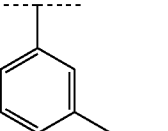 | 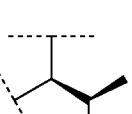 |
| 145 | CN | Cl | F |  | 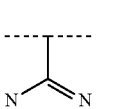 | 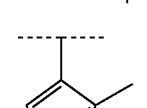 | |

TABLE 1-continued

| Compound | R¹ | R² | R³ | X | Y | Z | R⁸ |
|---|---|---|---|---|---|---|---|
| 146 | CN | Cl | H | 1,1-cyclopropyl | cyclopropyl | pyridine | 1H-pyrrolo[2,3-b]pyridin-5-yl |
| 147 | CN | Cl | H | 1,1-cyclopropyl | cyclopropyl | pyridine | 1H-indol-5-yl |
| 148 | CN | Cl | H | 1,1-cyclopropyl | cyclopropyl | pyridine | phenyl |
| 149 | CN | Cl | H | 1,1-cyclopropyl | 1,1-cyclopropyl | pyridine | 1-methyl-1H-pyrazol-4-yl |
| 150 | OCF₃ | Cl | F | 1,1-cyclopropyl | cyclopropyl | pyridine | 1,3-dimethyl-1H-pyrazol-4-yl |

TABLE 1-continued

| Compound | R¹ | R² | R³ | X | Y | Z | R⁸ |
|---|---|---|---|---|---|---|---|
| 151 | CN | Cl | F | CH(OH)CH(CH₃)– | cyclopropyl | pyridin-2,5-diyl | 3-methyl-1-methyl-1H-pyrazol-4-yl |
| 152 | CN | Cl | F | CH(OH)CH(CH₃)– | cyclopropyl | pyridin-2,5-diyl | 1-methyl-1H-pyrazol-4-yl |
| 153 | OCF₃ | Cl | F | CH(CH₂OH)– | cyclopropyl | pyridin-2,5-diyl | 1-methyl-1H-pyrazol-4-yl |
| 154 | CN | Cl | F | CH(CH₂OH)– | cyclopropyl | pyridin-2,5-diyl | 3-methyl-1-methyl-1H-pyrazol-4-yl |
| 155 | CN | Cl | F | CH(OH)CH(CH₃)– | cyclopropyl | pyridin-2,5-diyl | 3-methyl-1-methyl-1H-pyrazol-4-yl |

TABLE 1-continued

| Compound | R¹ | R² | R³ | X | Y | Z | R⁸ |
|---|---|---|---|---|---|---|---|
| 156 | CN | Cl | F | 1,1-cyclopropyl | 1,1-cyclopropyl | pyridin-2,5-diyl | 1,3-dimethyl-1H-pyrazol-4-yl |
| 157 | CN | Cl | F | 1,1-cyclopropyl | 1,1-cyclopropyl | pyridin-2,5-diyl | 3,5-dimethyl-1H-pyrazol-4-yl |
| 158 | CN | Cl | F | 1,1-cyclopropyl | 1,1-cyclopropyl | pyridin-2,5-diyl | 4-(methylsulfonyl)phenyl |
| 159 | CN | Cl | F | CH(OH)CH(CH₃) | 1,1-cyclopropyl | pyrimidin-2,5-diyl | 1-methyl-1H-pyrazol-4-yl |
| 160 | CN | Cl | F | 1,1-cyclopropyl | CH(CH₃) | pyridin-2,5-diyl | 6-(hydroxymethyl)pyridin-3-yl |

In another embodiment, the invention relates to a compound selected from compounds described in Table 1, or the pharmaceutically acceptable salts thereof.

In another embodiment, the invention relates to a compound selected from compounds 1, 2, 4-8, 10-16, 18, 20, 21, 23, 27, 28, 30-35, 37-47, 49-52, 54, 56, 58, 60-62, 64-66, 68-70, 72, 75, 78, 87-90, 93, 96, 100, 101, 103-106, 108-112, 115-121, 123, 125, 127, 129, 131-136, 138, 141-143, 145, 146 and 149-160 in Table 1, or the pharmaceutically acceptable salts thereof.

General Synthetic Methods

The compounds of the invention may be prepared by the methods described below. In the scheme below, the groups $R^1$-$R^8$, Y and Z are as defined above for general formula I unless noted otherwise. Optimum reaction conditions and reaction times may vary depending on the particular reactants used. Unless otherwise specified, solvents, temperatures, pressures and other reaction conditions may be readily selected by one of ordinary skill in the art. Specific procedures are provided in the Synthetic Examples section. Typically, reaction progress may be monitored by thin layer chromatography (TLC) or HPLC-MS if desired. Intermediates and products may be purified by chromatography on silica gel, recrystallization and/or reverse phase HPLC. HPLC purification methods used anywhere from 0-100% acetonitrile in water containing 0.1% formic acid or 0.1% TFA and used one of the following columns:

a) Waters Sunfire OBD C18 5 µm 30×150 mm column
b) Waters XBridge OBD C18 5 µm 30×150 mm column
c) Waters ODB C8 5 µm 19×150 mm column
d) Waters Atlantis ODB C18 5 µm 19×50 mm column
e) Waters Atlantis T3 OBD 5 µm 30×100 mm column
f) Phenomenex Gemini Axia C18 5 µm 30×100 mm column Starting materials and reagents are either commercially available or may be prepared by one skilled in the art using methods described in the chemical literature.

Compounds of formula I may be prepared from intermediate II as illustrated in Scheme I. The synthesis of intermediate II is reported by the following U.S. Pat. Nos. 6,492,408, 6,414,161, 6,844,360, and 6,852,748 and also U.S. Application Publications 2006/0025447 and 2007/0173517. The desired $R^1$ on formula II compounds may be obtained by selection of the appropriately substituted reagents as described in Wu et al., U.S. Pat. No. 6,492,408 and Frutos et al., U.S. Pat. No. 6,414,161.

The synthesis of compounds of formula I from intermediate II is illustrated in Scheme I.

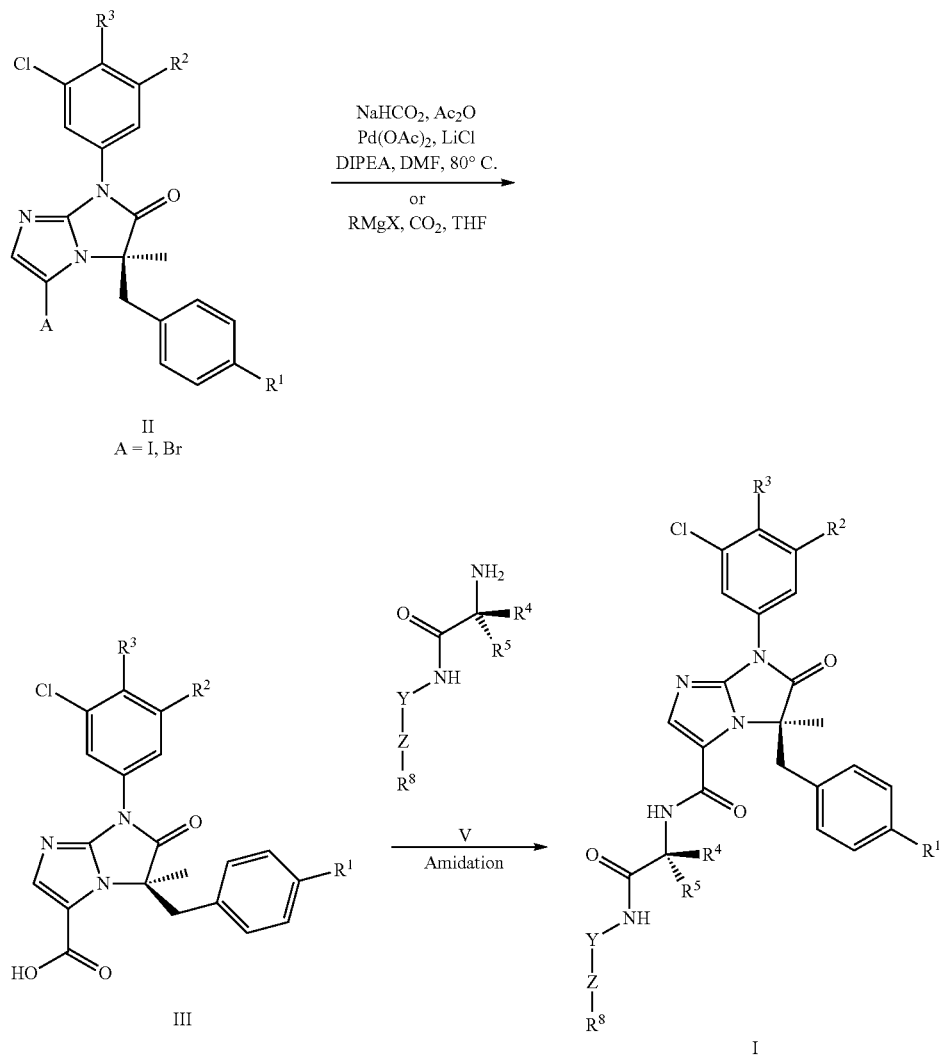

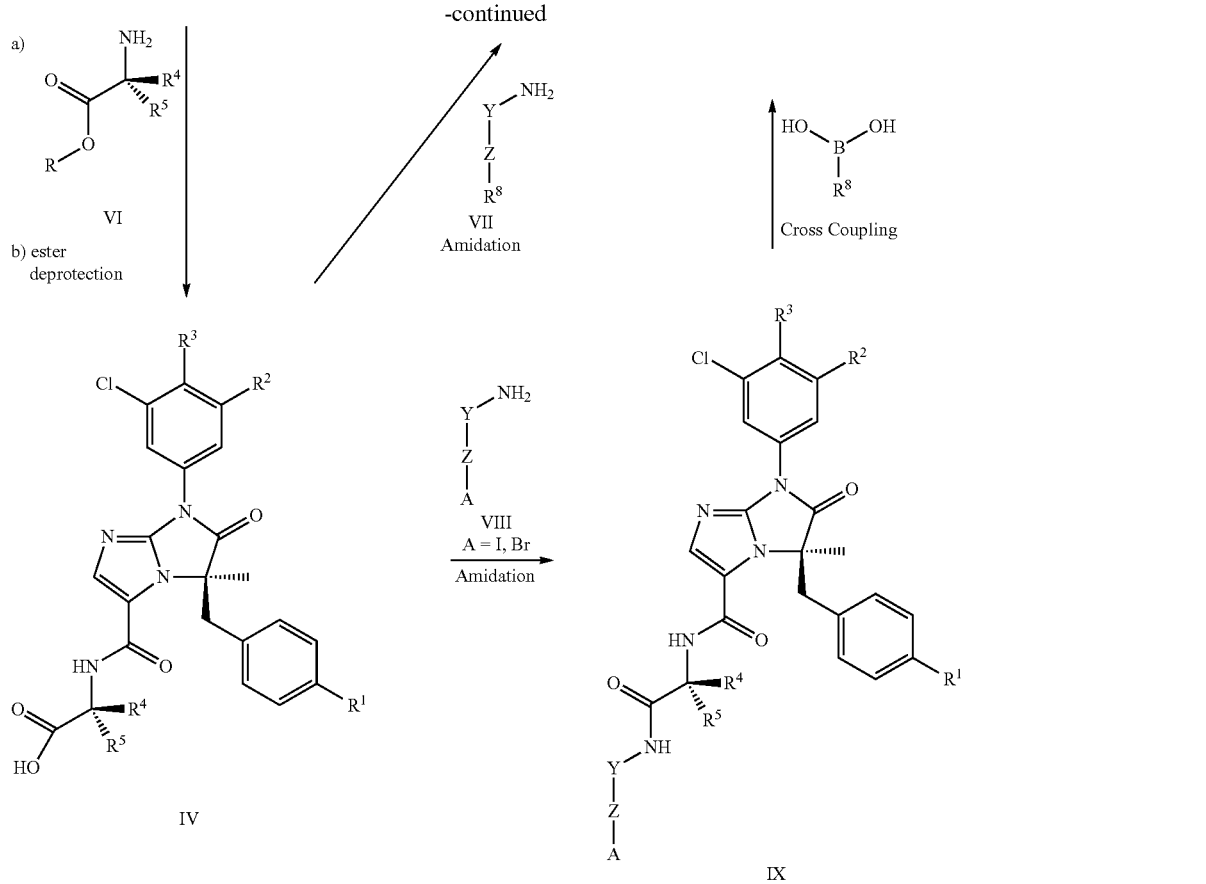

As illustrated above, II is transformed into III under Grignard conditions and trapping with $CO_2$ or Pd catalyzed carboxylation. Carboxylic acid III provides I by either amide formation with a suitably functionalized intermediate V, or a two step procedure which forms intermediate IV prior to final amide forming reaction with intermediate VII or elaboration of IV to IX by amide formation followed by cross coupling. Intermediates (V, VI, VII and VIII) are either commercially available, readily prepared from commercially available starting materials by methods known in the art or disclosed herein. The initial product of formula I may be further modified by methods known in the art to provide additional compounds of the invention. Several examples are provided in the Synthetic Examples section.

SYNTHETIC EXAMPLES

Synthesis of Intermediates

General Procedure—Synthesis of Hetetocyclic-cyclopropylamine 1-(6-Bromo-pyridin-3-yl)-cyclopropylamine bistrifluoroacetic acid salt

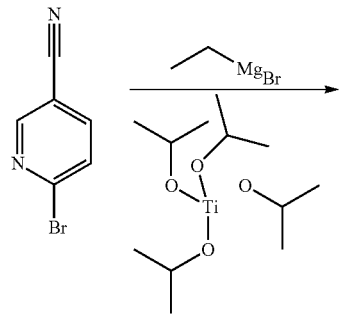

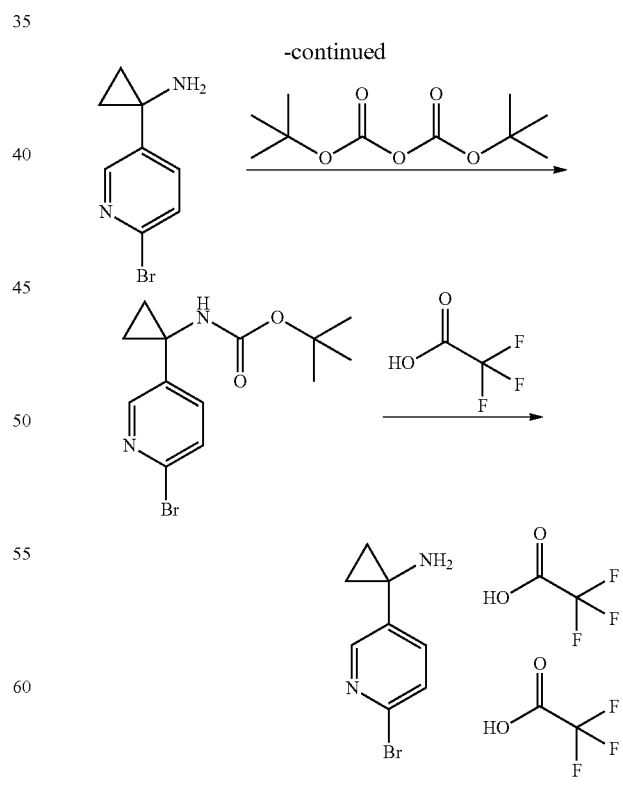

A 2 L round-bottom flask was dried under vacuum and flushed with Ar. It was then equipped with a mechanical stirrer and kept under a stream of Ar. To this flask was added anhydrous THF (750 mL) followed by Ti(Oi-Pr)₄ (72.8 mL, 246 mmol). The solution was purged under Ar and was heated to 50° C. 6-Bromo-nicotinonitrile (30 g, 164 mmol) was added to the mixture followed by dropwise addition (over 40 minutes) of 1-M ethylmagnesium bromide in THF (410 mL, 410 mmol). The reaction was allowed to stir at 50° C. After 3 h, the reaction mixture was cooled to room temperature and 3M HCl (approx 350 mL) was added. The mixture was transferred to a separatory funnel and was washed with ether (3×500 mL). The aqueous layer was allowed to stand overnight. The aqueous layer was then basified (pH 10) with 2M NaOH. The thick heterogeneous solution was diluted with EtOAc (500 mL) and the resulting solution was vigorously stirred for 5 minutes. The heterogeneous solution was allowed to stand while the layers slowly separated. The organic layer was decanted and the same extraction process was repeated (2×). The organic layers were combined, washed with brine (1×50 mL), dried over MgSO₄ and concentrated in-vacuo to yield 17 g of a dark orange-red oil. 16.1 g of crude oil was purified via normal phase flash chromatography on silica gel (340 g silica, 0-10% MeOH in CH₂Cl₂) to yield 5.94 g of 1-(6-bromo-pyridin-3-yl)-cyclopropylamine as an orange oil which slowly crystallized, m/z 213.3/215.3.

1-(6-bromo-pyridin-3-yl)-cyclopropylamine (1.16 g, 4.6 mmol) was dissolved in CH₂Cl₂ (20 mL). Et₃N (0.78 mL, 5.6 mmol) and Boc₂O (1.11 g, 5.1 mmol) were added sequentially. The reaction was stirred at room temperature. After 20 h, the reaction was diluted with CH₂Cl₂ (20 mL) and water (20 mL). The mixture was shaken and the layers separated. The aqueous layer was extracted with CH₂Cl₂ (1×100 mL). The heterogeneous CH₂Cl₂ layer was separated, washed with brine, dried over MgSO₄, filtered and concentrated to yield 1.4 g of [1-(6-bromo-pyridin-3-yl)-cyclopropyl]-carbamic acid tert-butyl ester as an orange solid.

[1-(6-bromo-pyridin-3-yl)-cyclopropyl]-carbamic acid tert-butyl ester (800 mg, 2.55 mmol) was dissolved in CH₂Cl₂ (10 mL). TFA (5 mL) was added dropwise. After 4 h, the reaction was concentrated in-vacuo to yield 1.5 g of the title compound as a brown oil, m/z 213.1/215.1.

The following compounds were prepared using procedures similar to those described above:
1-(6-Iodo-pyridin-2-yl)-cyclopropylamine bistrifluoroacetic acid salt 1-(5-Iodo-pyridin-2-yl)-cyclopropylamine bistrifluoroacetic acid salt 1-(4-Iodo-pyridin-2-yl)-cyclopropylamine bistrifluoroacetic acid salt
(1-Furan-2-yl-cyclopropyl)-carbamic acid tert-butyl ester 3-Cyclopropyl-1-methyl-4-(4,4,5,5-tetramethyl-1,3,2-dioxaborolan-2-yl)-1H-pyrazole

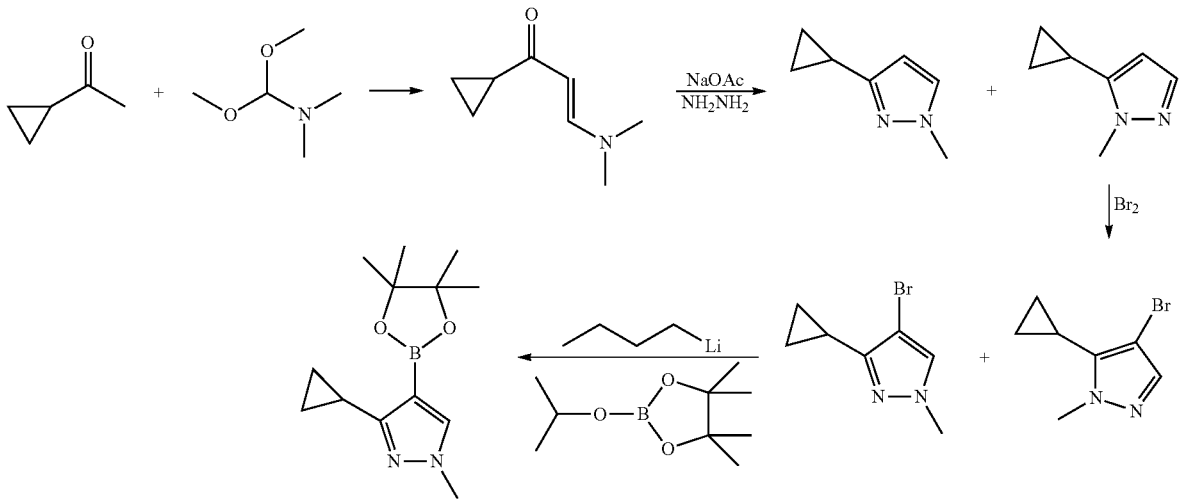

A mixture of cyclopropyl methyl ketone (7.0 mL, 70.7 mmol) and dimethoxymethyl-dimethyl-amine (18.7 mL, 141.5 mmol, 2 eq) was heated at 100° C. for 16 h. The mixture was concentrated under high vac for 1 h to give (E)-1-cyclopropyl-3-dimethylamino-propenone as a yellow oil (2.7 g, 28%) which was used for the next step without further purification.

To the mixture of (E)-1-cyclopropyl-3-dimethylamino-propenone (1.5 g, 10.8 mmol) and NaOAc (1.3 g, 16.2 mmol) in ethanol (10 mL) was added a solution of hydrazine (0.6 mL, 11.9 mmol), and the solution was kept at 70° C. overnight. The mixture was concentrated, the solid was filtered, washed with CH₂Cl₂, and the filtrate was concentrated under reduced pressure to give a mixture of 5-cyclopropyl-1-methyl-1H-pyrazole and 3-cyclopropyl-1-methyl-1H-pyrazole as a yellow solid (950 mg, 72%). The crude material was used for the next step without further purification.

To a mixture of pyrazoles (3.9 g, 31.9 mmol) in CHCl₃ (10 mL) at room temperature was added dropwise neat bromine (1.2 mL, 23.4 mmol), and the mixture was stirred for 1 h at room temperature. The reaction was poured into 2 mL of aqueous saturated NaHCO₃. The organic layer was diluted with CH₂Cl₂ (10 mL), washed with brine, dried over MgSO₄ and concentrated to give the crude product (4.2 g, 66%). The residue was purified by column chromatography (15% EtOAc/hexanes) to provide each of the pure regioisomers (860 mg, 27% and 560 mg, 18%, respectively). NOE NMR experiment unambiguously determined the regiochemistry.

To a stirred solution of 4-bromo-3-cyclopropyl-1-methyl-1H-pyrazole (500 mg, 2.5 mmol) in THF (10 mL) was added dropwise a 2.5 M solution of n-BuLi (1.4 mL, 3.5 mmol) at −78° C., and the resulting light yellow solution was stirred for 30 min. To the mixture was added a solution of 2-isopropoxy-4,4,5,5-tetramethyl-1,3,2-dioxaborolane (1.1 mL, 5.5 mmol) in THF (1 mL), and the mixture was warmed to room temperature over 30 min. The reaction was quenched with saturated aqueous NH$_4$Cl solution. The mixture was extracted with EtOAc (50 mL), washed with brine, dried over MgSO$_4$, filtered and concentrated under reduced pressure. The residue was purified by normal phase flash chromatography on silica gel (5% MeOH—CH$_2$Cl$_2$, Rf=0.35) to provide 3-cyclopropyl-1-methyl-4-(4,4,5,5-tetramethyl-1,3,2-dioxaborolan-2-yl)-1H-pyrazole (294 mg, 48%) as a yellow oil.

The following compound was prepared using procedures similar to those described above:
5-Cyclopropyl-1-methyl-4-(4,4,5,5-tetramethyl-1,3,2-dioxaborolan-2-yl)-1H-pyrazole 1-[5-(2-Methyl-imidazo[1,2-a]pyridin-6-yl)-pyridin-2-yl]-cyclopropylamine dihydrochloride (0.042 mmol) of Pd(dppf)Cl$_2$.dichloromethane complex, and 1.3 mL of 1M K$_3$PO$_4$ in water. The mixture was heated to 110° C. in the microwave for 10 min. The mixture was cooled, and the brown organic phase was separated, diluted with EtOAc, and filtered through diatomaceous earth. The filtrate was concentrated and purified by reversed phase HPLC (10-40% MeCN/water+0.1% TFA) to provide 61 mg (40% yield) of {1-[5-(2-methyl-imidazo[1,2-a]pyridin-6-yl)-pyridin-2-yl]-cyclopropyl}-carbamic acid tert-butyl ester as a pale brown powder.

{1-[5-(2-Methyl-imidazo[1,2-a]pyridin-6-yl)-pyridin-2-yl]-cyclopropyl}-carbamic acid tert-butyl ester (21 mg, 0.06 mmol) was dissolved in 0.5 mL of CH$_2$Cl$_2$ and 1 mL of 4M HCl in dioxane was added. The resulting suspension was stirred for 1 h. The mixture was concentrated to yield crude 1-[5-(2-methyl-imidazo[1,2-a]pyridin-6-yl)-pyridin-2-yl]-cyclopropylamine dihydrochloride. The material was used in subsequent reactions without purification.

(R)-5-(4-Cyano-benzyl)-7-(3,5-dichloro-4-fluoro-phenyl)-5-methyl-6-oxo-6,7-dihydro-5H-imidazo[1,2-a]imidazole-3-carboxylic acid{1-[(R)-1-(6-bromo-pyridin-3-yl)-ethylcarbamoyl]-cyclopropyl}-amide

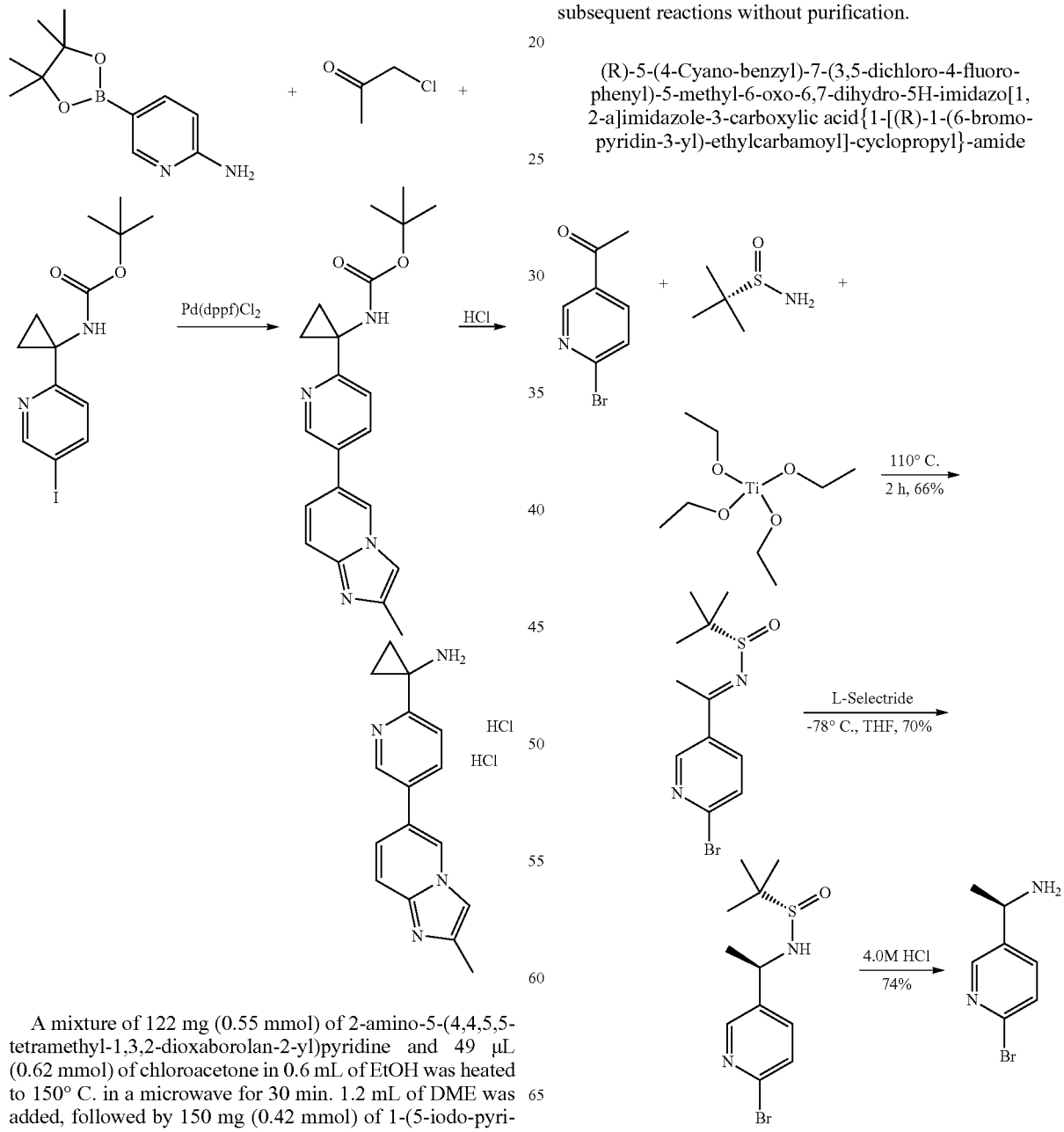

A mixture of 122 mg (0.55 mmol) of 2-amino-5-(4,4,5,5-tetramethyl-1,3,2-dioxaborolan-2-yl)pyridine and 49 μL (0.62 mmol) of chloroacetone in 0.6 mL of EtOH was heated to 150° C. in a microwave for 30 min. 1.2 mL of DME was added, followed by 150 mg (0.42 mmol) of 1-(5-iodo-pyridin-2-yl)-cyclopropyl]-carbamic acid tert-butyl ester, 34 mg -continued

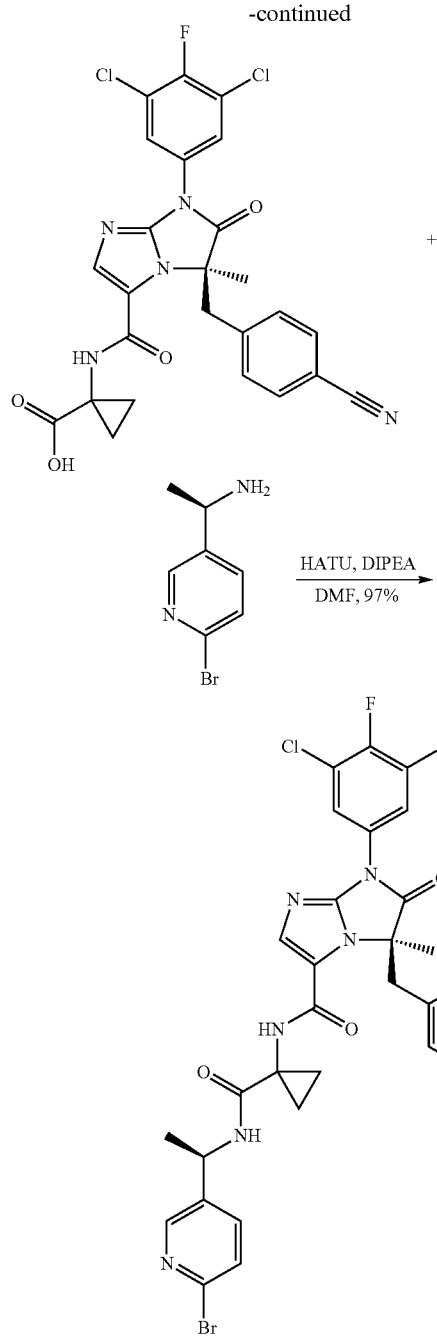

To a solution of 2-bromo-5-isopropyl-pyridine (2.0 g, 9.99 mmol) in dichloroethane (15 mL) was added (S)-(−)-2-methyl-propane-2-sulfinic acid amide (1.45 g, 11.72 mmol) and titanium(IV) ethoxide (4.15 mL, 19.99 mmol). The mixture was heated at 110° C. in a microwave. After 2 h, the mixture was diluted with ether (20 mL) and water (6 mL). The mixture was stirred for 10 minutes. The layers were separated and the organic layer was dried over magnesium sulfate, filtered and concentrated to afford a residue. The crude residue was purified by normal phase flash chromatography on silica gel using ethyl acetate-dichloromethane (0-40%) to afford 2-methyl-propane-2-sulfinic acid[1-(6-bromo-pyridin-3-yl)-eth-(E)-ylidene]-amide (2.0 g, 66%).

To a chilled (−78° C.) solution of 2-methyl-propane-2-sulfinic acid[1-(6-bromo-pyridin-3-yl)-eth-(E)-ylidene]-amide (1.0 g, 3.30 mmol) in THF (25 mL) was dropwise added lithium tri-sec-butylborohydride solution in THF (L-Selectride, 3.30 mL, 3.30 mmol). The mixture darkened in color upon addition of this reagent. After 3 hours, the mixture was quenched with saturated aqueous ammonium chloride (30 mL) and extracted with ethyl acetate (3×25 mL). The combined organic layers were washed with brine (3×30 mL), dried over magnesium sulfate, filtered and concentrated. The crude material was purified via normal phase flash chromatography on silica gel eluting with ethyl acetate-dichloromethane (0-100%) to afford 2-methyl-propane-2-sulfinic acid[(R)-1-(6-bromo-pyridin-3-yl)-ethyl]-amide (700 mg, 70%) as a slightly yellow solid.

To a solution of 2-methyl-propane-2-sulfinic acid[(R)-1-(6-bromo-pyridin-3-yl)-ethyl]-amide (650 mg, 2.13 mmol) in MeOH (5 mL) was added 4.0M HCl in dioxane (5.32 mL, 21.30 mmol). The clear reaction mixture was stirred at room temperature for 2.5 h. The reaction mixture became cloudy during this time. Ether (20 mL) was added, and the mixture was stirred for 10 min and then filtered, washed with ether (20 mL) to afford (R)-1-(6-bromo-pyridin-3-yl)-ethylamine HCl salt (500 mg, 87%) as a white solid.

To a solution of the above (R)-1-(6-bromo-pyridin-3-yl)-ethylamine HCl salt (500 mg, 1.82 mmol) in DMF (10 mL) was added 1-{[(R)-5-(4-Cyano-benzyl)-7-(3,5-dichloro-4-fluoro-phenyl)-5-methyl-6-oxo-6,7-dihydro-5H-imidazo[1,2-α]imidazole-3-carbonyl]-amino}-cyclopropanecarboxylic acid (900 mg, 1.66 mmol) and diisopropylethylamine (1.45 mL, 8.30 mmol). The mixture was stirred at room temperature for 5 min. HATU (694 mg, 1.83 mmol) was added to the mixture and the clear yellow mixture was stirred for 17 h. The mixture was diluted with ethyl acetate (35 mL) and washed with water (8 mL). The organic phase was washed with 5% aqueous NaCl solution (2×10 mL) and brine (20 mL), dried over $Na_2SO_4$, filtered, and concentrated to pale yellow oil. The crude oil was purified via flash chromatography on silica gel, eluting with 1-6% MeOH/$CH_2Cl_2$, to afford 1.3 g of the title compound as a yellow foam.

1-[5-(5-Cyclopropyl-1,2,4-oxadiazol-3-yl)-pyridin-2-yl]-cyclopropylamine hydrochloride

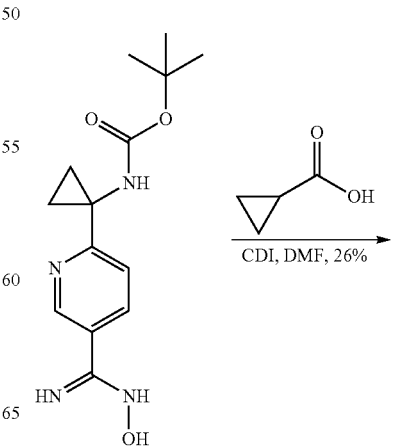

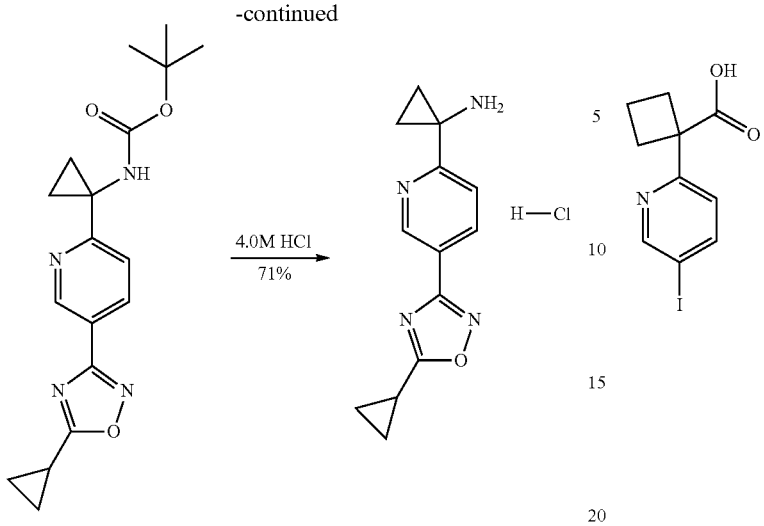

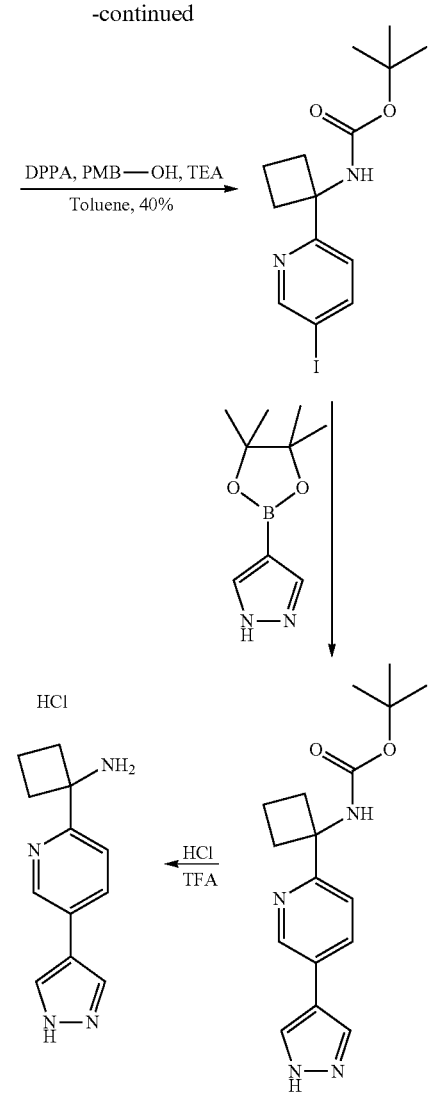

An 8-mL vial was charged with cyclopropanecarboxylic acid (78.5 μL, 0.99 mmol) and DMF (1.0 mL). Carbonyldiimidazole (176 mg, 1.09 mmol) was added to the vial at room temperature. The clear reaction mixture was stirred for 2 h and then added to another 8-mL vial containing {1-[5-(N-hydroxycarbamimidoyl)-pyridin-2-yl]-cyclopropyl}-carbamic acid tert-butyl ester (430 mg, 1.47 mmol) in 1.0 mL of DMF. The resulting pale yellow reaction mixture was stirred at room temperature for 30 min and then heated at 100° C. for 16 h. The clear pale orange reaction mixture was quenched with water (10 mL) and extracted with ethyl acetate (2×20 mL). The organics were washed with of water (2×15 mL) and brine (15 mL), dried over Na$_2$SO$_4$, filtered, and concentrated to a crude oil. The crude oil was purified via normal phase flash chromatography on silica gel, eluting with 0-35% EtOAc/hexanes, to give {1-[5-(5-cyclopropyl-1,2,4-oxadiazol-3-yl)-pyridin-2-yl]-cyclopropyl}-carbamic acid tert-butyl ester (86 mg, 26%) as a white solid.

To the solution of {1-[5-(5-cyclopropyl-1,2,4-oxadiazol-3-yl)-pyridin-2-yl]-cyclopropyl}-carbamic acid tert-butyl ester (80 mg, 0.23 mmol) in CH$_2$Cl$_2$ (10 mL) was added 4M HCl (2 mL, 8 mmol). After stirring overnight, more 4M HCl (0.1 mL, 0.4 mmol) was added. After a total of 42 h, diethyl ether (10 mL) was added to the reaction mixture and stirring was continued for 10 min. The reaction suspension was filtered and the solid was washed with ether (10 mL) to afford 1-[5-(5-cyclopropyl-1,2,4-oxadiazol-3-yl)-pyridin-2-yl]-cyclopropylamine HCl salt (40 mg) as a white solid.

1-[5-(1H-Pyrazol-4-yl)-pyridin-2-yl]-cyclobutylamine dihydrochloride

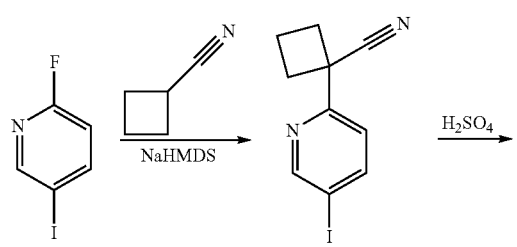

In a dry flask under argon, 2-fluoro-5-iodo-pyridine (3.85 g, 17.3 mmol) and cyclobutanecarbonitrile (1.40 g, 17 mmol) were dissolved in dry toluene (15 mL). The solution was cooled to 0° C. and sodium bis(trimethylsilyl)amide (1.0 M, 19 mL, 19 mmol) was added dropwise over 15 min. After 1 h, the solution was allowed to warm to room temperature and stirred for 26 h. The reaction was diluted with saturated aqueous NH$_4$Cl (10 mL) and CH$_2$Cl$_2$ (10 mL). The layers were separated and the aqueous layer was extracted with CH$_2$Cl$_2$ (2×10 mL). The combined organic layers were dried over MgSO$_4$, filtered and concentrated in vacuo to yield 4.0 g of 1-(5-iodo-pyridin-2-yl)-cyclobutane carbonitrile as a viscous, light brown oil, m/z 285.4 [M+H]$^+$.

1-(5-Iodo-pyridin-2-yl)-cyclobutane carbonitrile (4.0 g, 14 mmol) was combined with water (5.0 mL), glacial AcOH (5.0 mL) and concentrated sulfuric acid (5.0 mL). The homogeneous solution was heated to reflux (external bath: 115° C.). After 5 h, the solution was cooled to room temperature and poured into water (10 mL) and Et$_2$O (15 mL). The layers were separated and the Et$_2$O layer was discarded. The aqueous layer was adjusted to pH 4.5-5 by the addition of 2M aq. NaOH and then extracted with CH$_2$Cl$_2$ (3×50 mL). The combined CH$_2$Cl$_2$ layers were washed with brine, dried over MgSO₄, filtered and concentrated to yield 3.92 g of 1-(5-iodo-pyridin-2-yl)-cyclobutane carboxylic acid, m/z 304.4 [M+H]⁺.

1-(5-Iodo-pyridin-2-yl)-cyclobutane carboxylic acid (3.92 g, 12.9 mmol) was combined with tert-BuOH (6.1 mL, 65 mmol), Et₃N (9.0 mL, 65 mmol) and DPPA (3.1 mL, 14 mmol). The reaction was heated to reflux (external bath: 85° C.) for 1.5 h. The volatiles were removed in vacuo and the crude reaction mixture was purified by normal phase flash chromatography on silica gel (5→80% EtOAc/hexanes) to give 1.1 g of [1-(5-iodo-pyridin-2-yl)-cyclobutyl]-carbamic acid tert-butyl ester as a solid, m/z 375.4 [M+H]⁺.

To a mixture of [1-(5-iodo-pyridin-2-yl)-cyclobutyl]-carbamic acid tert-butyl ester (0.46 g, 1.23 mmol), 4-(4,4,5,5-tetramethyl-1,3,2-dioxaborolan-2-yl)-pyrazole-1-carboxylic acid tert-butyl ester (0.4 g, 1.35 mmol), and PdCl₂(dppf) Cl₂·dichloromethane complex (0.2 g, 0.25 mmol) in DME/H₂O/EtOH (4 mL, 7:3:2) in a sealable microwave tube was added 1M K₃PO₄ (1.5 mL, 1.5 mmol). The tube was sealed and heated in microwave at 100° C. for 10 minutes and then 120° C. for 20 minutes. 2M NaOH was added (2 mL) and stirred for 10 minutes. The solution was extracted with EtOAc (100 mL). The organic phase was washed with brine, dried over MgSO₄, filtered through diatomaceous earth, and concentrated. The crude oil was purified via normal phase flash chromatography on silica gel eluting with 0-6% MeOH/CH₂Cl₂, to afford {1-[5-(1H-pyrazol-4-yl)-pyridin-2-yl]-cyclobutyl}-carbamic acid tert-butyl ester (0.40 g) as a brown solid, m/z 315.5 [M+H]⁺.

To a solution of {1-[5-(1H-pyrazol-4-yl)-pyridin-2-yl]-cyclobutyl}-carbamic acid tert-butyl ester (300 mg, 0.96 mmol) in CH₂Cl₂ (5 mL) was added TFA (0.37 mL, 4.8 mmol). After 15 h, 4M HCl in dioxane (1.2 mL, 4.8 mmol) was added. After 1 h, the reaction was concentrated in-vacuo to yield 303 mg of the title compound, m/z 215.4 [M+H]⁺.

{5-[6-(1-Amino-1-methyl-ethyl)-pyridazin-3-yl]-pyridin-2-yl]-methanol dihydrochloride A solution of 6-chloro-pyridazine-3-carbonitrile (prepared according to MacDonald et al., WO/2008/068277) (100 mg, 0.71 mmol) in dry THF (3.6 mL) was cooled to −50° C. in a dry ice/acetone bath. Methylmagnesium bromide (1.0 M in MePh/THF, 0.54 mL, 0.75 mmol) was added via syringe in one portion. The cold bath was removed and the reaction was stirred for 1.5 h. To the reaction mixture was added saturated aqueous NH₄Cl and this mixture was extracted with EtOAc (3×). The combined organics were dried over MgSO₄ and concentrated. The resulting residue was purified by flash chromatography (silica, 0→4% MeOH/CH₂Cl₂) to give 34 mg of 1-(6-chloro-pyridazin-3-yl)-ethanone as a brown semi-solid, m/z 157.3 [M+H]⁺.

To a solution of 1-(6-chloro-pyridazin-3-yl)-ethanone (34 mg, 0.22 mmol) in dry THF (1.0 mL) was added 2-methyl-propane-2-sulfinic acid amide (29 mg, 0.24 mmol). Ti(OEt)₄ (0.090 mL, 0.43 mmol) was added in one portion and the reaction was heated to 60° C. for 1 h. Water was added to the reaction mixture and the resulting slurry was filtered through a pad of diatomaceous earth. The filtrate was dried over Na₂SO₄ and was concentrated to provide 2-methyl-propane-2-sulfinic acid[1-(6-chloro-pyridazin-3-yl)-eth-(E)-ylidene]-amide as a crude residue that was used without purification, m/z 260.5 [M+H]⁺.

Crude 2-methyl-propane-2-sulfinic acid[1-(6-chloro-pyridazin-3-yl)-eth-(E)-ylidene]-amide (56 mg, 0.22 mmol) was dissolved in dry THF (2.2 mL) and cooled to −20° C. under an atmosphere of inert gas. Methylmagnesium bromide (1.0 M in MePh/THF, 0.26 mL, 0.26 mmol) was added in one portion via syringe and the reaction was stirred −20° C. for 1.5 h. To the reaction mixture was added saturated aqueous NH₄Cl (4 mL) and EtOAc (7 mL). The layers were separated and the aqueous layer was extracted with EtOAc (2×5 mL). The combined organic layers were dried over Na₂SO₄, concentrated and then purified by flash chromatography (silica, 0→4% MeOH/CH₂Cl₂). 15 mg of impure 2-methyl-propane-2-sulfinic acid[1-(6-chloro-pyridazin-3-yl)-1-methyl-ethyl]-amide was isolated as a light brown solid. This material was used without further purification.

Impure 2-methyl-propane-2-sulfinic acid[1-(6-chloro-pyridazin-3-yl)-1-methyl-ethyl]-amide (15 mg, 0.054 mmol) was combined with Pd(dppf)Cl₂·dichloromethane complex (4.7 mg, 0.006 mmol), 1M K₃PO₄ (0.07 mL, 0.07 mmol) and 2-(hydroxymethyl)pyridine-5-boronic acid (18 mg, 0.12

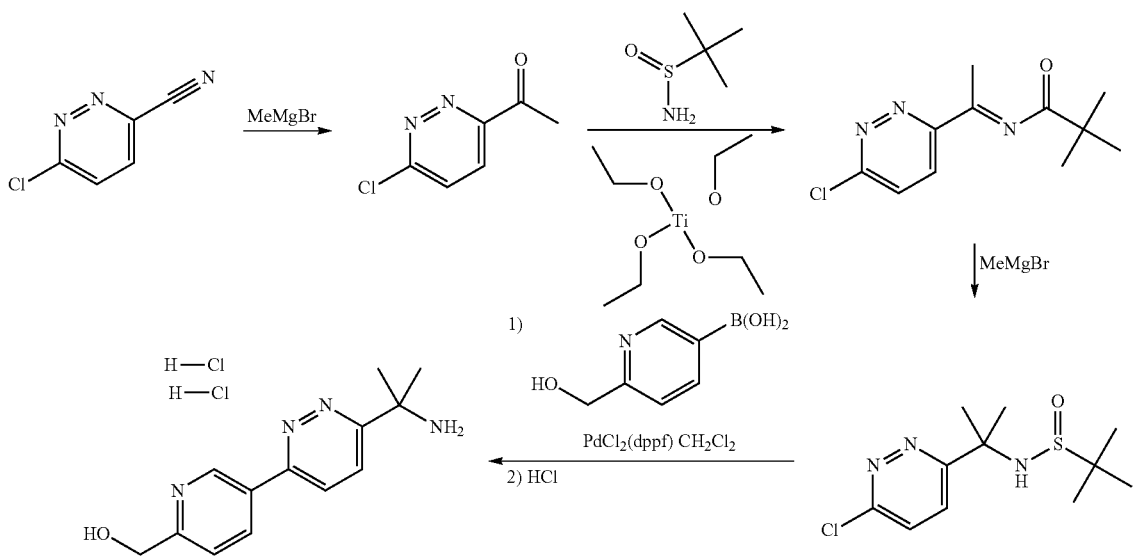

mmol) in a microwave vial. A 7:3:2 mixture of DME/H₂O/ EtOH (1 mL) was added. The vial was flushed with argon and sealed. This vial was then heated in the microwave reactor for 15 min at 140° C. The reaction mixture was diluted with 2 mL of water and extracted 4×4 mL with EtOAc. The combined organic layers were dried over MgSO₄, filtered and concentrated. Purification via normal phase flash chromatography on silica gel (0→4% MeOH/CH₂Cl₂) yielded 4 mg of 2-methyl-propane-2-sulfinic acid{1-[6-(6-hydroxymethyl-pyridin-3-yl)-pyridazin-3-yl]-1-methyl-ethyl}-amide as a brown solid.

2-Methyl-propane-2-sulfinic acid{1-[6-(6-hydroxymethyl-pyridin-3-yl)-pyridazin-3-yl]-1-methyl-ethyl}-amide (4 mg, 0.011 mmol) was dissolved in CH₂Cl₂ (0.25 mL) and 4M HCl in dioxane (2 mL, 8 mmol) was added. After 45 minutes, the solvent was removed under a stream of N₂ to give {5-[6-(1-amino-1-methyl-ethyl)-pyridazin-3-yl]-pyridin-2-yl}-methanol dihydrochloride as a crude light brown solid residue. This was used without further purification.

3-Dimethylamino-2-iodo-propenal

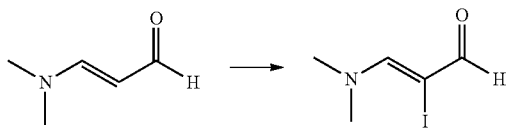

To a solution of 3-dimethylamino-propenal (1.5 mL, 15 mmol) in CH₂Cl₂ (60 mL) at room temperature was added N-iodosuccinimide (3.38 g, 15 mmol) as a solid in a single portion. The reaction was stirred for 1 h followed by the addition of CH₂Cl₂ (25 mL). The reaction mixture was washed with sat aqueous Na₂S₂O₃ (1×75 mL) and water (2×50 mL). The organic phase was dried over Na₂SO₄ and concentrated to give a black solid. Recrystallized from EtOAc/hexanes to give 1.27 g of the title compound as reddish crystals, m/z 226.3 [M+H]⁺.

3-Dimethylamino-2-bromo-propenal

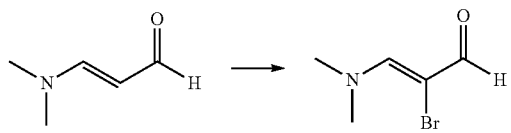

3-Dimethylamino-propenal (50 mL, 500 mmol) was dissolved in CHCl₃ (400 mL) at room temperature. Bromine (25.7 mL, 500 mmol) was added neat via syringe over 5 min. After 30 min, the reaction was poured into 200 mL saturated aqueous Na₂S₂O₃ and 200 mL sat NaHCO₃. This mixture was extracted with CH₂Cl₂ (3×100 mL). The combined organic layers were dried over MgSO₄ and concentrated to give dark colored solids. These solids were dissolved in EtOAc (200 mL) and the insoluble materials were filtered off. The filtrate was concentrated in vacuo and the resulting solids were washed with 50% EtOAc/hexanes to give 50.0 g of the title compound as a pale yellow solid, m/z 178.28 [M+H]⁺.

(R)-5-(4-Cyano-benzyl)-7-(3,5-dichloro-4-fluorophenyl)-5-methyl-6-oxo-6,7-dihydro-5H-imidazo[1, 2-a]imidazole-3-carboxylic acid{1-[1-(5-iodo-pyrimidin-2-yl)-cyclopropylcarbamoyl]-cyclopropyl}-amide

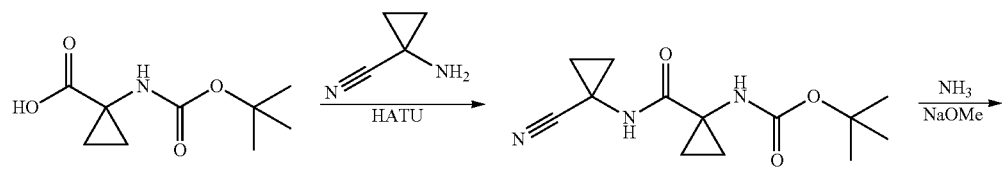

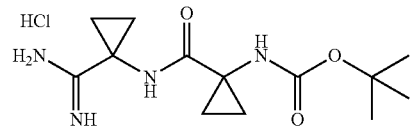

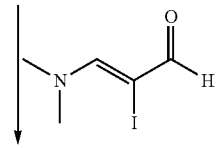

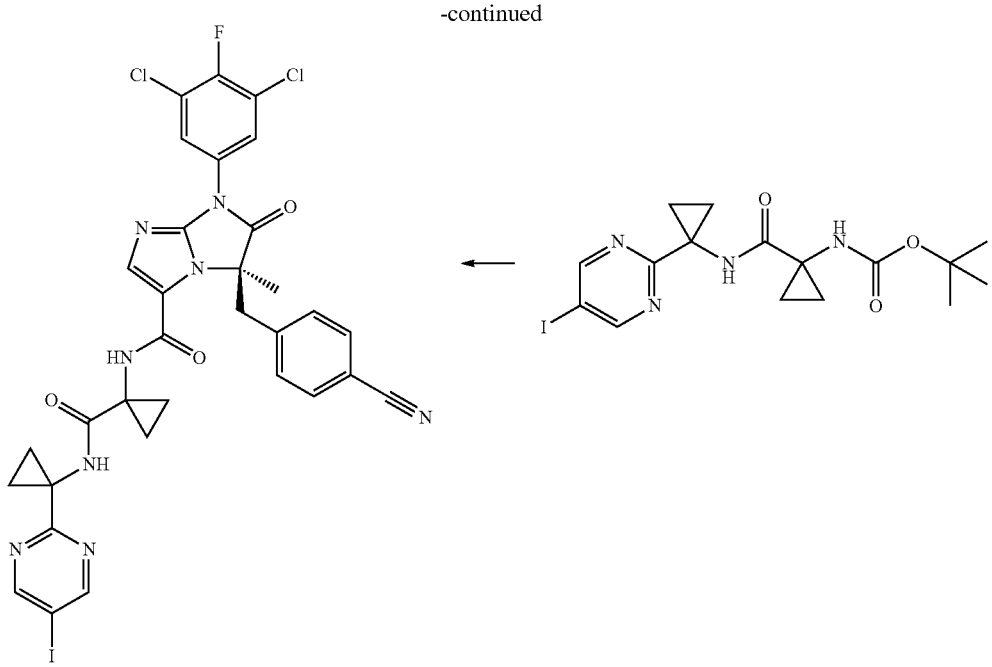

To a suspension of the 1-[(tert-butoxycarbonyl)amino]cyclopropanecarboxylic acid (1.7 g, 8.43 mmol), HATU (3.5 g, 9.3 mmol), and 1-aminocyclopropanecarbonitrile hydrochloride (1.0 g, 8.43 mmol) in THF (34 mL) was added triethylamine (3.5 mL, 25.3 mmol). The yellow suspension was stirred at room temperature for 18 h then most of the THF was removed in-vacuo. The remaining slurry was diluted with 150 mL 10% (w/w) aqueous Na$_2$CO$_3$ and 150 mL EtOAc. The layers were separated and the organic phase was washed with 10% (w/w) aqueous Na$_2$CO$_3$ (2×100 mL). The organic phase was washed with brine (1×75 mL), dried with Na$_2$SO$_4$, filtered, and concentrated to afford a crude light orange solid. This solid was triturated with Et$_2$O and the white solid was filtered off using Et$_2$O to rinse to yield 1.8 g of [1-(1-cyano-cyclopropylcarbamoyl)-cyclopropyl]-carbamic acid tert-butyl ester as an off-white solid, m/z 266.5 [M+H]$^+$.

To a solution of [1-(1-cyano-cyclopropylcarbamoyl)-cyclopropyl]-carbamic acid tert-butyl ester (250 mg, 0.942 mmol) in anhydrous EtOH (2.4 mL) was added NaOEt (21 wt % in EtOH, 0.70 mL, 1.9 mmol) via syringe in one portion. The orange reaction was stirred for 1 h. To the orange solution was added solid NH$_4$Cl (202 mg, 3.77 mmol) and NH$_3$ (7M in MeOH, 0.14 mL, 0.94 mmol). The reaction vial was sealed and stirred at room temperature for 15 h. The resulting suspension was filtered rinsing with EtOH. The filtrate was concentrated and the resulting solids were triturated with EtOAc to give 182 mg of [1-(1-carbamimidoyl-cyclopropylcarbamoyl)-cyclopropyl]-carbamic acid tert-butyl ester hydrochloride as a white solid, m/z 283.6 [M+H]$^+$.

To a solution of [1-(1-carbamimidoyl-cyclopropylcarbamoyl)-cyclopropyl]-carbamic acid tert-butyl ester hydrochloride (1.65 g, 5.2 mmol) in anhydrous EtOH (21 mL) was added 3-dimethylamino-2-iodo-propenal (1.3 g, 5.63 mmol) and 2M dimethylamine in THF (3.36 mL, 6.7 mmol). The vessel was capped and heated at 70° C. overnight. After 18 h, EtOH was removed in-vacuo and the dark orange residue was triturated with 5% iPrOH in EtOAc. A yellow solid was filtered off. The filtrate was concentrated in vacuo and purified by normal phase flash chromatography on silica gel (0→5% MeOH/CH$_2$Cl$_2$) to yield a black oil. This oil was treated with Et$_2$O to precipitate a white solid. The solid was filtered off and the filtrate was reprocessed to give another crop of slightly darker solids. A total of 426 mg of {1-[1-(5-iodo-pyrimidin-2-yl)-cyclopropylcarbamoyl]-cyclopropyl}-carbamic acid tert-butyl ester was isolated, m/z 445.5 [M+H]$^+$.

{1-[1-(5-iodo-pyrimidin-2-yl)-cyclopropylcarbamoyl]-cyclopropyl}-carbamic acid tert-butyl ester (426 mg, 0.96 mmol) was dissolved in CH$_2$Cl$_2$ (2 mL) and 4M HCl in dioxane 3 mL, 6 mmol) was added. After 90 minutes, the volatiles were removed at 60° C. under a stream of N$_2$. The resulting while solid was dried under vacuum overnight to yield crude 400 mg of 1-amino-cyclopropanecarboxylic acid [1-(5-iodo-pyrimidin-2-yl)-cyclopropyl]-amide dihydrochloride. This material was used without further purification.

To 1-amino-cyclopropanecarboxylic acid[1-(5-iodo-pyrimidin-2-yl)-cyclopropyl]-amide dihydrochloride (400 mg, 0.96 mmol) was added 1 mL of dry THF and triethylamine (0.71 ml, 3.98 mmol). Crude (R)-5-(4-cyano-benzyl)-7-(3,5-dichloro-4-fluoro-phenyl)-5-methyl-6-oxo-6,7-dihydro-5H-imidazo[1,2-a]imidazole-3-carbonyl chloride (476 mg, 1.0 mmol) was dissolved in 2 mL of dry THF and transferred to the reaction flask. After 2 h, the solvent was removed at 55° C. under a stream of N$_2$. The resulting slurry was diluted with EtOAc (75 mL) and washed with 10% aq citric acid (75 mL) and saturated aq NaHCO$_3$ (75 mL). The organic layer was dried over Na$_2$SO$_4$ and concentrated to give a light orange foam. This solid was purified by normal phase flash chromatography on silica gel (1→3% MeOH/CH$_2$Cl$_2$) to give 767 mg of the title compound as a tan powder, m/z 785.5.

1-(5-Bromo-pyrimidin-2-yl)-cyclopropylamine dihydrochloride

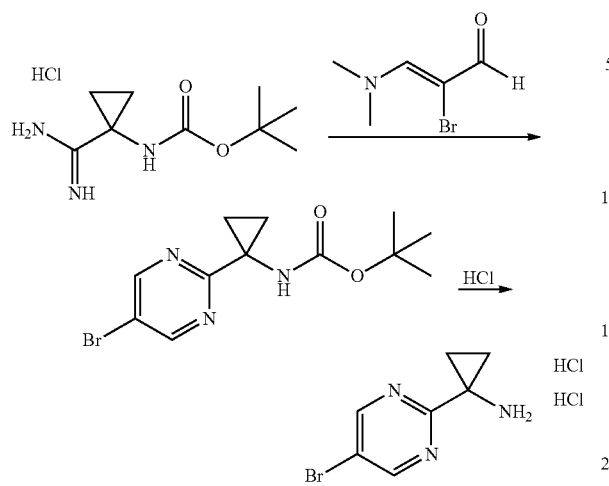

[1-(1-Carbamimidoyl-cyclopropylcarbamoyl)-cyclopropyl]-carbamic acid tert-butyl ester hydrochloride (1.0 g, 4.2 mmol) (made from (1-cyano-cyclopropyl)-carbamic acid tert-butyl ester using a procedure similar to that of [1-(1-carbamimidoyl-cyclopropyl-carbamoyl)-cyclopropyl]-carbamic acid tert-butyl ester) and 2-bromo-3-dimethylamino-acrolein (1.1 g, 6.36 mmol) were combined in EtOH (2 mL) in a sealed tube. The reaction was capped and the mixture heated at 80° C. for 24 hours. The resulting black mixture was allowed to cool to room temperature. Methanol (20 mL) was then added to the reaction solution. The solids were filtered and the resulting solution was dried under reduced pressure. The residue was diluted with 50 mL CH$_2$Cl$_2$ and the solids were removed. The solution was concentrated and purified by normal phase flash chromatography on silica gel (0→50% EtOAc in hexanes) to give 800 mg of [1-(5-bromo-pyrimidin-2-yl)-carbamic acid tert-butyl ester as an off-white solid.

[1-(5-Bromo-pyrimidin-2-yl)-carbamic acid tert-butyl ester (1.18 g, 3.76 mmol) was dissolved in CH$_2$Cl$_2$ (5 mL) at room temperature. 4M HCl in dioxane (9.4 mL, 37.6 mmol) was added. After 2 h, the solvents were removed by a stream of N$_2$ to give the title compound as a solid, m/z=216.3. The crude material was used without purification in subsequent steps.

General Procedure: Suzuki Reaction/Boc Deprotection

1-[5-(1-Methyl-1H-pyrazol-4-yl)-pyridin-2-yl]-cyclopropylamine dihydrochloride

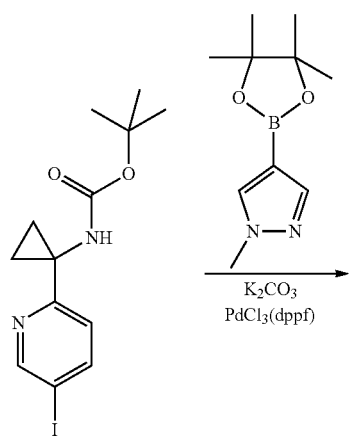

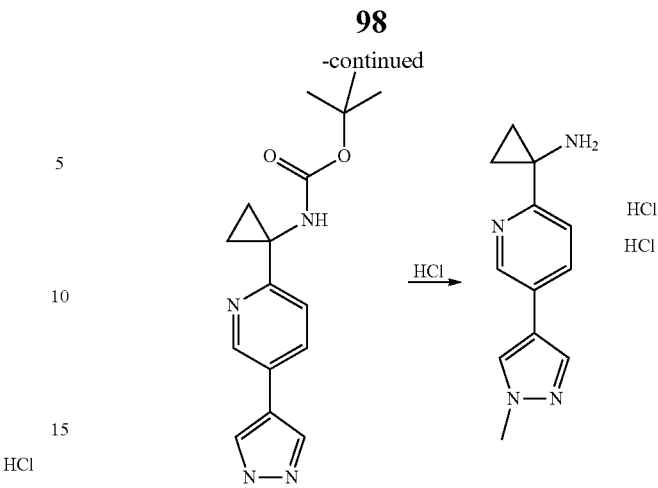

To a mixture of [1-(5-iodo-pyridin-2-yl)-cyclopropyl]-carbamic acid tert-butyl ester (500 mg, 1.39 mmol), 1-methyl-4-(4,4,5,5-tetramethyl-1,3,2-dioxaborolan-2-yl)-1H-pyrazole 433 mg, 2.1 mmol) and Pd(dppf)Cl$_2$.dichloromethane complex (113 mg, 0.14 mmol) in 1.5 mL of DME/H$_2$O/EtOH (7:3:2) in a sealable microwave tube was added 1M aqueous K$_3$PO$_4$ solution (2.1 mL). The tube was sealed and heated in the microwave at 100° C. for 10 min. The crude reaction was filtered through a pad of silica gel, washing with MeOH, and concentrated. The residue was partitioned between 30 mL of EtOAc and 10 mL of water. The organic phase was washed with brine, dried over Na$_2$SO$_4$, filtered, and concentrated to give an oil. This material was purified by normal phase flash chromatography on silica gel (0→3.5% MeOH/CH$_2$Cl$_2$) to give 0.55 g of {1-[5-(1-methyl-1H-pyrazol-4-yl)-pyridin-2-yl]-cyclopropyl}-carbamic acid tert-butyl ester as a brown solid. The compound was used in subsequent steps without further purification.

To a solution of {1-[5-(1-methyl-1H-pyrazol-4-yl)-pyridin-2-yl]-cyclopropyl}-carbamic acid tert-butyl ester (1.1 g, 3.5 mmol) in CH$_2$Cl$_2$ (15 mL), 4.0M HCl in dioxane (4.35 mL, 17.5 mmol) was added. After stirring overnight, more 4.0M HCl in dioxane (4.35 mL, 17.5 mmol) was added to the solution. After another 12 hours, the solution was concentrated in-vacuo to yield 800 mg of the title compound.

The following compounds were prepared using procedures similar to those described above:

1-[5-(6-Methyl-pyridin-3-yl)-pyrimidin-2-yl]-cyclopropylamine
{5-[2-(1-Amino-cyclopropyl)-pyrimidin-5-yl]-pyridin-2-yl}-methanol
1-[5-(1,3-Dimethyl-1H-pyrazol-4-yl)-pyrimidin-2-yl]-cyclopropylamine
1-[5-(1-Methyl-1H-pyrazol-4-yl)-pyrimidin-2-yl]-cyclopropylamine
1-[5-(4-Methanesulfonyl-phenyl)-pyridin-2-yl]-cyclopropylamine{-4-[6-(1-Amino-cyclopropyl)-pyridin-3-yl]-phenyl}-methanol
[5-(1-Amino-cyclopropyl)-[2,3']bipyridinyl-6'-yl]-methanol
1-(6'-Methyl-[2,3']bipyridinyl-5-yl)-cyclopropylamine
1-[5-(1H-Pyrazol-4-yl)-pyridin-2-yl]-cyclopropylamine
1-(6'-Methyl-[3,3']bipyridinyl-6-yl)-cyclopropylamine
1-[5-(1,3,5-Trimethyl-1H-pyrazol-4-yl)-pyridin-2-yl]-cyclopropylamine
{4-[2-(1-Amino-cyclopropyl)-pyrimidin-5-yl]-phenyl}-methanol
1-[6-(1,3-Dimethyl-1H-pyrazol-4-yl)-pyridin-3-yl]-cyclopropylamine 1-[6-(1-Methyl-1H-pyrazol-4-yl)-pyridin-3-yl]-cyclopropylamine
1-[5-(1,3-Dimethyl-1H-pyrazol-4-yl)-pyridin-2-yl]-cyclopropylamine
1-[5-(1-Cyclopropyl-1H-pyrazol-4-yl)-pyridin-2-yl]-cyclopropylamine
1-[5-(3-Cyclopropyl-1-methyl-1H-pyrazol-4-yl)-pyridin-2-yl]-cyclopropylamine
1-[5-(5-Cyclopropyl-1-methyl-1H-pyrazol-4-yl)-pyridin-2-yl]-cyclopropylamine
[6'-(1-Amino-cyclopropyl)-[3,3']bipyridinyl-6-yl]-methanol
1-[6-(1H-Pyrazol-4-yl)-1,8-naphthyridin-2-yl]-cyclobutylamine

1-Cyclopropyl-4-(4,4,5,5-tetramethyl-[1,3,2]dioxaborolan-2-yl)-1H-pyrazole

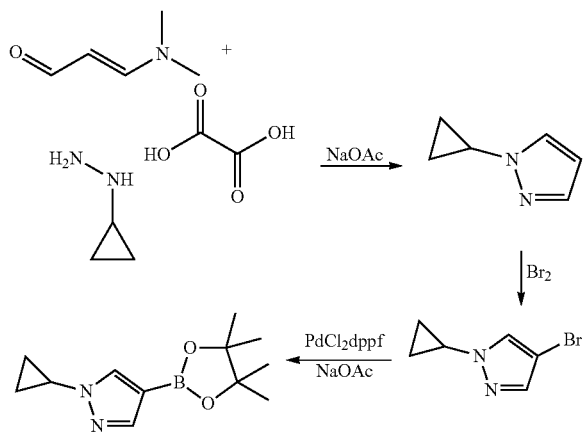

Cyclopropylhydrazine oxalate (162 mg, 1.00 mmol) and NaOAc (82 mg, 1.0 mmol) were combined in EtOH (200 proof, 1.5 mL) and 3-dimethylamino-propenal (0.10 mL, 1.0 mmol) was added in one portion via syringe. The suspension was stirred at 70° C. for 16 h then allowed to cool to room temperature. The reaction was diluted with sat. aq. NaHCO$_3$ (3 mL) and extracted with EtOAc (4×5 mL). The combined organic layers were dried over Na$_2$SO$_4$ and concentrated on a rotary evaporator without heating the sample to give the 1-cyclopropyl-1H-pyrazole as a volatile, liquid that was used without further purification, m/z 109.4 [M+H]$^+$.

To a solution of crude 1-cyclopropyl-1H-pyrazole (108 mg, 1.00 mmol) in CHCl$_3$ (4 mL) at room temperature was added Br$_2$ (51 uL, 1.0 mmol) via syringe. The orange solution was stirred for 1 h. The reaction was diluted with saturated aqueous Na$_2$S$_2$O$_3$ (3 mL) and saturated aqueous NaHCO$_3$ (3 mL). The mixture was extracted with CH$_2$Cl$_2$ (3×5 mL). The combined organic layers were dried over Na$_2$SO$_4$ and concentrated on a rotary evaporator without heating the sample to give 4-bromo-1-cyclopropyl-1H-pyrazole as a volatile, light yellow liquid that was used without further purification, m/z 187.3 [M+H]$^+$.

Bis(pinacolato)diboron (330 mg, 1.3 mmol), NaOAc (262 mg, 3.2 mmol), and Pd(dppf)Cl$_2$.dichloromethane complex (89 mg, 0.11 mmol) were combined in a microwave vial. 4-Bromo-1-cyclopropyl-1H-pyrazole and DMF (4 mL) were added and the vial was flushed with argon and sealed. The reaction mixture was heated in a microwave for 60 min at 150° C. The reaction was diluted with 10 mL water and extracted 3×10 mL with EtOAc. The combined organic layers were dried over Na$_2$SO$_4$ and concentrated to yield 120 mg of the title compound as a dark oil, m/z 235.4 [M+H]$^+$.

1-[6-(1-Methyl-1H-pyrazol-4-yl)-pyridazin-3-yl]-cyclopropylamine dihydrochloride

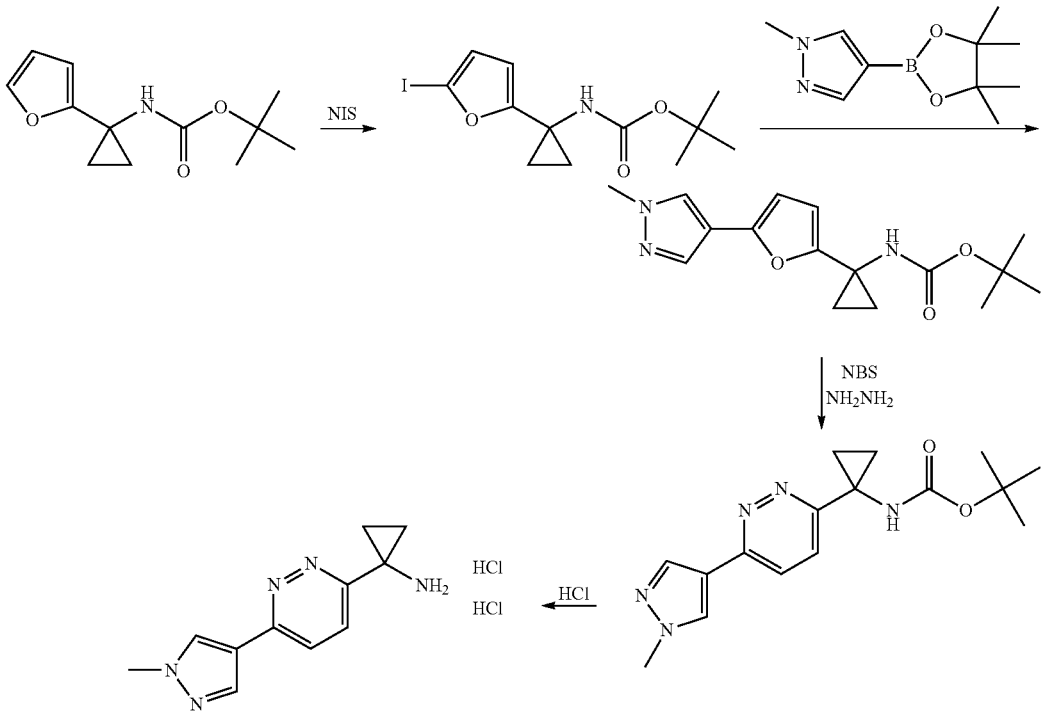

To a solution of (1-furan-2-yl-cyclopropyl)-carbamic acid tert-butyl ester (4.30 g, 19.3 mmol) in anhydrous DMF (77 mL) at room temperature was added N-iodosuccinimide (4.77 g, 21.2 mmol) as a solid in one portion. The reaction was stirred for 2.5 h over which time a deep red color developed. The reaction was diluted with sat. aq. $Na_2S_2O_3$ (75 mL), water (75 mL), and diethyl ether (100 mL). The layers were separated and the aqueous layer was extracted with diethyl ether (2×100 mL). The combined organic layers were dried over $Na_2SO_4$ and concentrated. The resultant solids were triturated with hexanes to give 4.9 g [1-(5-iodo-furan-2-yl)-cyclopropyl]-carbamic acid tert-butyl ester as a light yellow powder, m/z 350.5 [M+H]$^+$.

[1-(5-Iodo-furan-2-yl)-cyclopropyl]-carbamic acid tert-butyl ester (200 mg, 0.57 mmol), Pd(dppf)Cl$_2$.dichloromethane complex (46 mg, 0.057 mmol), $K_3PO_4$ (145 mg, 0.69 mmol) and 1-methyl-4-(4,4,5,5-tetramethyl-1,3,2-dioxaborolan)-1H-pyrazole (179 mg, 0.86 mmol) were all placed into a microwave vial. DME (1.5 mL), water (0.6 mL), EtOH (0.5 mL) were added and the vial was flushed with Argon and then sealed. The reaction mixture was heated in the microwave at 100° C. for 10 minutes. The reaction was diluted with water (5 mL) and extracted with EtOAc (3×5 mL). The organic phase was dried over MgSO$_4$, filtered and concentrated to give a black residue. Purification by normal phase flash chromatography on silica gel (0→4.5% MeOH/CH$_2$Cl$_2$) yielded 226 mg of {1-[5-(1-methyl-1H-pyrazol-4-yl)-furan-2-yl]-cyclopropyl}-carbamic acid tert-butyl ester, m/z 304.6 [M+H]$^+$, as a red semisolid residue.

In a round bottom flask, {1-[5-(1-methyl-1H-pyrazol-4-yl)-furan-2-yl]-cyclopropyl}-carbamic acid tert-butyl ester (226 mg, 0.745 mmol) was dissolved in a mixture of THF (12.4 mL) and water (1.3 mL). The flask was cooled to −35° C. in a dry ice/acetone bath (the mixture becomes a thick slurry) and then N-bromosuccinimide (146 mg, 0.819 mmol) was added as a solid in one portion. The reaction immediately turned a bright yellow color. The reaction was stirred for 15 min at this temperature after which time anhydrous hydrazine (0.21 mL, 6.7 mmol) was added in one portion via syringe. The ice bath was removed and the reaction was allowed to stir at room temperature for 20 h. The volatiles were removed at 50° C. under a stream of N$_2$. The resulting residue was purified by flash chromatography (silica, 90→100% EtOAc/hexanes) to give 51 mg of {1-[6-(1-methyl-1H-pyrazol-4-yl)-pyridazin-3-yl]-cyclopropyl}-carbamic acid tert-butyl ester as a bright yellow solid, m/z 316.6 [M+H]$^+$.

{1-[6-(1-Methyl-1H-pyrazol-4-yl)-pyridazin-3-yl]-cyclopropyl}-carbamic acid tert-butyl ester (51 mg, 0.16 mmol) was dissolved in CH$_2$Cl$_2$ (1 mL) and 4M HCl in dioxane (2 mL, 4 mmol) was added. After 2 h, the solvents removed under a stream of N$_2$ to give the title compound as an orange solid, m/z=216.4 [M+H]$^+$.

The following compounds were prepared using procedures similar to those described above:

1-[6-(4-Fluoro-phenyl)-pyridazin-3-yl]-cyclopropylamine dihydrochloride, m/z 230.4 [M+H]$^+$.

{4-[6-(1-Amino-cyclopropyl)-pyridazin-3-yl]-phenyl}-methanol, m/z 242.3 [M+H]$^+$.

1-[6-(1H-Pyrazol-4-yl)-pyridazin-3-yl]-cyclopropylamine dihydrochloride, m/z 202.4 [M+H]$^+$.

1-[6-(3-Cyclopropyl-1-methyl-1H-pyrazol-4-yl)-pyridazin-3-yl]-cyclopropylamine dihydrochloride, m/z 216.4 [M+H]$^+$.

General Procedure: Amide Coupling/Boc Deprotection Sequence (S)-2-Amino-N-{1-[6-(1H-pyrazol-4-yl)-pyridazin-3-yl]-cyclopropyl}-propionamide dihydrochloride

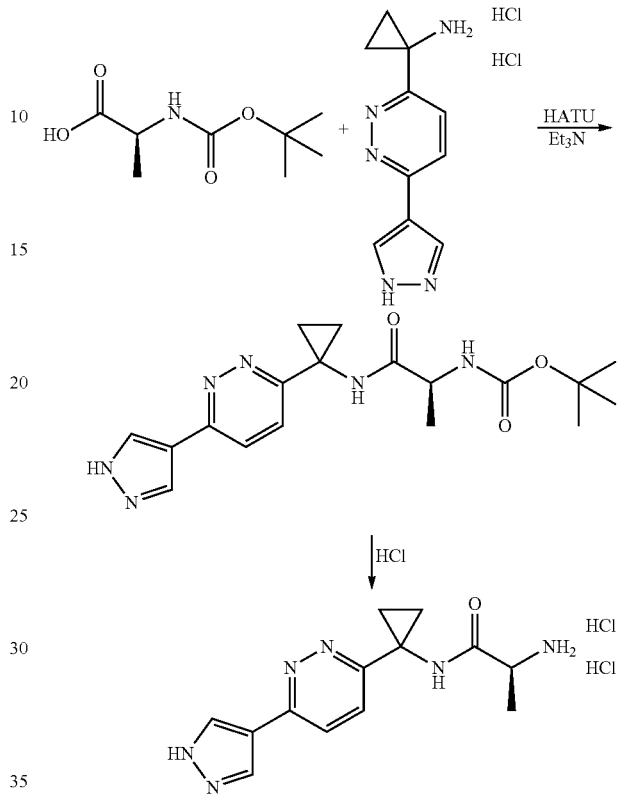

To a solution of the N-Boc-alanine (89 mg, 0.48 mmol), HATU (199 mg, 0.52 mmol), and 1-[6-(1H-pyrazol-4-yl)-pyridazin-3-yl]-cyclopropylamine dihydrochloride (130 mg, 0.48 mmol) in CH$_2$Cl$_2$ (1.9 mL) was added diisopropylethylamine (0.33 mL, 1.9 mmol). The brown mixture was stirred for 2 h then 10% (w/w) aqueous Na$_2$CO$_3$ (5 mL) was added and stirring continued for 20 min. The layers were separated and the aqueous layer was extracted with CH$_2$Cl$_2$ (2×5 mL). The combined organic extracts were dried over Na$_2$SO$_4$, filtered, and concentrated to afford a brown oil. This was purified via normal phase flash chromatography on silica gel (1→20% MeOH/CH$_2$Cl$_2$) to yield mg of ((S)-1-{1-[6-(1H-pyrazol-4-yl)-pyridazin-3-yl]-cyclopropylcarbamoyl}-ethyl)-carbamic acid tert-butyl ester, m/z 373.7 [M+H]$^+$.

((S)-1-{1-[6-(1H-pyrazol-4-yl)-pyridazin-3-yl]-cyclopropylcarbamoyl}-ethyl)-carbamic acid tert-butyl ester was dissolved in CH$_2$Cl$_2$ (1.0 mL) and 4M HCl dioxane (2 mL, 8 mmol) was added. After 1.5 h, the solvents were removed at 50° C. under a stream of N$_2$. This material was dried under vacuum to yield 73 mg of the title compound, m/z 273.5 [M+H]$^+$.

The following compounds were prepared using procedures similar to those described above:

(2S,3R)-2-Amino-3-hydroxy-N-{1-[6-(1H-pyrazol-4-yl)-pyridazin-3-yl]-cyclopropyl}-butyramide dihydrochloride (S)-2-Amino-3-(1-methyl-1H-imidazol-4-yl)-N-{1-[6-(1H-pyrazol-4-yl)-pyridazin-3-yl]-cyclopropyl}-propionamide dihydrochloride (S)-2-Amino-N-[1-(6'-hydroxymethyl-[3,3']bipyridinyl-6-yl)-cyclopropyl]-propionamide dihydrochloride (S)-2-Amino-N-{1-[6-(1-methyl-1H-pyrazol-4-yl)-pyridazin-3-yl]-cyclopropyl}-propionamide dihydrochloride (2S,3R)-2-Amino-3-hydroxy-N-{1-[6-(1-methyl-1H-pyrazol-4-yl)-pyridazin-3-yl]-cyclopropyl}-butyramide dihydrochloride (S)-2-Amino-3-(3-methyl-3H-imidazol-4-yl)-N-{1-[6-(1-methyl-1H-pyrazol-4-yl)-pyridazin-3-yl]-cyclopropyl}-propionamide (S)-2-Amino-3-(3-methyl-3H-imidazol-4-yl)-N-{1-[5-(1-methyl-1H-pyrazol-4-yl)-pyridin-2-yl]-cyclopropyl}-propionamide(S)-2-Amino-N-{1-[5-(1-methyl-1H-pyrazol-4-yl)-pyridin-2-yl]-cyclopropyl}-propionamide (S)-2-Amino-N-{1-[5-(6-hydroxymethyl-pyridin-3-yl)-pyrimidin-2-yl]-cyclopropyl}-propionamide(S)-2-Amino-N-{1-[5-(4-hydroxymethyl-phenyl)-pyridin-2-yl]-cyclopropyl}-propionamide (S)-2-Amino-N-[1-(6'-hydroxymethyl-[2,3']bipyridinyl-5-yl)-cyclopropyl]-propionamide (S)-2-Amino-N-{1-[5-(1H-pyrazol-4-yl)-pyridin-2-yl]-cyclopropyl}-propionamide (2S,3R)-2-Amino-3-hydroxy-N-{1-[5-(1-methyl-1H-pyrazol-4-yl)-pyridin-2-yl]-cyclopropyl}-butyramide(S)-2-Amino-N-{1-[6-(4-hydroxymethyl-phenyl)-pyridazin-3-yl]-cyclopropyl}-propionamide (R)-2-Amino-N-{1-[5-(1-methyl-1H-pyrazol-4-yl)-pyridin-2-yl]-cyclopropyl}-propionamide(2S,3R)-2-Amino-3-hydroxy-N-{1-[5-(6-hydroxymethyl-pyridin-3-yl)-pyrimidin-2-yl]-cyclopropyl}-butyramide 1-Amino-cyclopropanecarboxylic acid{1-[6-(1,3-dimethyl-1H-pyrazol-4-yl)-pyridin-3-yl]-cyclopropyl}-amide (2S,3R)-2-Amino-N-{1-[6-(1,3-dimethyl-1H-pyrazol-4-yl)-pyridin-3-yl]-cyclopropyl}-3-hydroxy-butyramide (2S,3R)-2-Amino-3-hydroxy-N-{1-[6-(1-methyl-1H-pyrazol-4-yl)-pyridin-3-yl]-cyclopropyl}-butyramide (S)-2-Amino-3-hydroxy-N-{1-[5-(1-methyl-1H-pyrazol-4-yl)-pyridin-2-yl]-cyclopropyl}-propionamide (S)-2-Amino-N-{1-[5-(1,3-dimethyl-1H-pyrazol-4-yl)-pyridin-2-yl]-cyclopropyl}-3-hydroxy-propionamide (2S,3R)-2-Amino-N-{1-[5-(1,3-dimethyl-1H-pyrazol-4-yl)-pyridin-2-yl]-cyclopropyl}-3-hydroxy-butyramide (2S,3R)-2-Amino-N-{1-[5-(1,3-dimethyl-1H-pyrazol-4-yl)-pyrimidin-2-yl]-cyclopropyl}-3-hydroxy-butyramide (R)-1-(5-Bromo-pyridin-2-yl)-ethylamine dihydrochloride

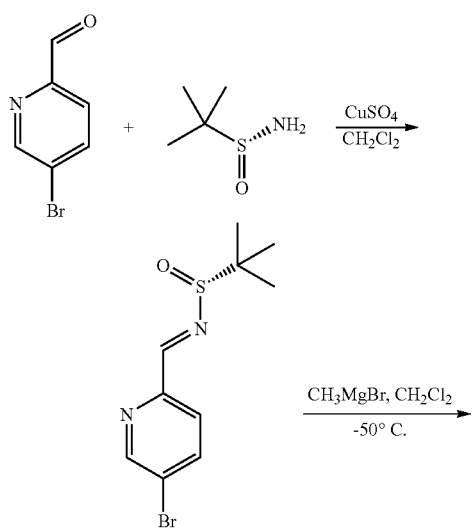

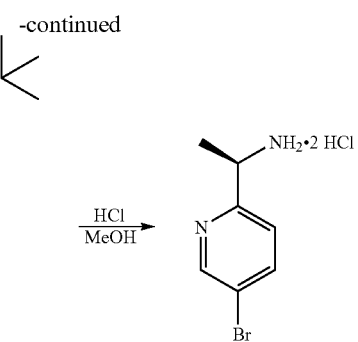

To a solution of (R)-(+)-2-methyl-2-propanesulfinamide (2.60 g, 21.5 mmol) in 100 mL of CH$_2$Cl$_2$ at room temperature was added CuSO$_4$ (7.53 g, 47.2 mmol) and 5-bromo-pyridine-2-carbaldehyde (4.39 g, 23.6 mmol). The reaction mixture was stirred at room temperature for 21 h and then filtered through Diatomaceous earth, washing with CH$_2$Cl$_2$. The filtrates were concentrated to give a pale brown oil that was purified by flash chromatography on silica gel, eluting with 10-25% EtOAc in hexanes, to afford 6.04 g (97%) of (R)-2-methyl-propane-2-sulfinic acid 1-(5-bromo-pyridin-2-yl)-meth-(E)-ylideneamide as a pale yellow solid.

A solution of (R)-2-methyl-propane-2-sulfinic acid 1-(5-bromo-pyridin-2-yl)-meth-(E)-ylideneamide (6.04 g, 20.9 mmol) in 100 mL of CH$_2$Cl$_2$ was cooled to –50° C. MeMgBr (10.4 mL, 31.3 mmol, 3M in Et$_2$O) was added slowly dropwise via syringe pump over 1 h. The reaction mixture was stirred at –50° C. for 30 min and then quenched by the addition of 100 mL of satd aqueous NH$_4$Cl solution. The mixture was partitioned between 200 mL of CH$_2$Cl$_2$ and 150 mL of water. The organic phase was washed with 150 mL of brine, dried over Na$_2$SO$_4$, and concentrated. The residue was purified by flash chromatography on silica gel, eluting with 50-90% EtOAc in hexanes, to provide 5.38 g (84%) of (R)-2-methyl-propane-2-sulfinic acid[(R)-1-(5-bromo-pyridin-2-yl)-ethyl]-amide as a white solid.

To a solution of (R)-2-methyl-propane-2-sulfinic acid[(R)-1-(5-bromo-pyridin-2-yl)-ethyl]-amide (500 mg, 1.64 mmol) in 5 mL of MeOH was added HCl (4.10 mL, 16.4 mmol, 4M in dioxane). The reaction mixture was stirred at room temperature for 2.5 h, during which time a white precipitate was formed. 20 mL of Et$_2$O was added. After stirring for an additional 20 min, the reaction mixture was filtered, washing with 10 mL of Et$_2$O. 454 mg (99%) of the title compound was isolated as a white solid after drying under high vacuum.

General Procedure: Amide Coupling Sequence (R)-5-(4-Cyano-benzyl)-7-(3,5-dichloro-4-fluoro-phenyl)-5-methyl-6-oxo-6,7-dihydro-5H-imidazo[1,2-a]imidazole-3-carboxylic acid{1-[(R)-1-(5-bromo-pyridin-2-yl)-ethylcarbamoyl]-cyclopropyl}-amide

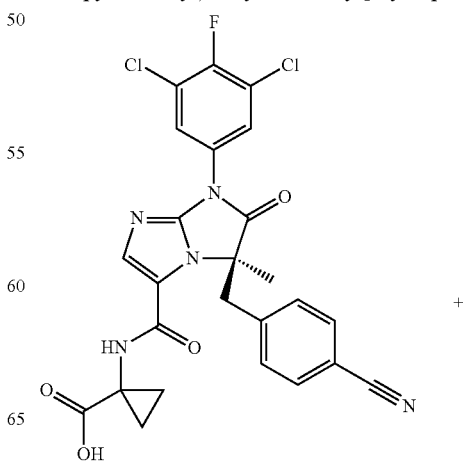

-continued

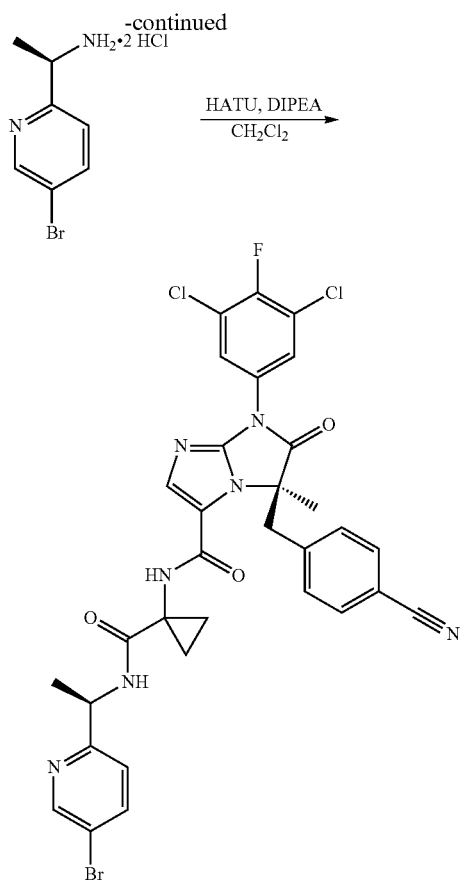

A suspension of 1-{[(R)-5-(4-cyano-benzyl)-7-(3,5-dichloro-4-fluoro-phenyl)-5-methyl-6-oxo-6,7-dihydro-5H-imidazo[1,2-a]imidazole-3-carbonyl]-amino}-cyclopropanecarboxylic acid, (500 mg, 0.92 mmol), (R)-1-(5-bromo-pyridin-2-yl)-ethylamine dihydrochloride (303 mg, 1.11 mmol) and diisopropylethylamine (0.640 mL, 3.69 mmol) in 4 mL of DMF was stirred at room temperature for 10 min HATU (386 mg, 1.01 mmol) was added, and the clear yellow reaction mixture was stirred at room temperature for 3 h. The reaction mixture was partitioned between 75 mL of ethyl acetate and 25 mL of water. The organic phase was washed with 2×25 mL of 5% aqueous NaCl solution and 25 mL of brine, dried over $Na_2SO_4$, filtered, and concentrated in vacuo. The residue was purified by flash chromatography on silica gel, eluting with 0-3% MeOH in $CH_2Cl_2$, to provide 653 mg (98%) of title compound as a yellow foam, m/z 726.4 [M+1]$^+$.

The following compounds were prepared using procedures similar to those described above:

(R)-5-(4-Cyano-benzyl)-7-(3,5-dichloro-phenyl)-5-methyl-6-oxo-6,7-dihydro-5H-imidazo[1,2-a]imidazole-3-carboxylic acid{1-[1-(6-iodo-pyridin-2-yl)-cyclopropylcarbamoyl]-cyclopropyl}-amide(R)-5-(4-Cyano-benzyl)-7-(3,5-dichloro-phenyl)-5-methyl-6-oxo-6,7-dihydro-5H-imidazo[1,2-a]imidazole-3-carboxylic acid{1-[1-(5-iodo-pyridin-2-yl)-cyclopropylcarbamoyl]-cyclopropyl}-amide (R)-5-(4-Cyano-benzyl)-7-(3,5-dichloro-4-fluoro-phenyl)-5-methyl-6-oxo-6,7-dihydro-5H-imidazo[1,2-a]imidazole-3-carboxylic acid{1-[1-(5-iodo-pyridin-2-yl)-cyclopropylcarbamoyl]-cyclopropyl}-amide (R)-7-(3,5-Dichloro-phenyl)-5-methyl-6-oxo-5-(4-trifluoromethoxy-benzyl)-6,7-dihydro-5H-imidazo[1,2-a]imidazole-3-carboxylic acid{1-[1-(5-iodo-pyridin-2-yl)-cyclopropylcarbamoyl]-cyclopropyl}-amide(R)-7-(3,5-Dichloro-4-fluoro-phenyl)-5-methyl-6-oxo-5-(4-trifluoromethoxy-benzyl)-6,7-dihydro-5H-imidazo[1,2-a]imidazole-3-carboxylic acid{1-[1-(5-iodo-pyridin-2-yl)-cyclopropylcarbamoyl]-cyclopropyl}-amide (R)-5-(4-Cyano-benzyl)-7-(3,5-dichloro-phenyl)-5-methyl-6-oxo-6,7-dihydro-5H-imidazo[1,2-a]imidazole-3-carboxylic acid{1-[1-(4-iodo-pyridin-2-yl)-cyclopropylcarbamoyl]-cyclopropyl}-amide General Procedure: Suzuki Reaction/Sulfinamide Deprotection Sequence (2 Step) or Suzuki Reaction/Sulfinamide Deprotection/Amide Coupling/Boc Deprotection Sequence (4 Step)

(2S,3R)-2-Amino-3-hydroxy-N-[(R)-1-(6'-methyl-[3,3']bipyridinyl-6-yl)-ethyl]-butyramide trihydrochloride salt

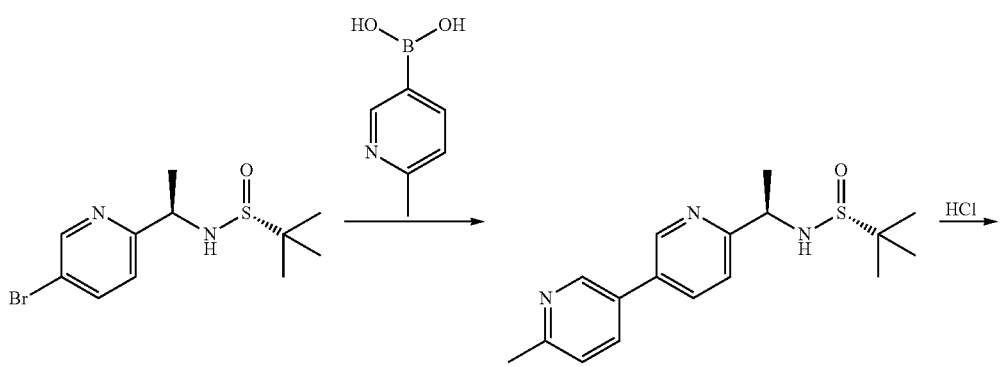

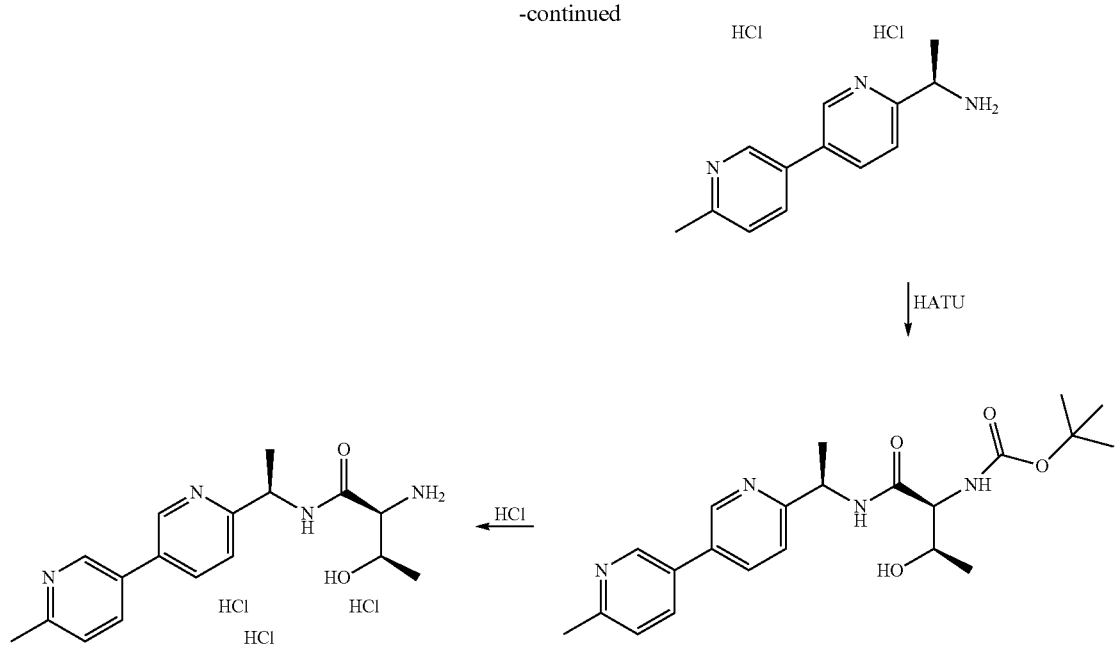

To a mixture of (R)-2-methyl-propane-2-sulfinic acid[(R)-1-(5-bromo-pyridin-2-yl)-ethyl]-amide (500 mg, 1.64 mmol), 2-methylpyridine-5-boronic acid hydrate (305 mg, 2.0 mmol), K₃PO₄ (417 mg, 2.0 mmol), and Pd(dppf)Cl₂.dichloromethane complex (133 mg, 0.16 mmol) in a microwave vial was added 3.3 mL of DME/H₂O/EtOH (7:3:2). The vial was flushed with Ar, sealed and heated in the microwave at 110° C. for 20 min. The reaction was diluted with 30 mL water and 30 mL EtOAc. The layers were separated and the aqueous layer was extracted with EtOAc (2×25 mL). The combined organic layers were dried over MgSO₄ and concentrated to give a black oil. Purification by flash chromatography on silica gel (0→5% MeOH/CH₂Cl₂) yielded 368 mg of 2-methyl-propane-2-(R)-sulfinic acid[(R)-1-(6'-methyl-[3,3']pyridinyl-6-yl)-ethyl]-amide, as a brown crystalline solid, m/z 318.7 [M+H]⁺.

To a solution of 2-methyl-propane-2-(R)-sulfinic acid [(R)-1-(6'-methyl-[3,3']bipyridinyl-6-yl)-ethyl]-amide (370 mg, 1.17 mmol) in CH₂Cl₂ (2 mL) was added 4M HCl in dioxane (3 mL, 12 mmol). After 1.5 h, the solvents were removed under a stream of N₂ to give (R)-1-(6'-methyl-[3,3']bipyridinyl-6-yl)-ethylamine dihydrochloride as a light tan colored solid powder, m/z 214.5 [M+H]⁺.

To a mixture of N-Boc-(L)-threonine (0.13 g, 0.61 mmol), (R)-1-(6'-methyl-[3,3']bipyridinyl-6-yl)-ethylamine dihydrochloride (0.16 g, 0.56 mmol) and HATU (0.23 g, 0.61 mmol) was added THF (1 mL) followed by diisopropylethylamine (0.48 mL, 2.8 mmol). After 2 h, the volatiles were removed under a stream of N₂ and the resulting oil was purified by flash chromatography on silica gel (0→5% MeOH/CH₂Cl₂) yielding 250 mg of {(1S,2R)-2-hydroxy-1-[(R)-1-(6'-methyl-[3,3']bipyridinyl-6-yl)-ethylcarbamoyl]-propyl}-carbamic acid tert-butyl ester as a tan solid, m/z 415.8 [M+H]⁺.

{(1S,2R)-2-hydroxy-1-[(R)-1-(6'-methyl-[3,3']bipyridinyl-6-yl)-ethylcarbamoyl]-propyl}-carbamic acid tert-butyl ester (0.23 g, 0.45 mmol) was dissolved in CH₂Cl₂ (2 mL) and 4M HCl in dioxane (2 mL, 4 mmol) was added. After 1.5 hours, the volatiles were removed under a stream of N₂ to give 300 mg of (2S,3R)-2-amino-3-hydroxy-N-[(R)-1-(6'-methyl-[3,3']bipyridinyl-6-yl)-ethyl]-butyramide trihydrochloride salt as a tan powder, m/z 315.7 [M+H]⁺.

The following compounds were prepared using procedures similar to those described above using either the 2-step or 4-step sequence:

[6'-((R)-1-Amino-ethyl)-[3,3']bipyridinyl-6-yl]-methanol
(S)-2-Amino-N-[(R)-1-(6'-hydroxymethyl-[3,3']bipyridinyl-6-yl)-ethyl]-propionamide
(2S,3R)-2-Amino-3-hydroxy-N-[(R)-1-(6'-hydroxymethyl-[3,3']bipyridinyl-6-yl)-ethyl]-butyramide
(2S,3R)-2-Amino-N-{(R)-1-[5-(1,3-dimethyl-1H-pyrazol-4-yl)-pyridin-2-yl]-ethyl}-3-hydroxy-butyramide
(S)-1-[5-(1-Methyl-1H-pyrazol-4-yl)-pyridin-2-yl]-ethylamine
[6'-((R)-1-Amino-ethyl)-[3,3']bipyridinyl-6-yl]-methanol
(R)-1-[5-(1H-Pyrazol-4-yl)-pyridin-2-yl]-ethylamine
(R)-1-[5-(1,3-Dimethyl-1H-pyrazol-4-yl)-pyridin-2-yl]-ethylamine 1-(5-1,2,4-Triazol-1-yl-pyridin-2-yl)-cyclopropylamine bistrifluoroacetic acid salt

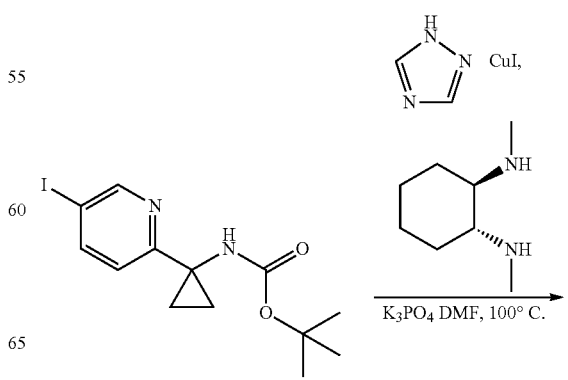

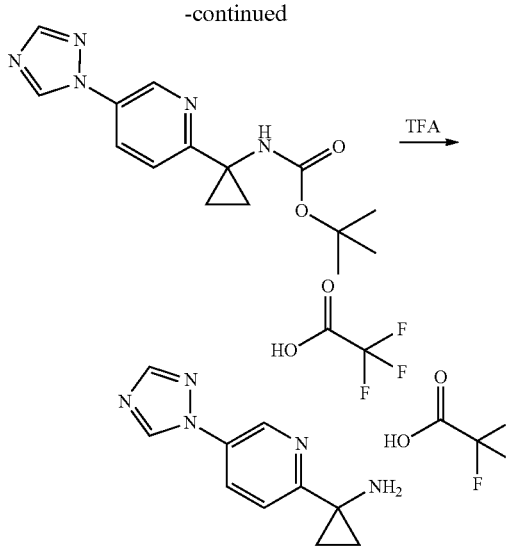

[1-(5-Iodo-pyridin-2-yl)-cyclopropyl]-carbamic acid tert-butyl ester (100 mg, 0.28 mmol), CuI (11 mg, 0.06 mmol), 1,2,4-triazole (29 mg, 0.42 mmol) and K$_3$PO$_4$ (118 mg, 0.556 mmol) were mixed in a 8-mL microwave vial. (1R,2R)-N,N'-dimethyl-cyclohexane-1,2-diamine (18 µL, 0.11 mmol) was added to the mixture under argon followed by DMF (2 mL). The reaction was heated at 100° C. overnight. The reaction was then cooled to room temperature and diluted with water (50 mL) and EtOAc (50 mL). The organic layer was collected and dried over MgSO$_4$. The residue was purified by flash chromatography on silica gel (20% EtOAc/Hex to 100% EtOAc) to give [1-(5-[1,2,4]triazol-1-yl-pyridin-2-yl)-cyclopropyl]-carbamic acid tert-butyl ester (40 mg, 0.13 mmol, 48%) as a semi-solid.

[1-(5-[1,2,4]Triazol-1-yl-pyridin-2-yl)-cyclopropyl]-carbamic acid tert-butyl ester (40 mg, 0.13 mmol) was dissolved in CH$_2$Cl$_2$ (0.6 mL) and then TFA (0.1 mL) was added. After 18 h, the reaction solution was concentrated in-vacuo to yield 27 mg of crude 1-(5-1,2,4-triazol-1-yl-pyridin-2-yl)-cyclopropylamine bistrifluoroacetic acid salt. The material was used in subsequent reactions without further purifications.

The following compounds were prepared using procedures similar to those described above:
1-(5-Pyrazol-1-yl-pyridin-2-yl)-cyclopropylamine bistrifluoroacetic acid salt
1-(5-Imidazol-1-yl-pyridin-2-yl)-cyclopropylamine bistrifluoroacetic acid salt
6'-(1-Amino-cyclopropyl)-[1,3']bipyridinyl-2-one bistrifluoroacetic acid salt General Procedure—Amidine Formation 3,N-Dihydroxy-butyramidine

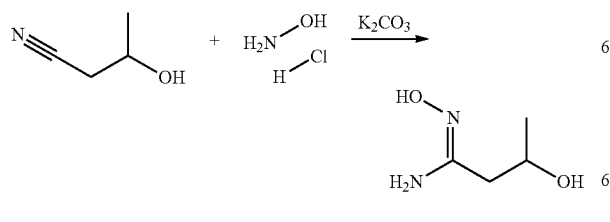

To a slurry of 3-hydroxybutyronitrile (1.00 g, 11.8 mmol) and K$_2$CO$_3$ (3.25 g, 23.5 mmol) in 15 mL of EtOH was added hydroxylamine hydrochloride (1.63 g, 23.5 mmol). The reaction mixture was stirred at reflux for 20 h and then cooled to room temperature and filtered, washing with 40 mL of EtOH. The filtrates were concentrated to an oily white solid that was treated with 30 mL of EtOH. The precipitate was filtered, washing with 30 mL of EtOH, and the filtrates were concentrated to a yellow, oily solid. The crude product was triturated with 30 mL of 10% MeOH/dichloromethane and filtered, washing with 10 mL of 10% MeOH/dichloromethane. The filtrates were concentrated to give 1.32 g of the product as a pale yellow oil.

The following compound was prepared using similar procedures as described above:
N-Hydroxy-1-methyl-1H-pyrazole-4-carboxamidine General Procedure—[1,2,4]oxadiazol-5-yl)-cyclopropylamine formation: -1-(3-Methyl-[1,2,4]oxadiazol-5-yl)-cyclopropylamine hydrochloride

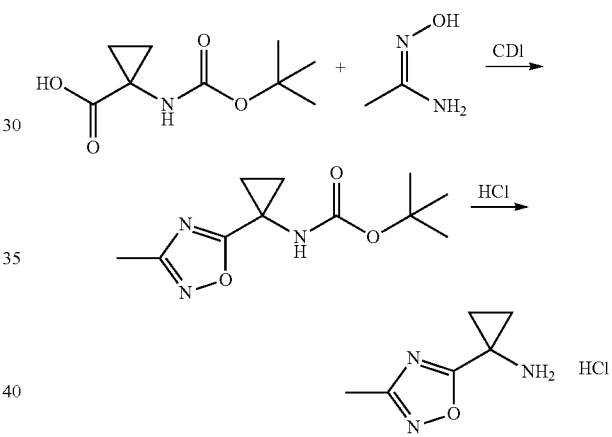

To a solution of N-boc-amino-cyclopropanecarboxylic acid (1.01 g, 5.00 mmol) in 2 mL of DMF was added carbonyldiimidazole (0.812 g, 5.01 mmol). This reaction mixture was stirred at room temperature for 6 h. N-Hydroxy-acetamidine (0.374 g, 5.05 mmol) was added. This reaction mixture was stirred at room temperature for 2 h then heated at 100° C. for 16 h. After cooling to room temperature, the reaction mixture was diluted with water. The resultant precipitate was collected by filtration, washed with acetonitrile and water and air-dried to give 1.05 g of [1-(3-methyl-1,2,4-oxadiazol-5-yl)-cyclopropyl]-carbamic acid tert-butyl ester as a white solid, m/z 240 [M+1]$^+$.

[1-(3-Methyl-1,2,4-oxadiazol-5-yl)-cyclopropyl]-carbamic acid tert-butyl ester (80 mg, 0.33 mmol) was dissolved in HCl in 1,4-dioxane (4.0M, 1.0 mL, 4.0 mmol). After standing at room temperature for 1 h, the solvent was removed by a stream of nitrogen. The title compound was isolated and used without further purification.

The following compound was prepared using similar procedures as described above:
1-[3-(1-Methyl-1H-pyrazol-4-yl)-1,2,4-oxadiazol-5-yl]-cyclopropylamine 1-[5-(3-Cyclopropyl-1,2,4-oxadiazol-5-yl)-pyridin-2-yl]-cyclopropylamine bistrifluoroacetic acid salt

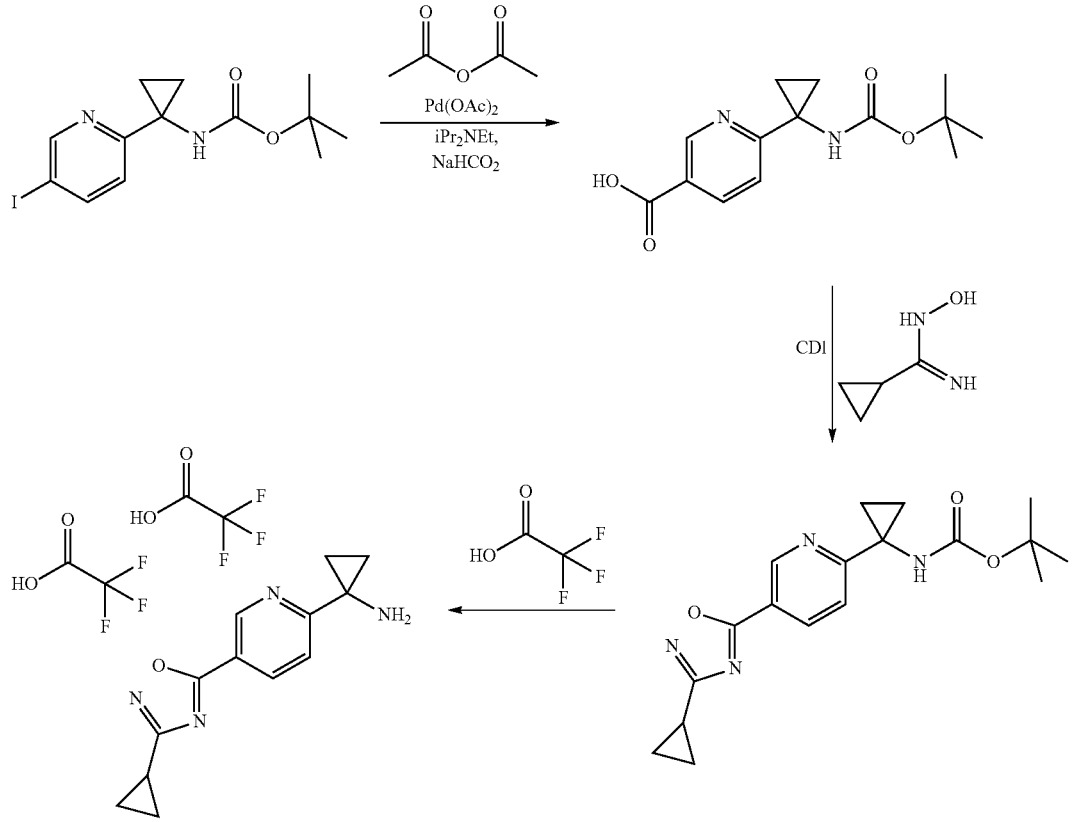

To a solution of acid anhydride (0.89 mL, 9.4 mmol) in DMF (10 mL) in a pressure tube was added sodium formate (0.96 g, 14.2 mmol) and Hunig's base (1.6 mL, 9.4 mmol). The pressure tube was sealed and the mixture allowed to stir at room temperature for 45 minutes. The tube was opened and a solution of [1-(5-iodo-pyridin-2-yl)-cyclopropyl]-carbamic acid tert-butyl ester (1.7 g, 4.7 mmol) in DMF (3 mL) was added followed by LiCl (0.60 g, 14.2 mmol) and Pd(OAc)$_2$ (0.11 g, 0.47 mmol). The reaction vessel was sealed and the mixture heated at 80° C. for 20 h. The reaction mixture was cooled to room temperature and the cap slowly removed allowing for gas release. The mixture was diluted with water and extracted with EtOAc (3×100 mL). The combined extracts were washed with water, 1N HCl, brine and dried with MgSO$_4$. The mixture was filtered and concentrated to give 6-(1-tert-butoxycarbonylamino-cyclopropyl)-nicotinic acid (0.51 g, 1.8 mmol) as a yellow solid, m/z 279.6.

To a solution of 6-(1-tert-butoxycarbonylamino-cyclopropyl)-nicotinic acid (0.10 g, 0.10 mmol) in DMF (5 mL) was added CDI (0.16 g, 0.10 mmol). The mixture was stirred at room temperature for 3 h. N-hydroxy-cyclopropanecarboxamidine (0.28 g, 0.10 mmol) was then added and the reaction mixture heated at 100° C. for 24 h. The mixture was cooled to room temperature, diluted with water and extracted with EtOAc (3×100 mL). The combined extracts were washed with water, satd aqueous NaHCO$_3$, brine and dried with MgSO$_4$. The mixture was filtered and concentrated to give {1-[5-(3-cyclopropyl-1,2,4-oxadiazol-5-yl)-pyridin-2-yl]-cyclopropyl}-carbamic acid tert-butyl ester (0.13 g, 0.38 mmol) as a yellow oil, m/z 343.7 [M+H]$^+$.

To a solution of {1-[5-(3-cyclopropyl-1,2,4-oxadiazol-5-yl)-pyridin-2-yl]-cyclopropyl}-carbamic acid tert-butyl ester (0.13 g, 0.38 mmol) in CH$_2$Cl$_2$ (1 mL) was added TFA (1 mL). The reaction was allowed to stir at room temperature for 2 h. The solvent and excess TFA were removed under reduced pressure to give the title compound (0.14 g, 0.41 mmol), m/z 243.6 [M+H]$^+$.

1-[5-(5-Cyclopropyl-1,3,4-oxadiazol-2-yl)-pyridin-2-yl]-cyclopropylamine bistrifluoroacetic acid salt

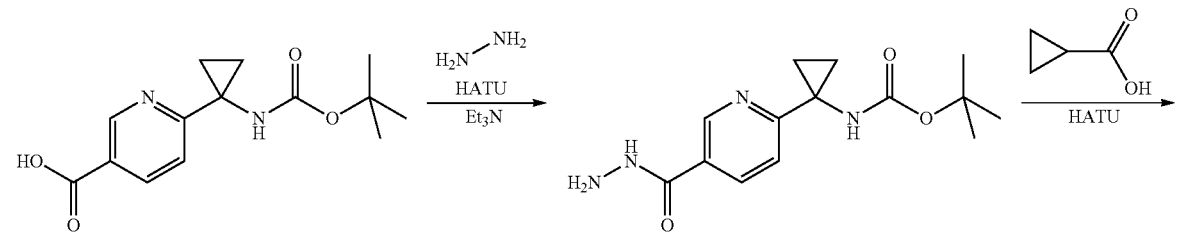

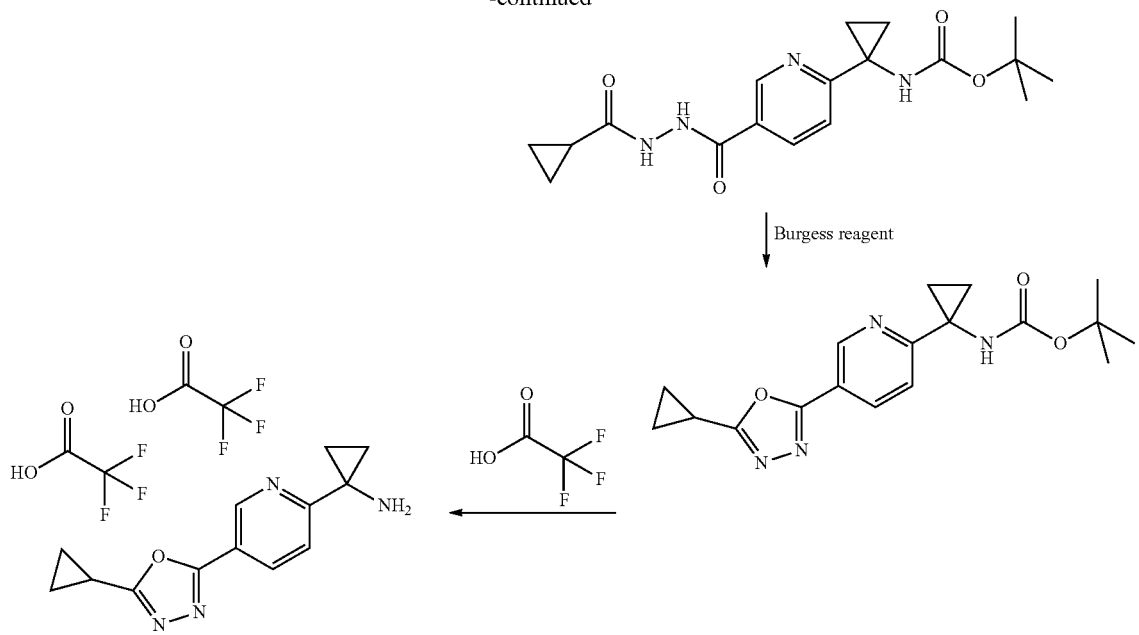

To a solution of 6-(1-tert-butoxycarbonylamino-cyclopropyl)-nicotinic acid (0.50 g, 1.8 mmol) in DMF (3 mL) was added HATU (0.68 g, 1.8 mmol), Et₃N (0.25 mL, 1.8 mmol) and the mixture allowed to stir at room temperature for 20 min. Hydrazine monohydrate (0.09 mL, 1.8 mmol) was then added and the reaction stirred for 1 h. The mixture was diluted with water and extracted with EtOAc (3×100 mL). The combined extracts were washed with water, brine and dried with MgSO₄. The mixture was filtered and concentrated to give [1-(5-hydrazinocarbonyl-pyridin-2-yl)-cyclopropyl]-carbamic acid tert-butyl ester (0.51 g, 1.7 mmol) as a yellow solid, m/z 293.7 [M+H]⁺.

To a solution of cyclopropyl carboxylic acid (0.20 g, 0.68 mmol) in DMF (2 mL) was added HATU (0.26 g, 0.68 mmol), Et₃N (0.10 mL, 0.75 mmol) and the reaction mixture was allowed to stir at room temperature for 20 min. [1-(5-Hydrazinocarbonyl-pyridin-2-yl)-cyclopropyl]-carbamic acid tert-butyl ester (0.20 g, 0.68 mmol) in DMF (1 mL) was added and the reaction allowed to stir at room temperature for 21 h. The mixture was diluted with water and extracted with EtOAc (3×100 mL). The combined extracts were washed with satd NaHCO₃, brine and dried with MgSO₄. The mixture was filtered and concentrated to give {1-[5-(N'-cyclopropane-carbonyl-hydrazinocarbonyl)-pyridin-2-yl]-cyclopropyl}-carbamic acid tert-butyl ester (0.23 g, 0.64 mmol) as a light brown solid, m/z 361.7 [M+H]⁺.

1-[5-(N'-Cyclopropanecarbonyl-hydrazinocarbonyl)-pyridin-2-yl]-cyclopropyl}-carbamic acid tert-butyl ester (0.23 g, 0.64 mmol) was dissolved in THF (2 mL) and to this was added Burgess reagent (0.30 g, 1.3 mmol). The mixture was heated at 150° C. in a microwave for 30 min. The mixture was diluted with water and extracted with EtOAc (3×50 mL). The combined extracts were washed with water, brine and dried with MgSO₄. The mixture was filtered, concentrated and the residue purified by reversed phase HPLC (MeCN/H₂O) to give {1-[5-(5-cyclopropyl-1,3,4-oxadiazol-2-yl)-pyridin-2-yl]-cyclopropyl}-carbamic acid tert-butyl ester (0.045 g, 0.13 mmol) as a brown solid, m/z 343.7 [M+H]⁺.

To a solution of {1-[5-(5-cyclopropyl-1,3,4-oxadiazol-2-yl)-pyridin-2-yl]-cyclopropyl}-carbamic acid tert-butyl ester (40 mg, 0.12 mmol) in CH₂Cl₂ (0.2 mL) was added TFA (1 mL). The reaction was allowed to stir at room temperature for 4 h. The solvent and excess TFA were removed under reduced pressure to give the title compound (0.041 g), m/z 243.6 [M+H]⁺.

1-{4-[6-(1-Amino-cyclopropyl)-pyridin-3-yl]-phenyl}-cyclopropanol bistrifluoroacetic acid salt

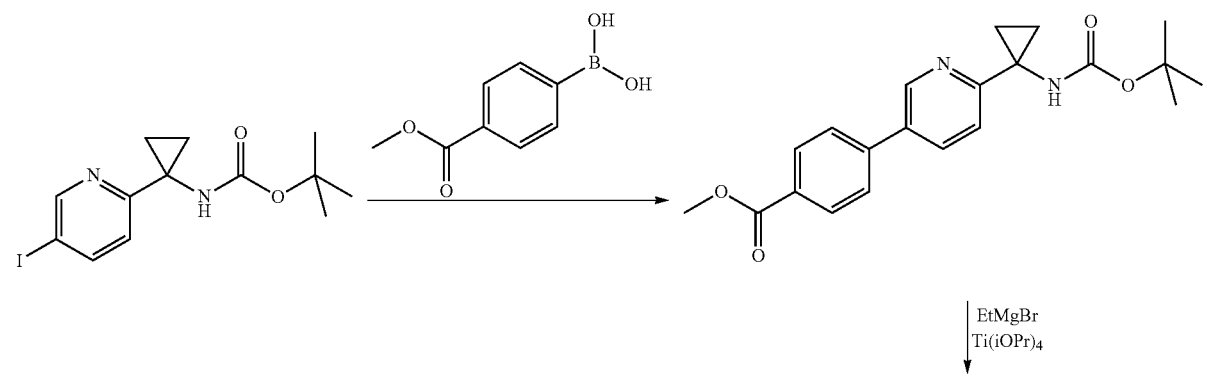

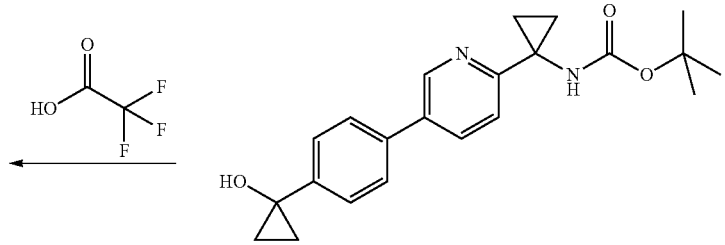

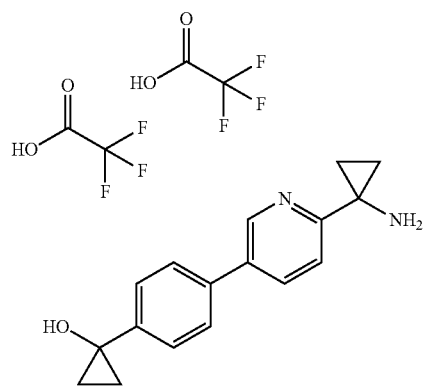

To a solution of [1-(5-iodo-pyridin-2-yl)-cyclopropyl]-carbamic acid tert-butyl ester (1.5 g, 4.2 mmol) in DME (4 mL) was added PdCl₂(dppf).dichloromethane complex (0.34 g, 0.42 mmol). The solution was transferred to a microwave vial containing (4-methoxy-carbonylphenyl)-boronic acid (0.90 g, 5.0 mmol). K₃PO₄ (1.1 g, 5.4 mmol) was then added followed by water (1 mL) and EtOH (1 mL). The reaction was heated in a microwave at 100° C. for 10 min. The mixture was diluted with water and extracted with EtOAc (3×50 mL). The combined extracts were washed with water, brine and dried with MgSO₄. The mixture was filtered, concentrated and the residue purified by silica gel chromatography (0-100% EtOAc in hexanes) to give 4-[6-(1-tert-butoxycarbonylamino-cyclopropyl)-pyridin-3-yl]-benzoic acid methyl ester (0.75 g, 2.0 mmol) as a yellow solid, m/z 369.7 [M+H]⁺.

To a solution of 4-[6-(1-tert-butoxycarbonylamino-cyclopropyl)-pyridin-3-yl]-benzoic acid methyl ester (0.68 g, 1.8 mmol) in THF (20 mL) was added Ti(Oi-Pr)₄ (0.54 mL, 1.8 mmol). To this mixture was slowly added EtMgBr (3M in Et₂O, 1.2 mL, 3.7 mmol) over 30 minutes. The reaction was allowed to stir at room temperature for 1 h. Ti(Oi-Pr)₄ (1.1 mL, 3.2 mmol) and EtMgBr (3M in Et₂O, 1.2 mL, 3.7 mmol) were again added to the solution and the reaction stirred for 30 minutes. The mixture was quenched with water and extracted with EtOAc (3×100 mL). The combined extracts were washed with water, brine and dried with MgSO₄. The mixture was filtered, concentrated and the residue purified by reverse phase HPLC to give (1-{5-[4-(1-hydroxy-cyclopropyl)-phenyl]-pyridin-2-yl}-cyclopropyl)-carbamic acid tert-butyl ester (0.05 g, 1.4 mmol) as a brown solid, m/z 367.7 [M+H]⁺.

To a solution of (1-{5-[4-(1-hydroxy-cyclopropyl)-phenyl]-pyridin-2-yl}-cyclopropyl)-carbamic acid tert-butyl ester (50 mg, 0.14 mmol) in CH₂Cl₂ (1 mL) was added TFA (3 mL). The reaction was allowed to stir at room temperature for 1 h. The solvent and excess TFA were removed under reduced pressure to give the title compound (50 mg, 0.14 mmol), m/z 267.6 [M+H]⁺.

6'-(1-Amino-cyclopropyl)-1H-[3,3']bipyridinyl-6-one bistrifluoroacetic acid salt

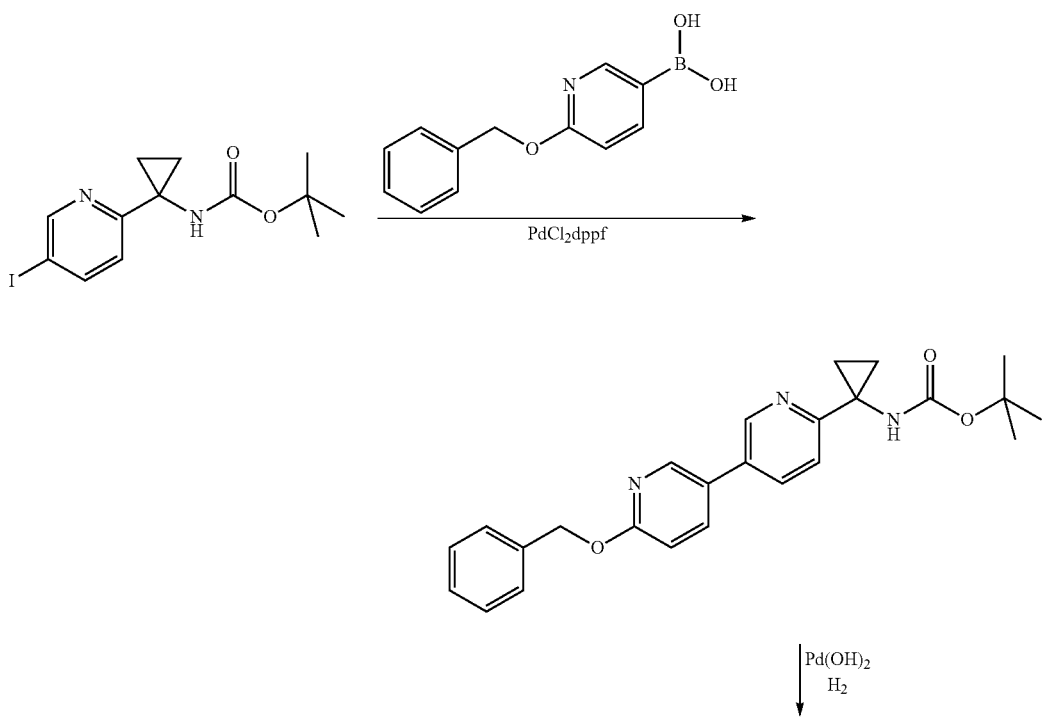

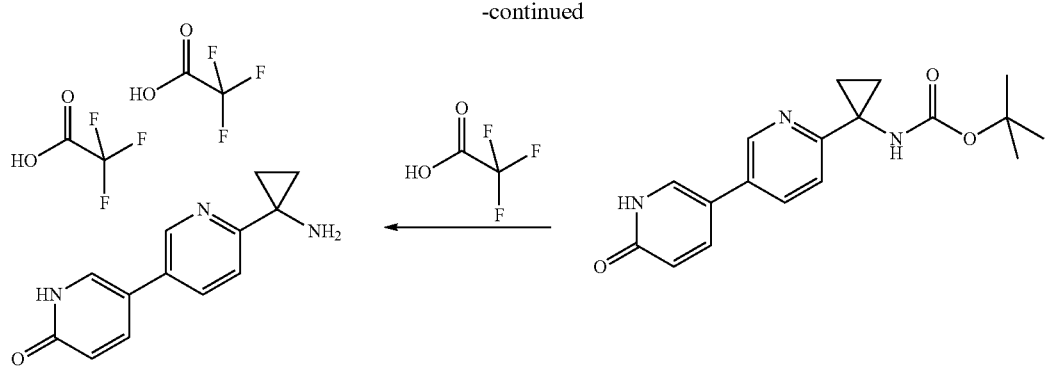

To a solution of [1-(5-iodo-pyridin-2-yl)-cyclopropyl]-carbamic acid tert-butyl ester (0.25 g, 0.69 mmol) in DME (1 mL) was added PdCl₂(dppf).dichloromethane complex (57 mg, 0.07 mmol). This solution was transferred to a microwave vial containing 2-benzyloxypyridine-5-boronic acid (0.17 g, 0.76 mmol) and K₃PO₄ (1M, 0.90 mL, 0.90 mmol). Water (0.4 mL) and EtOH (0.3 mL) were added and the mixture heated in a microwave at 100° C. for 10 minutes. The mixture was diluted with water and extracted with EtOAc (3×50 mL). The combined extracts were washed with water, brine and dried with MgSO₄. The mixture was filtered and concentrated to give [1-(6'-benzyloxy-[3,3']bipyridinyl-6-yl)-cyclopropyl]-carbamic acid tert-butyl ester (0.24 g, 0.58 mmol) as a brown solid, m/z 418.8 [M+H]⁺.

To a solution of [1-(6'-benzyloxy-[3,3']bipyridinyl-6-yl)-cyclopropyl]-carbamic acid tert-butyl ester (0.20 g, 0.48 mmol) in MeOH (10 mL) was added Pd(OH)₂ (0.2 g). The flask was purged with H₂ gas and then H₂ gas passed over the solution for 4 h. The mixture was filtered through diatomaceous earth and the filtrate was concentrated under reduced pressure to give [1-(6'-oxo-1',6'-dihydro-[3,3']bipyridinyl-6-yl)-cyclopropyl]-carbamic acid tert-butyl ester (0.16 g, 0.50 mmol), m/z 328.8 [M+H]⁺.

To a solution of [1-(6'-oxo-1',6'-dihydro-[3,3']bipyridinyl-6-yl)-cyclopropyl]-carbamic acid tert-butyl ester (0.15 g, 0.44 mmol) in CH₂Cl₂ (1 mL) was added TFA (1 mL) and the mixture allowed to stir at room temperature for 3 h. The solvent and excess TFA were removed under reduced pressure to give the title compound (0.23 g, 0.50 mmol).

[1-(6-Iodo-[1,8]naphthyridin-2-yl)-cyclobutyl]-carbamic acid tert-butyl ester

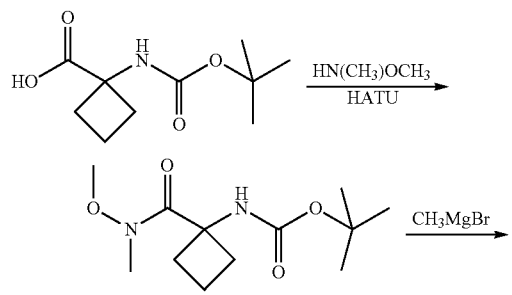

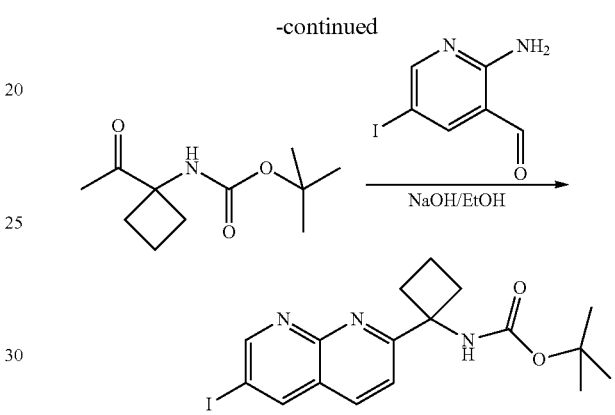

Boc-1-aminocyclobutane-1-carboxylic acid (10.0 g, 45.1 mmol), HATU (20.5 g, 54.1 mmol) and N,O-dimethylhydroxylamine hydrochloride (4.93 g, 49.6 mmol) were combined in DMF (100 mL). To this solution was added diisopropylethylamine (31.4 mL, 180.3 mmol). The reaction was stirred for 2 h, diluted with EtOAc and poured into H₂O. The aqueous phase was separated and extracted two more times with EtOAc. The organic layers were combined and washed with brine, dried (Na₂SO₄), decanted and concentrated in vacuo. The resultant solid was purified via normal phase flash chromatography on silica gel (10-50% EtOAc-heptane) to afford [1-(methoxy-methyl-carbamoyl)-cyclobutyl]-carbamic acid tert-butyl ester as a white solid (11.5 g, 99%).

To a solution of [1-(methoxy-methyl-carbamoyl)-cyclobutyl]-carbamic acid tert-butyl ester (11.5 g, 44.6 mmol) in THF (150 mL) at 0° C. was slowly added methylmagnesium bromide as a 3.0M solution in ether (37.2 mL, 111 mmol). The reaction was allowed to slowly warm to 25° C. and stirred for 24 h then quenched by the addition of saturated aqueous NH₄Cl (100 mL). EtOAc (200 mL) was added and the layers were separated. The aqueous phase was extracted two more times with EtOAc. The organic layers were combined, washed with brine, dried (Na₂SO₄), decanted and concentrated to afford a solid. The solid was purified via normal phase flash chromatography on silica gel (10-50% EtOAc-heptane) to afford (1-acetyl-cyclobutyl)-carbamic acid tert-butyl ester as a white solid (6.02 g, 63%).

Freshly ground NaOH (0.32 g, 7.9 mmol) was dissolved in absolute EtOH (25 mL). To this solution was added (1-acetyl-cyclobutyl)-carbamic acid tert-butyl ester (0.84 g, 3.95 mmol) and 5-iodo-2-aminopyridine-3-carboxaldehyde (0.932 g, 3.76 mmol) simultaneously as a solution in EtOH (25 mL). The reaction was allowed to stir for 72 h and the volatiles were removed in vacuo. This crude residue was diluted with CH$_2$Cl$_2$, absorbed onto SiO$_2$ by removal of solvent in vacuo and purified via SiO$_2$ flash chromatography (20-75% EtOAc-hexane) to afford the title compound as a white solid (1.34 g, 84%), m/z=366.4.

3,5-Dichloro-4-fluoro-phenylamine

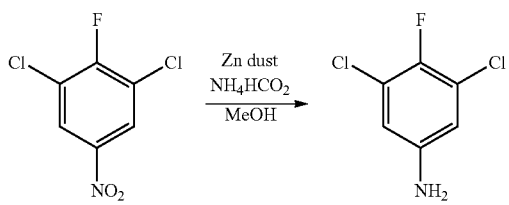 [SMILES: "MeOH" ; O=[N+]([O-])c1cc(Cl)c(F)c(Cl)c1 ; Nc1cc(Cl)c(F)c(Cl)c1]

To a solution of 1,3-dichloro-2-fluoro-5-nitro-benzene (71.4 g, 340 mmol) in methanol (1.5 L) was added a solution of ammonium formate (180.2 g, 2.86 mol) in water (300 mL). Zinc dust (93.4 g, 1.43 mol) was then added in four equal portions over 20 min. The reaction was stirred for 1 h and then allowed to cool to room temperature. The reaction mixture was filtered through diatomaceous earth and the filtrate was concentrated in vacuo. Ethyl acetate (300 mL) and water (300 mL) were added and the mixture was again filtered through diatomaceous earth. The layers were separated, and the aqueous layer was further extracted with ethyl acetate (350 mL). The combined organics were washed with 500 mL of brine, dried over Na$_2$SO$_4$, filtered, and concentrated to afford 56.4 g of the title compound as a brown solid, m/z 180.2 [M+H]$^+$. This material was used without any further purification.

[(R)-1-(3,5-Dichloro-4-fluoro-phenylcarbamoyl)-ethyl]-carbamic acid tert-butyl ester

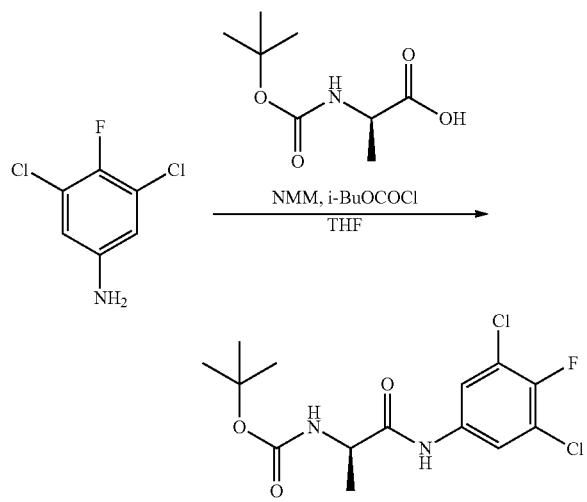

To a cooled (−20° C.) solution of (R)-2-tert-butoxycarbonylamino-propionic acid (57.2 g, 302 mmol) in anhydrous THF (582 mL) was added N-methyl-morpholine (34.9 mL, 317 mmol) at a rate to keep the internal temperature at −15° C. Isobutyl chloroformate (42.0 mL, 317 mmol) was then added over a 20 min period and the resulting mixture was stirred for 30 min. A solution of 3,5-dichloro-4-fluoro-phenylamine (54.4 g, 302 mmol) in THF (160 mL) was then added over 40 min. The reaction mixture was warmed to 20° C. and stirred for 20 h. The reaction mixture was filtered and concentrated in vacuo. To the resulting oil was added MeOH (200 mL) and the solution was concentrated to provide the title compound as a tan colored solid, m/z 295.3 [M-t-Bu]$^+$. This material was used without further purification.

The following compound was prepared using similar procedures as described above:
[(R)-1-(3-Chloro-5-trifluoromethyl-phenylcarbamoyl)-ethyl]-carbamic acid tert-butyl ester

(R)-2-Amino-N-(3,5-dichloro-4-fluoro-phenyl)-propionamide

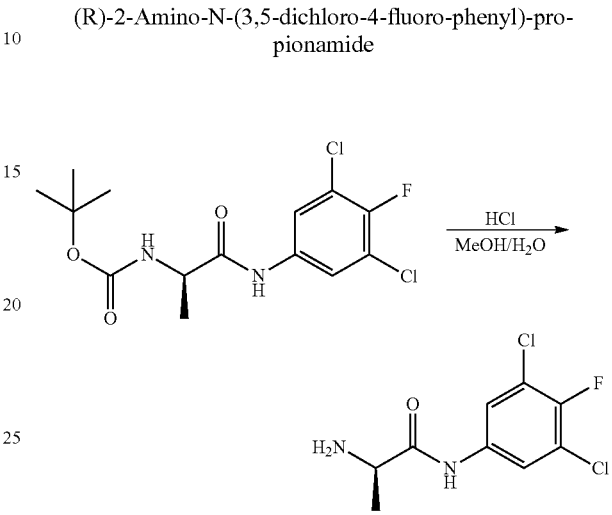

To a solution of hydrochloric acid (12M, 266 mL, 3.19 mol) in water (272 mL) and MeOH (135 mL) was added a solution of crude [(R)-1-(3,5-dichloro-4-fluoro-phenylcarbamoyl)-ethyl]-carbamic acid tert-butyl ester (208.6 g, 594 mmol) in MeOH (600 mL) via an addition funnel over 30 min. CH$_2$Cl$_2$ (300 mL) was then added and the reaction mixture was stirred at room temperature overnight. An additional portion of HCl (12M, 100 mL) was added and stirring was continued for another 20 h. The volatile solvents were removed in vacuo and the remaining aqueous mixture was cooled to −15 to −20° C. Toluene (400 mL) was added followed by the addition of NaOH solution (50% aqueous, 300 mL), which was added at a rate to keep the internal temperature below 25° C. The layers were separated and the aqueous layer was extracted with toluene (2×1 L). The combined organic layers were dried with Na$_2$SO$_4$ and concentrated to give 158.3 g of the title compound as a dark brown oil that solidifies slowly in the freezer, m/z 251.1 [M+H]$^+$. This crude material was used without further purification.

The following compound was prepared using similar procedures as described above:
(R)-2-Amino-N-(3-chloro-5-trifluoromethyl-phenyl)-propionamide

(2S,5R)-2-tert-Butyl-3-(3,5-dichloro-4-fluoro-phenyl)-5-methyl-1-(2,2,2-trifluoro-acetyl)-imidazolidin-4-one

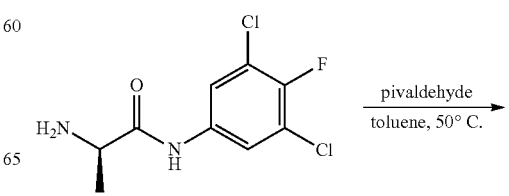

121

-continued

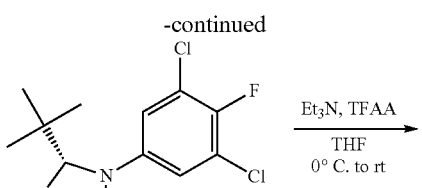

122

4-[(2R,4R)-2-tert-Butyl-1-(3,5-dichloro-4-fluoro-phenyl)-4-methyl-5-oxo-3-(2,2,2-trifluoro-acetyl)-imidazolidin-4-ylmethyl]-benzonitrile

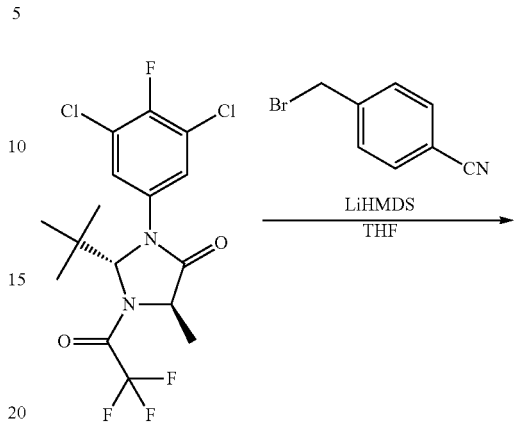

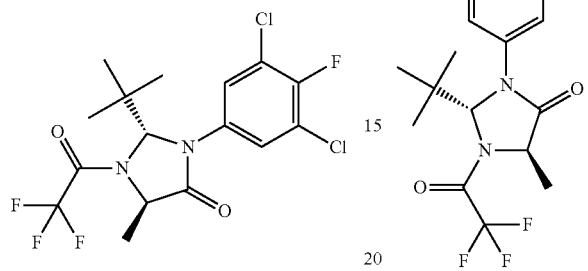

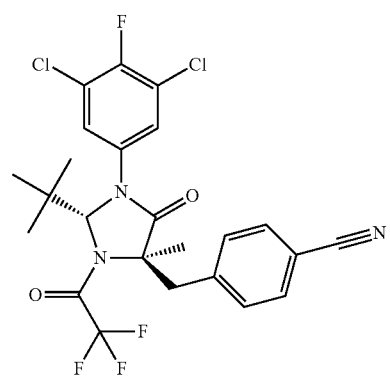

To a solution of (R)-2-amino-N-(3,5-dichloro-4-fluoro-phenyl)-propionamide (149.1 g crude, max 594 mmol) in toluene (743 mL) at 40° C., was added pivalaldehyde (67.1 mL, 618 mmol) in one portion. The reaction was stirred at 50° C. for 22 h and then all volatiles were removed in vacuo to give a viscous brown oil. Hexane (500 mL) was added and the resulting suspension was stirred at room temperature for 30 min. The mixture was filtered and the solids rinsed with cold hexane. The filtrate was concentrated in vacuo and reprocessed in a similar manner to obtain additional precipitate. The remaining filtrate was diluted with hexane until a black oil separated from the solution. The hexane layer was decanted from this black oil and concentrated in vacuo. The residue was re-dissolved in warm diethyl ether (300 mL) and stored in the freezer for 1.5 h over which time crystal growth was observed. The solids were filtered, and the filtrate reprocessed in a similar manner to obtain additional crystals. All of the collected solids were combined to give 112.2 g of (2S,5R)-2-tert-butyl-3-(3,5-dichloro-4-fluoro-phenyl)-5-methyl-imidazolidin-4-one as a tan solid. To a solution of this solid in toluene (639 mL) at 0° C. was added triethylamine (73.5 mL, 527 mmol) in one portion. Trifluoroacetic anhydride (58.6 mL, 422 mmol) was added to the reaction mixture over 1 h at a rate to keep the internal temperature below 5° C. The reaction mixture was stirred at 0° C. for 1 h and then warmed to 20° C. over 1 h. The mixture was then cooled to 10° C. and water (1.2 L) was added. The layers were separated and the organic layer was washed with water (1.2 L and then 0.6 L). The combined aqueous layers were extracted with toluene (0.6 L). The combined organic layers were dried over MgSO$_4$ and concentrated in vacuo to give 149.4 g of the title compound as a tan solid, m/z 456.4 [M+MeCN+H]$^+$.

The following compound was prepared using similar procedures as described above:

(2S,5R)-2-tert-Butyl-3-(3-chloro-5-trifluoromethyl-phenyl)-5-methyl-1-(2,2,2-trifluoro-acetyl)-imidazolidin-4-one To a solution of (2S,5R)-2-tert-butyl-3-(3,5-dichloro-4-fluoro-phenyl)-5-methyl-1-(2,2,2-trifluoro-acetyl)-imidazolidin-4-one (158.4 g, 0.382 mol) in anhydrous THF (382 mL) under a nitrogen atmosphere at −20° C. was added a solution of LiHMDS (1.0 M in THF, 401 mL, 0.401 mol) over 50 min. The internal temperature increased to −5° C. over the course of this addition. Stirring was continued at this temperature for an additional hour. The reaction was cooled to −10° C. and a solution of 4-cyanobenzyl bromide (78.5 g, 401 mmol) in anhydrous THF (400 mL) was added over 50 min. The reaction temperature had increased to 0° C. over the course of the addition. Stirring was continued for 2 h while the reaction was allowed to warm to 10° C. To the reaction mixture was added saturated aqueous NH$_4$Cl (200 mL), water (800 mL), and EtOAc (1 L). The layers were separated and the aqueous layer was extracted with EtOAc (1 L). The combined organic layers were dried with MgSO$_4$ and concentrated in vacuo to give 214.2 g of the title compound as a tan/brown solid, m/z 571.3 [M+MeCN+H]$^+$.

The following compounds were prepared using similar procedures as described above:

4-[(2S,4R)-3-Acetyl-2-tert-butyl-1-(3-chloro-5-trifluoromethyl-phenyl)-4-methyl-5-oxo-imidazolidin-4-ylmethyl]-benzonitrile (2R,5R)-2-tert-Butyl-3-(3,5-dichloro-4-fluoro-phenyl)-5-methyl-1-(2,2,2-trifluoro-acetyl)-5-(4-trifluoromethoxy-benzyl)-imidazolidin-4-one (R)-2-(4-Cyano-phenyl)-1-(3,5-dichloro-4-fluoro-phenylcarbamoyl)-1-methyl-ethyl-ammonium toluene-4-sulfonate

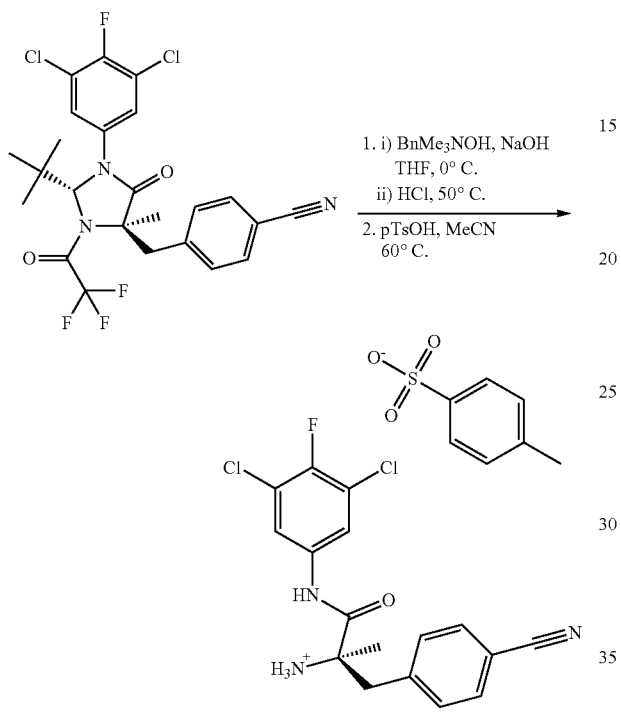

To a solution of 4-[(2R,4R)-2-tert-butyl-1-(3,5-dichloro-4-fluoro-phenyl)-4-methyl-5-oxo-3-(2,2,2-trifluoro-acetyl)-imidazolidin-4-ylmethyl]-benzonitrile (121.3 g, 228.7 mmol) in THF (457 mL) at 0° C. was added an aqueous solution of BnMe₃NOH (40 wt % in water, 135.3 mL, 343.1 mmol) over 30 min followed by aqueous NaOH (50 wt %, 21.5 mL, 407 mmol). Both reagents were added at a rate sufficient to keep the internal temperature at 0° C. The reaction mixture was stirred at this temperature for 6.5 h. HCl solution (6N, 234 mL, 1.40 mol) was then added to the reaction mixture at a rate sufficient to keep the internal temperature below 15° C. The reaction was heated to 50° C. and stirred at this temperature for 1.5 h. A portion of the solvent (~350 mL) was removed in vacuo and CH₂Cl₂ (300 mL) was added. The mixture was cooled in an ice bath and a NaOH solution (2N) was added at a rate to keep the internal temperature below 20° C. until the pH of aqueous layer reached 14. The mixture was transferred to a separatory funnel using CH₂Cl₂ and H₂O to ensure the transfer all of the solid material. The layers were separated and the aqueous layer was extracted with CH₂Cl₂ (2×500 mL). The combined organic layers were washed once with brine (300 mL), dried with Na₂SO₄, and concentrated in vacuo to give 83.8 g of a red/black viscous oil. This material was dissolved in MeCN (600 mL) and heated to 60° C. with stirring. p-Toluenesulfonic acid monohydrate (50.1 g, 263 mmol) was added to the solution causing a precipitate to form. Additional MeCN (200 mL) was added and mixture was filtered to collect the solids. The filter cake washed with 600 mL of MeCN and dried to give 106 g of the title compound as a white solid, m/z 366.6 [M]⁺.

The following compounds were prepared using similar procedures as described above:

(R)-1-(3-Chloro-5-trifluoromethyl-phenylcarbamoyl)-2-(4-cyano-phenyl)-1-methyl-ethyl-ammonium toluene-4-sulfonate salt (R)-1-(3,5-Dichloro-4-fluoro-phenylcarbamoyl)-1-methyl-2-(4-trifluoromethoxy-phenyl)-ethyl-ammonium toluene-4-sulfonate salt (R)-3-(4-Cyano-phenyl)-N-(3,5-dichloro-4-fluoro-phenyl)-2-[3-(2,2-dimethoxy-ethyl)-ureido]-2-methyl-propionamide

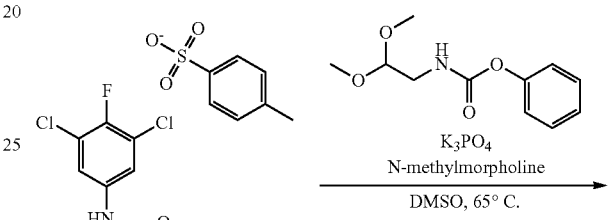

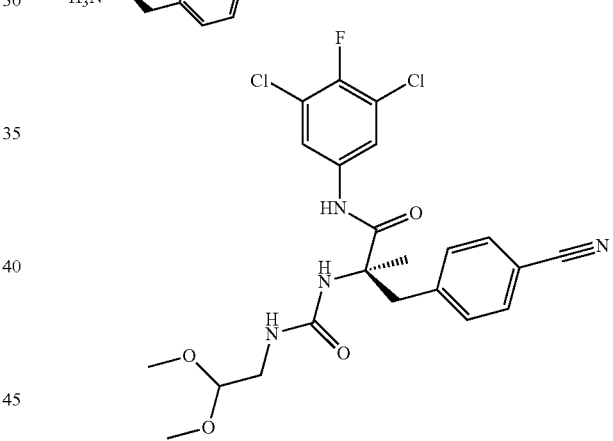

To a solution of (R)-2-(4-cyano-phenyl)-1-(3,5-dichloro-4-fluoro-phenylcarbamoyl)-1-methyl-ethyl-ammonium toluene-4-sulfonate (87.7 g, 162.9 mmol) and (2,2-dimethoxy-ethyl)-carbamic acid phenyl ester (40.4 g, 179 mmol) in DMSO (162 mL) was added Na₃PO₄ (29.4 g, 179 mmol) and N-methylmorpholine (3.04 mL, 27.7 mmol). The solution was heated to 65° C. and stirred for 6 h. The solution was cooled to 20° C. and transferred to a separatory funnel with aqueous Na₂CO₃ (3 wt %, 500 mL) and EtOAc (500 mL), forming a triphasic system after shaking. The bottom two layers were removed. The top organic layer was washed with 3% aqueous NaCl (500 mL), dried with Na₂SO₄ and concentrated in vacuo keeping internal temperature lower than 40° C. A mixture of heptane and EtOAc (10:1 heptane:EtOAc, 20 mL) was added and the resulting slurry was stirred at 22° C. for 16 h. The slurry was filtered and the solids were washed with a 10:1 mixture of heptane/EtOAc (2×100 mL) to give 61.6 g of the title compound as a white solid, m/z 497.7 [M+H]⁺.

The following compounds were prepared using similar procedures as described above:

(R)-N-(3-Chloro-5-trifluoromethyl-phenyl)-3-(4-cyano-phenyl)-2-[3-(2,2-dimethoxy-ethyl)-ureido]-2-methyl-propionamide (R)-N-(3,5-Dichloro-4-fluoro-phenyl)-2-[3-(2,2-dimethoxy-ethyl)-ureido]-2-methyl-3-(4-trifluoromethoxy-phenyl)-propionamide 4-[(R)-1-(3,5-Dichloro-4-fluoro-phenyl)-3-methyl-2-oxo-2,3-dihydro-1H-imidazo[1,2-a]imidazol-3-ylmethyl]-benzonitrile

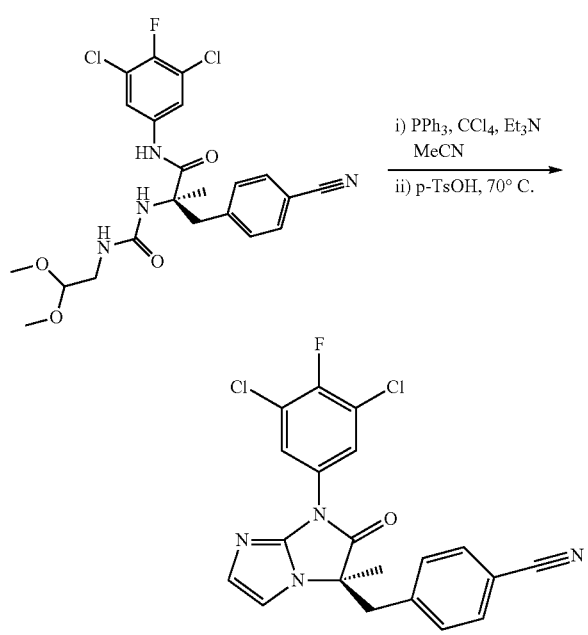

To a room temperature suspension of (R)-3-(4-cyano-phenyl)-N-(3,5-dichloro-4-fluoro-phenyl)-2-[3-(2,2-dimethoxy-ethyl)-ureido]-2-methyl-propionamide (62.6 g, 125.9 mmol), PPh$_3$ (51.98 g, 198.17 mmol), and Et$_3$N (29.35 mL, 210.6 mmol) in MeCN (250 mL) was added CCl$_4$ (20.3 mL, 210.6 mmol) in one portion. The reaction was stirred for 2 h and then cooled to 0° C. To this solution was added p-toluenesulfonic acid monohydrate (37.7 g, 198.2 mmol) and the reaction was heated at 70° C. for 2 h. The volatiles were evaporated in vacuo, and the residue was diluted with isopropyl acetate (i-PrOAc) (500 mL) and water (500 mL). The water layer was removed and the organic layer was washed with aqueous Na$_2$CO$_3$ (5 wt %, 500 mL) and then aqueous NaCl (3 wt %, 500 mL). The organic layer was dried over Na$_2$SO$_4$ and concentrated in vacuo to give a semi-solid. A mixture of Heptane/i-PrOAc (150 mL, 80:20 heptane:i-PrOAc) was added causing precipitation of a solid. The resulting slurry was stirred overnight and then filtered. The filtrate was evaporated in vacuo to give a brown oil. The oil was re-processed using the same conditions 3 more times. The remaining brown oil from the filtrate was then purified by flash chromatography on silica gel (20-50% EtOAc/hexanes) to give 48.0 g of the title compounds as a white solid, m/z 415.7 [M+H]$^+$.

The following compounds were prepared using similar procedures as described above:

4-[(R)-1-(3-Chloro-5-trifluoromethyl-phenyl)-3-methyl-2-oxo-2,3-dihydro-1H-imidazo[1,2-a]imidazol-3-ylmethyl]-benzonitrile (R)-1-(3,5-Dichloro-4-fluoro-phenyl)-3-methyl-3-(4-trifluoromethoxy-benzyl)-1H-imidazo[1,2-a]imidazol-2-one 4-[(R)-1-(3,5-Dichloro-4-fluoro-phenyl)-5-iodo-3-methyl-2-oxo-2,3-dihydro-1H-imidazo[1,2-a]imidazol-3-ylmethyl]-benzonitrile

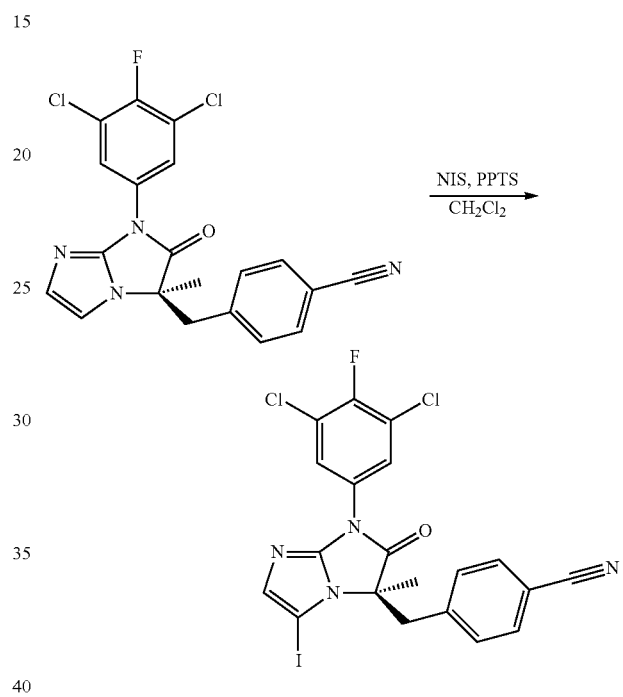

An aluminum foil covered flask containing a solution of 4-[(R)-1-(3,5-dichloro-4-fluoro-phenyl)-3-methyl-2-oxo-2,3-dihydro-1H-imidazo[1,2-a]imidazol-3-ylmethyl]-benzonitrile (48.8 g, 117.5 mmol) in CH$_2$Cl$_2$ (900 mL) was partially submerged in an ice water bath. To this solution was added a solid mixture of N-iodosuccinimide (29.1 g, 129 mmol) and pyridinium p-toluenesulfonate (2.95 g, 11.7 mmol) in four separate portions over a 30 min period. The reaction was allowed to stir in the thawing ice bath for 1 h and then the bath was removed. Stirring was continued overnight. Saturated aqueous Na$_2$S$_2$O$_3$ (300 mL) was added to the reaction and the mixture was transferred to a separatory funnel using CH$_2$Cl$_2$ (200 mL) and water (1 L). The layers were separated and the aqueous layer was further extracted with CH$_2$Cl$_2$ (2×500 mL) and EtOAc (500 mL). The combined organic layers were dried over MgSO$_4$ and concentrated in-vacuo to give a yellow oil. This oil was purified by flash chromatography on silica gel (0-2.5% EtOAc/toluene) to give 52 g of the title compound as a white solid, m/z 541.3 [M+H]$^+$.

The following compounds were prepared using similar procedures as described above:

4-[(R)-1-(3-Chloro-5-trifluoromethyl-phenyl)-5-iodo-3-methyl-2-oxo-2,3-dihydro-1H-imidazo[1,2-a]imidazol-3-ylmethyl]-benzonitrile (R)-1-(3,5-Dichloro-4-fluoro-phenyl)-5-iodo-3-methyl-3-(4-trifluoromethoxy-benzyl)-1H-imidazo[1,2-a]imidazol-2-one (R)-5-(4-Cyano-benzyl)-7-(3,5-dichloro-4-fluoro-phenyl)-5-methyl-6-oxo-6,7-dihydro-5H-imidazo[1,2-a]imidazole-3-carboxylic acid

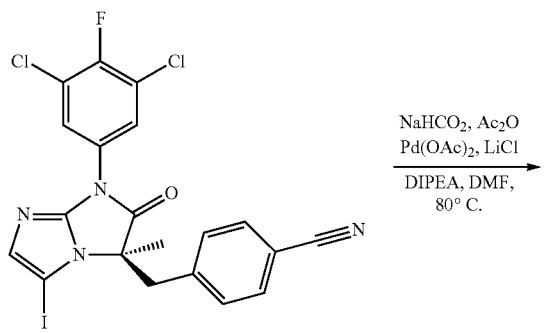

Acetic anhydride (14.0 mL, 148 mmol), sodium formate (15.1 g, 222 mmol) and Hunig's base (25.8 mL, 148 mmol) were suspended in anhydrous DMF (50 mL) in a 1000 mL screw-top glass pressure-vessel. This was sealed with the screw cap and allowed to stir for 45 min at room temperature. To this mixture was added a solution of 4-[(R)-1-(3,5-dichloro-4-fluoro-phenyl)-5-iodo-3-methyl-2-oxo-2,3-dihydro-1H-imidazo[1,2-a]imidazol-3-ylmethyl]-benzonitrile (40.0 g, 73.9 mmol) in anhydrous DMF (200 mL) followed by Pd(OAc)$_2$ (830 mg, 3.70 mmol) and anhydrous LiCl (9.40 g, 221 mmol). The vessel was capped tightly and allowed to stir at 80° C. for 20 h. In a well ventilated fume hood, the reaction was cooled to room temperature and the screw cap was slowly removed allowing for gas release. The reaction was transferred to a separatory funnel containing a solution of aqueous HCl (2N, 1 L) using EtOAc (1 L). The layers were separated and the organic phase was washed with aqueous 2N HCl (1 L). The combined aqueous phase was extracted with EtOAc (2×1 L). The combined organic phase was dried with MgSO$_4$ and concentrated in vacuo. Toluene was added to the dark colored residue causing precipitation of a solid. The solid was filtered and washed with 1:1 toluene:hexanes followed by hexanes. The filtrate was concentrated and re-processed in a similar manner to give additional solids. A total of 29.4 g of the title compound was obtained as an off-white solid, m/z. 459.4 [M+H]$^+$.

The following compounds were prepared using procedures similar to those described above:
(R)-5-(4-Cyano-benzyl)-7-(3,5-dichloro-phenyl)-5-methyl-6-oxo-6,7-dihydro-5H-imidazo[1,2-a]imidazole-3-carboxylic acid
(R)-7-(3,5-Dichloro-phenyl)-5-methyl-6-oxo-5-(4-trifluoromethoxy-benzyl)-6,7-dihydro-5H-imidazo[1,2-a]imidazole-3-carboxylic acid
(R)-7-(3,5-Dichloro-4-fluoro-phenyl)-5-methyl-6-oxo-5-(4-trifluoromethoxy-benzyl)-6,7-dihydro-5H-imidazo[1,2-a]imidazole-3-carboxylic acid
(R)-5-(4-Bromo-benzyl)-7-(3,5-dichloro-phenyl)-5-methyl-6-oxo-6,7-dihydro-5H-imidazo[1,2-a]imidazole-3-carboxylic acid
(R)-7-(3-Chloro-5-trifluoromethyl-phenyl)-5-(4-cyano-benzyl)-5-methyl-6-oxo-6,7-dihydro-5H-imidazo[1,2-a]imidazole-3-carboxylic acid (R)-5-(4-Cyano-benzyl)-7-(3,5-dichloro-4-fluoro-phenyl)-5-methyl-6-oxo-6,7-dihydro-5H-imidazo[1,2-a]imidazole-3-carbonyl chloride

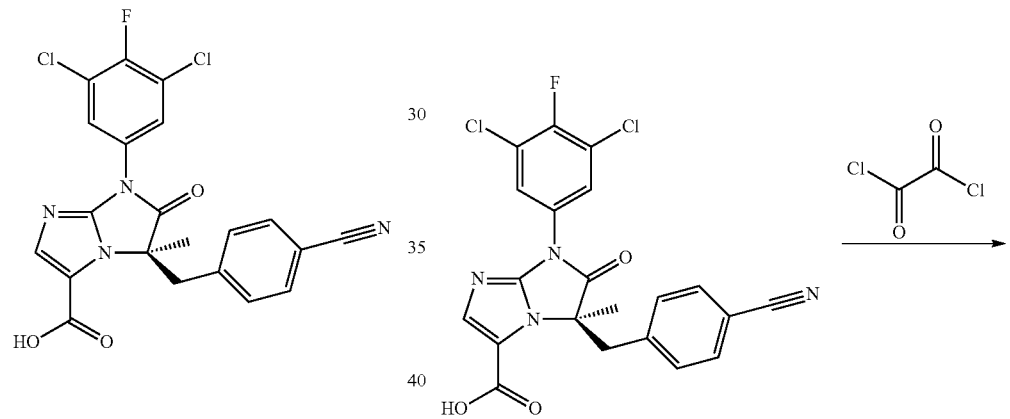

(R)-5-(4-Cyano-benzyl)-7-(3,5-dichloro-4-fluoro-phenyl)-5-methyl-6-oxo-6,7-dihydro-5H-imidazo[1,2-a]imidazole-3-carboxylic acid (44 g, 95.8 mmol) was dissolved in CH$_2$Cl$_2$ (600 mL). To this solution was added oxalyl chloride (16.7 g) followed by DMF (0.3 mL). After 2 h, the volatiles were removed and the resultant residue was placed under high vacuum for 18 h to yield the title compound. The title compound was used without purification.

1-{[(R)-5-(4-Bromo-benzyl)-7-(3,5-dichloro-phenyl)-5-methyl-6-oxo-6,7-dihydro-5H-imidazo[1,2-a]imidazole-3-carbonyl]-amino}-cyclopropanecarboxylic acid

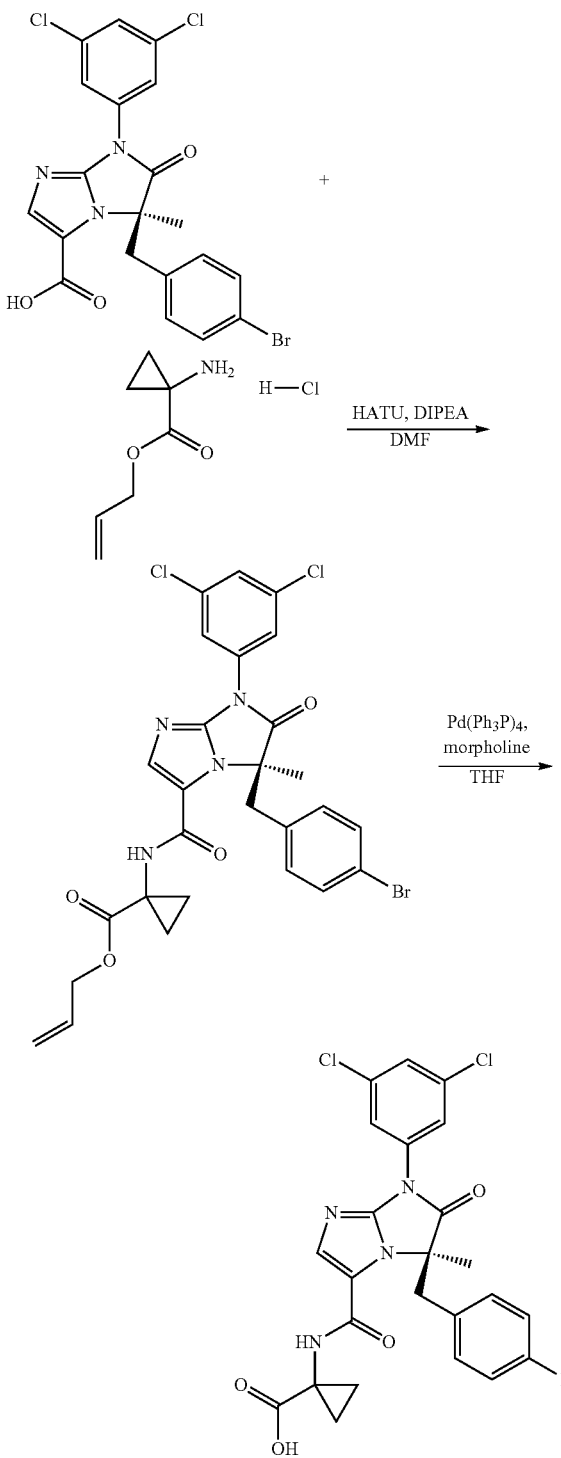

To a suspension of (R)-5-(4-bromo-benzyl)-7-(3,5-dichloro-phenyl)-5-methyl-6-oxo-6,7-dihydro-5H-imidazo[1,2-a]imidazole-3-carboxylic acid (1.00 g, 2.02 mmol) and 1-amino-cyclopropanecarboxylic acid allyl ester hydrochloride (430 mg, 2.42 mmol) in 6 mL of DMF at room temperature was added diisopropylethylamine (1.05 mL, 6.06 mmol), and the reaction mixture was stirred for 10 min. HATU (845 mg, 2.22 mmol) was then added, and the clear yellow reaction mixture was stirred at room temperature for 21 h. The reaction mixture was partitioned between 150 mL of ethyl acetate and 50 mL of 1M HCl. The organic phase was washed with satd. NaHCO₃ solution, water (2×), and brine, dried over Na₂SO₄, filtered, and concentrated. The residue was purified by flash chromatography on silica gel (10-30% EtOAc in hexanes), to furnish 1.16 g of 1-{[(R)-5-(4-bromo-benzyl)-7-(3,5-dichloro-phenyl)-5-methyl-6-oxo-6,7-dihydro-5H-imidazo[1,2-a]imidazole-3-carbonyl]-amino}-cyclopropanecarboxylic acid allyl ester (93%) as a colorless foam.

To a solution of 1-{[(R)-5-(4-bromo-benzyl)-7-(3,5-dichloro-phenyl)-5-methyl-6-oxo-6,7-dihydro-5H-imidazo[1,2-a]imidazole-3-carbonyl]-amino}-cyclopropanecarboxylic acid allyl ester (200 mg, 0.32 mmol) and morpholine (0.282 mL, 3.24 mmol) in 2 mL of THF was added Pd(Ph₃P)₄ (19 mg, 0.016 mmol). The reaction mixture was stirred at room temperature for 18 h. The reaction mixture was then diluted with 30 mL of EtOAc and washed with 10 mL each of 10% HCl solution, water, and brine, dried over Na₂SO₄, filtered, and concentrated. The residue was applied to a SiliaBond Carbonate preloaded cartridge (2 g, 0.7 mmol/g, Silicycle). The column was eluted with 30 mL of 10% MeOH in CH₂Cl₂ followed by 200 mL of 0.1:1:9 TFA/MeOH/CH₂Cl₂ to furnish 142 mg 76%) of the title compound as a colorless foam, m/z 579.4 [M+1]⁺.

The following compounds were prepared using procedures similar to those described above:

1-{[(R)-7-(3,5-Dichloro-phenyl)-5-methyl-6-oxo-5-(4-trifluoromethyl-benzyl)-6,7-dihydro-5H-imidazo[1,2-a]imidazole-3-carbonyl]-amino}-cyclopropanecarboxylic acid 1-{[(R)-7-(3,5-Dichloro-4-fluoro-phenyl)-5-methyl-6-oxo-5-(4-trifluoromethoxy-benzyl)-6,7-dihydro-5H-imidazo[1,2-a]imidazole-3-carbonyl]-amino}-cyclopropanecarboxylic acid 1-{[(R)-5-(4-Cyano-benzyl)-7-(3,5-dichloro-4-fluoro-phenyl)-5-methyl-6-oxo-6,7-dihydro-5H-imidazo[1,2-a]imidazole-3-carbonyl]-amino}-cyclopropanecarboxylic acid 1-{[(R)-5-(4-Cyano-benzyl)-7-(3,5-dichloro-phenyl)-5-methyl-6-oxo-6,7-dihydro-5H-imidazo[1,2-a]imidazole-3-carbonyl]-amino}-cyclopropanecarboxylic acid

1-{[(R)-5-(4-Chloro-benzyl)-7-(3,5-dichloro-phenyl)-5-methyl-6-oxo-6,7-dihydro-5H-imidazo[1,2-a]imidazole-3-carbonyl]-amino}-cyclopropanecarboxylic acid

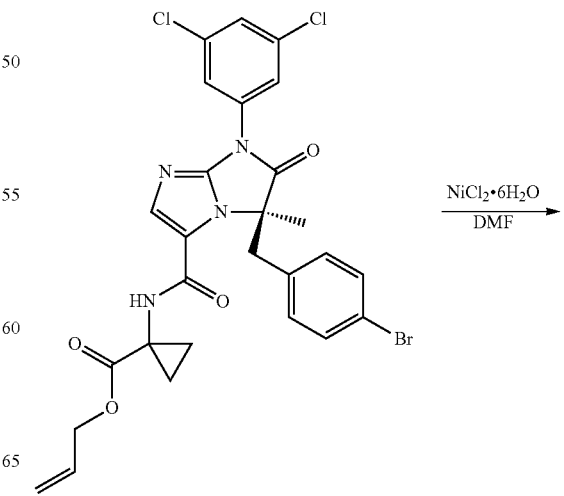

131

-continued

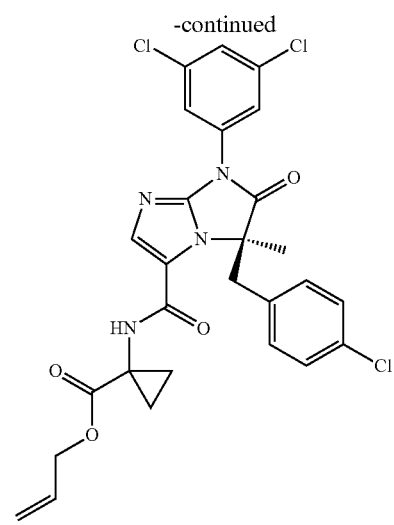

132

-continued

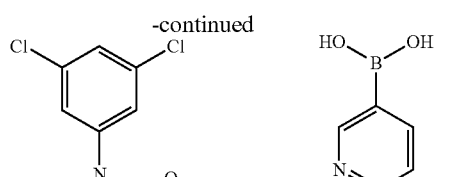

A microwave vial was charged with 1-{[(R)-5-(4-bromo-benzyl)-7-(3,5-dichloro-phenyl)-5-methyl-6-oxo-6,7-dihydro-5H-imidazo[1,2-a]imidazole-3-carbonyl]-amino}-cyclopropanecarboxylic acid allyl ester (400 mg, 0.647 mmol), NiCl$_2$·6H$_2$O (231 mg, 1.22 mmol), and 1.5 mL of DMF. The vial was sealed and heated in the microwave at 170° C. for 40 min, and then for 1 h. The crude reaction mixture was diluted with 30 mL of EtOAc and 15 mL of water (the solids were not soluble). The aqueous phase was extracted with 10 mL of EtOAc. The combined organics were washed with 5% NaCl solution (2×15 mL) and brine, dried over Na$_2$SO$_4$, filtered, and concentrated to afford 299 mg of a cloudy green oil, isolated as a ~1:1 mixture of the aryl bromide and the aryl chloride.

To a solution of the crude allyl esters (299 mg, ~0.25 mmol) and morpholine (0.436 mL, 5.0 mmol) in 3 mL of THF was added Pd(Ph$_3$P)$_4$ (29 mg, 0.0259 mmol). The reaction mixture was stirred at room temperature for 2 h. The reaction mixture was then diluted with 30 mL of EtOAc and washed with 10 mL each of 10% HCl solution, water, and brine, dried over Na$_2$SO$_4$, filtered, and concentrated. The crude product was isolated as a ~1:1 mixture of chloro to bromo acids and was carried to the next step without further purification.

The crude bromide/chloride acid mixture (~0.25 mmol) was concentrated in a microwave vial. To this mixture was added 3-pyridyl boronic acid (45 mg, 0.37 mmol), Pd(dppf)Cl$_2$.dichloromethane complex (20 mg, 0.024 mmol), 4 mL of DME/H$_2$O/EtOH (7/3/2), and aqueous K$_3$PO$_4$ solution (0.73 mL, 1M, 0.73 mmol). The vial was sealed and heated in the microwave at 100° C. for 15 min, followed by heating at 130° C. for an additional 30 min. The reaction mixture was then filtered through a plug of silica gel, washing with 10 mL of MeOH, and concentrated. The residue was diluted with 30 mL of EtOAc and washed with 10 mL each of 10% HCl solution, water, and brine, dried over Na$_2$SO$_4$, filtered, and concentrated. The crude oil was dissolved in DMSO/CH$_3$CN/H$_2$O (1:2:1, 1.2 mL) and purified by reverse-phase HPLC (40-95% CH$_3$CN/H$_2$O, 0.1% TFA). Concentration of the product fractions afforded 52 mg (~40%) of 1-{[(R)-5-(4-chloro-benzyl)-7-(3,5-dichloro-phenyl)-5-methyl-6-oxo-6,7-dihydro-5H-imidazo[1,2-a]imidazole-3-carbonyl]-amino}-cyclopropanecarboxylic acid.

Synthesis of Final Compounds

Example 1

(R)-5-(4-Cyano-benzyl)-7-(3,5-dichloro-phenyl)-5-methyl-6-oxo-6,7-dihydro-5H-imidazo[1,2-a]imidazole-3-carboxylic acid (1-{1-[4-(1H-pyrazol-4-yl)-pyridin-2-yl]-cyclopropylcarbamoyl}-cyclopropyl)-amide trifluoroacetic acid salt (Compound 124)

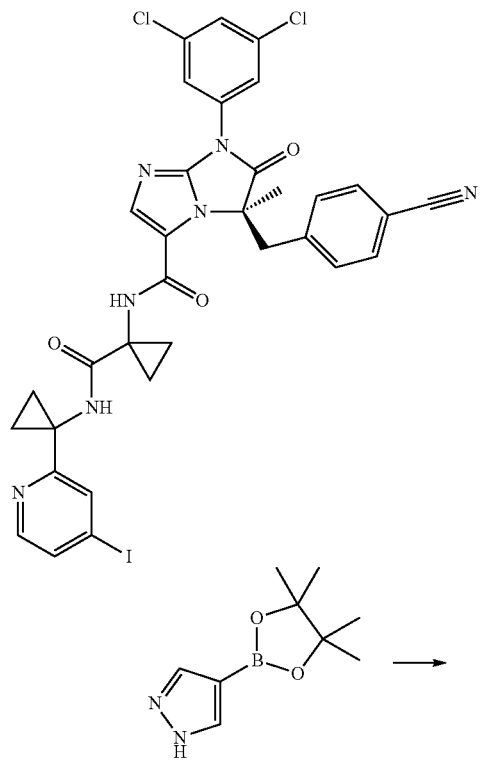

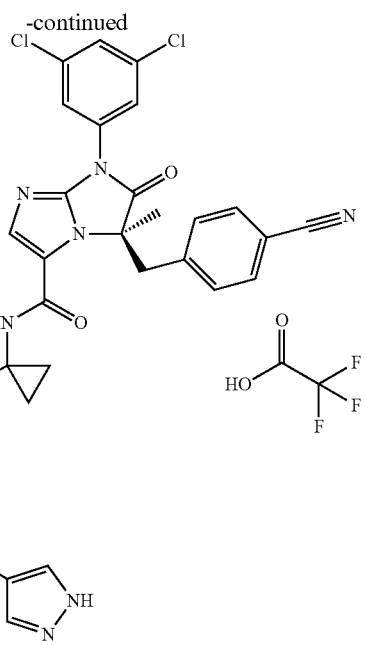

(R)-5-(4-Cyano-benzyl)-7-(3,5-dichloro-phenyl)-5-methyl-6-oxo-6,7-dihydro-5H-imidazo[1,2-a]imidazole-3-carboxylic acid{1-[1-(4-iodo-pyridin-2-yl)-cyclopropyl-carbamoyl]-cyclopropyl}-amide (40 mg, 0.052 mmol) was dissolved in DME (1.0 mL) and Pd(dppf)Cl$_2$.dichloromethane complex (4 mg, 0.005 mmol) was added. This solution was added to a microwave reaction tube containing 4-(4,4,5,5-tetramethyl-1,3,2-dioxaborolan-2-yl)-1H-pyrazole (15 mg, 0.08 mmol) and 1M K$_3$PO$_4$ solution (0.06 mL, 0.06 mmol), water (0.4 mL) and EtOH (0.3 mL). The reaction tube was sealed and heated in a microwave at 100° C. for 10 minutes. The reaction mixture was then filtered through a pad of silica gel washing with 10% methanol in CH$_2$Cl$_2$ (3×1 mL). The filtrate was concentrated and the resulting solid was purified via reverse phase HPLC to afford 23 mg of the title compound, m/z 706.3.

The following compounds were prepared using procedures similar to those described above using the appropriate intermediates:

| Compound | m/z |
|---|---|
| 1 | 738.9 |
| 2 | 750.6 |
| 3 | 785.7 |
| 8 | 797.8 |
| 9 | 706.3 |
| 11 | 724.6 |
| 12 | 783.8 |
| 13 | 778.7 |
| 14 | 778.8 |
| 16 | 774.4 |
| 18 | 749.7 |
| 20 | 809.6 |
| 21 | 740.8 |
| 23 | 813.8 |
| 25 | 803.9 |
| 27 | 750.8 |
| 31 | 739.6 |
| 32 | 765.7 |
| 33 | 725.7 |
| 34 | 751.4 |
| 38 | 764.8 |

-continued
| Compound | m/z |
|---|---|
| 39 | 824.8 |
| 41 | 824.8 |
| 43 | 765.8 |
| 52 | 760.3 |
| 53 | 758.3 |
| 54 | 731.3 |
| 55 | 735.3 |
| 56 | 787.3 |
| 57 | 731.3 |
| 58 | 735.3 |
| 59 | 773.3 |
| 60 | 734.3 |
| 61 | 753.2 |
| 62 | 731.3 |
| 63 | 735.3 |
| 64 | 712.8 |
| 65 | 753.4 |
| 66 | 759.7 |
| 67 | 706.7 |
| 68 | 735.7 |
| 69 | 735.7 |
| 70 | 777.7 |
| 71 | 742.7 |
| 72 | 777.9 |
| 73 | 775.9 |
| 74 | 760.9 |
| 95 | 769.8 |
| 96 | 765.6 |
| 99 | 783.7 |
| 100 | 764.7 |
| 101 | 766.7 |
| 109 | 766.8 |
| 110 | 825.6 |
| 111 | 753.7 |
| 112 | 750.7 |
| 114 | 779.7 |
| 115 | 813.6 |
| 123 | 752.8 |
| 126 | 773.4 |
| 127 | 707.2 |
| 128 | 719.3 |
| 129 | 706.3 |
| 130 | 750.3 |
| 131 | 759.3 |
| 132 | 795.3 |
| 133 | 809.3 |
| 134 | 794.3 |
| 135 | 732.3 |
| 136 | 746.3 |
| 137 | 741.3 |
| 138 | 795.3 |
| 139 | 773.3 |
| 140 | 809.3 |
| 141 | 794.3 |
| 142 | 732.3 |
| 143 | 746.3 |
| 144 | 823.3 |
| 146 | 756.3 |
| 147 | 755.3 |
| 148 | 730.3 |
| 149 | 720.3 |
| 156 | 752.8 |
| 157 | 752.6 |
| 158 | 812.7 |
| 160 | 753.4 |
Example 2
(R)-7-(3,5-Dichloro-4-fluoro-phenyl)-5-methyl-6-oxo-5-(4-trifluoromethoxy-benzyl)-6,7-dihydro-5H-imidazo[1,2-a]imidazole-3-carboxylic acid(1-{1-[5-(1-methyl-1H-pyrazol-4-yl)-pyrimidin-2-yl]-cyclopropylcarbamoyl}-cyclopropyl)-amide
(Compound 40)
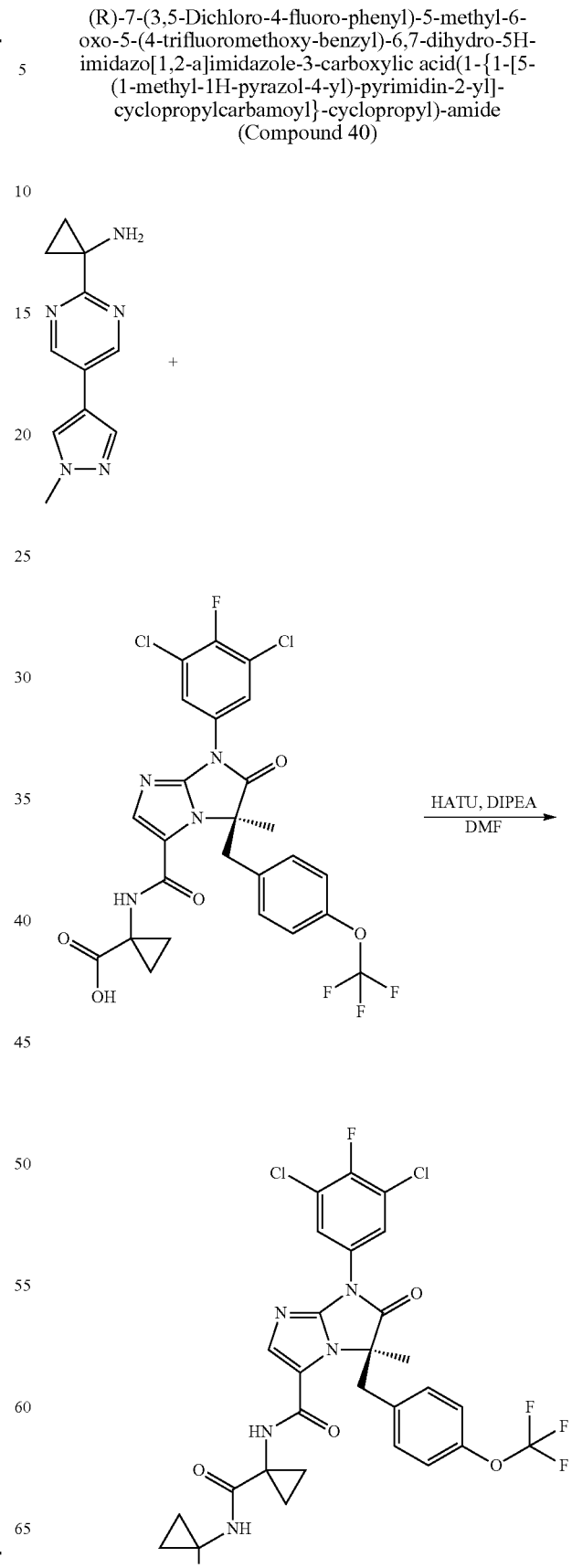

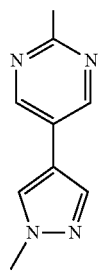

To a solution of 1-{[(R)-7-(3,5-dichloro-4-fluoro-phenyl)-5-methyl-6-oxo-5-(4-trifluoromethoxy-benzyl)-6,7-dihydro-5H-imidazo[1,2-a]imidazole-3-carbonyl]-amino}-cyclopropanecarboxylic acid (130 mg, 0.22 mmol) and 1-[5-(1-methyl-1H-pyrazol-4-yl)-pyrimidin-2-yl]-cyclopropylamine hydrochloride (75 mg, 0.26 mmol) in DMF (1 mL) was added diisopropylethylamine (0.15 mL, 0.87 mmol) and HATU (990 mg, 0.24). After 1 h, the reaction mixture was purified by reversed phase MPLC (C18, 30 g, Mobile phase: CH₃CN (0.1% TFA), water (0.1% TFA), Gradient: 70% water to 10% water). The pure fractions were combined and concentrated in-vacuo to remove most of the CH₃CN and then partitioned between 50 mL of CH₂Cl₂, 20 mL of water, and 10 mL of saturated aqueous NaHCO₃ solution. The organic phase was washed with brine, dried over Na₂SO₄, filtered, and concentrated to afford 146 mg of the title compound as a white foam, m/z=798.8.

The following compounds were prepared using procedures similar to those described above using the appropriate intermediates:

| Compound | m/z |
| --- | --- |
| 4 | 798.8 |
| 10 | 789.7 |
| 15 | 779.7 |
| 19 | 788.6 |
| 24 | 807.8 |
| 26 | 763.9 |
| 29 | 768.7 |
| 35 | 739.6 |
| 36 | 753.7 |
| 37 | 765.6 |
| 42 | 784.7 |
| 51 | 754.8 |
| 75 | 775.5 |
| 76 | 729.7 |
| 77 | 729.7 |
| 81 | 707.7 |
| 82 | 706.6 |
| 83 | 706.6 |
| 86 | 810.8 |
| 89 | 824.8 |
| 97 | 807.6 |
| 98 | 748.6 |
| 102 | 790.8 |
| 103 | 792.8 |
| 105 | 751.8 |
| 108 | 810.6 |
| 113 | 738.8 |
| 116 | 812.7 |
| 122 | 726 |
| 150 | 811.7 |

Example 3

(R)-5-(4-Cyano-benzyl)-7-(3,5-dichloro-phenyl)-5-methyl-6-oxo-6,7-dihydro-5H-imidazo[1,2-a]imidazole-3-carboxylic acid(1-{1-[5-(1-methyl-1H-imidazol-2-yl)-pyridin-2-yl]-cyclopropylcarbamoyl}-cyclopropyl)-amide bistrifluoroacetic acid salt (Compound 80)

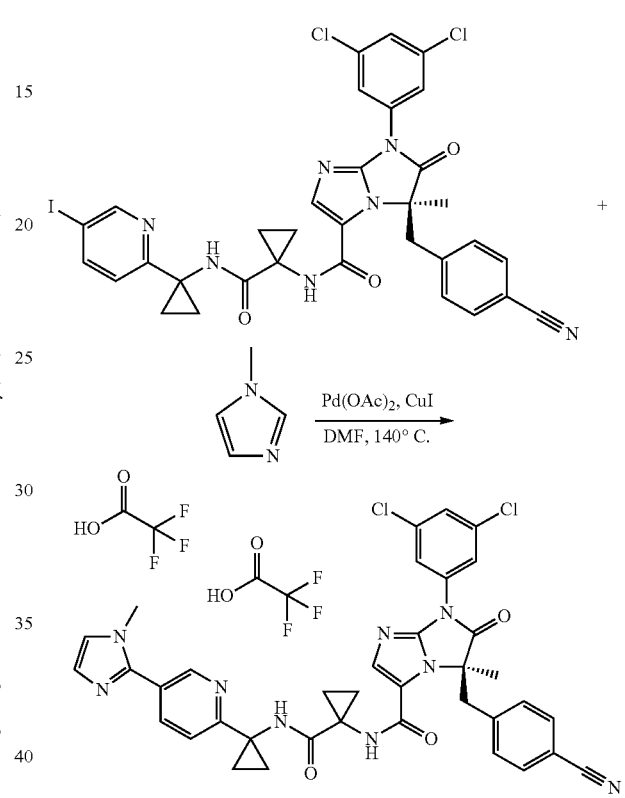

(R)-5-(4-Cyano-benzyl)-7-(3,5-dichloro-phenyl)-5-methyl-6-oxo-6,7-dihydro-5H-imidazo[1,2-a]imidazole-3-carboxylic acid{1-[1-(5-iodo-pyridin-2-yl)-cyclopropyl-carbamoyl]-cyclopropyl}-amide (50 mg, 0.07 mmol), 1-methyl-1H-imidazole (10.3 μL, 0.13 mmol), Pd(OAc)₂ (2.9 mg, 0.013 mmol) and CuI (24.8 mg, 0.13 mmol) were mixed together in a microwave tube and then DMF (0.5 mL) was added. Argon was bubbled through the mixture for 15 min and then the reaction was heated at 140° C. for 24 h. The reaction was diluted with 10 mL of MeOH and filtered through a pad of silica. The residue was purified by reverse phase HPLC to give the title compound (18 mg, 0.025 mmol, 38%) as a semi-solid, m/z=720.7 [M+H]⁺.

The following compounds were prepared using procedures similar to those described above using the appropriate intermediates:

| Compound | m/z |
| --- | --- |
| 79 | 706.6 |
| 94 | 735.8 |

Example 4

(R)-5-(4-Cyano-benzyl)-7-(3,5-dichloro-phenyl)-5-methyl-6-oxo-6,7-dihydro-5H-imidazo[1,2-a]imidazole-3-carboxylic acid(1-{1-[5-(3-methyl-3H-imidazol-4-yl)-pyridin-2-yl]-cyclopropylcarbamoyl}-cyclopropyl)-amide bistrifluoroacetic acid salt
(Compound 84)

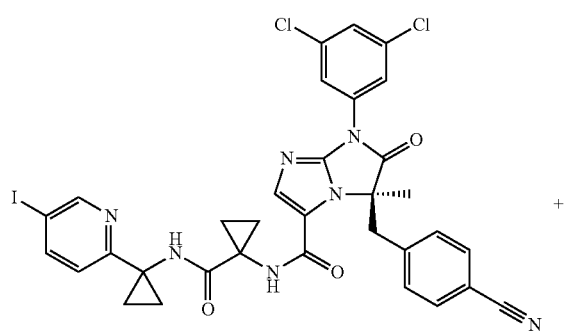

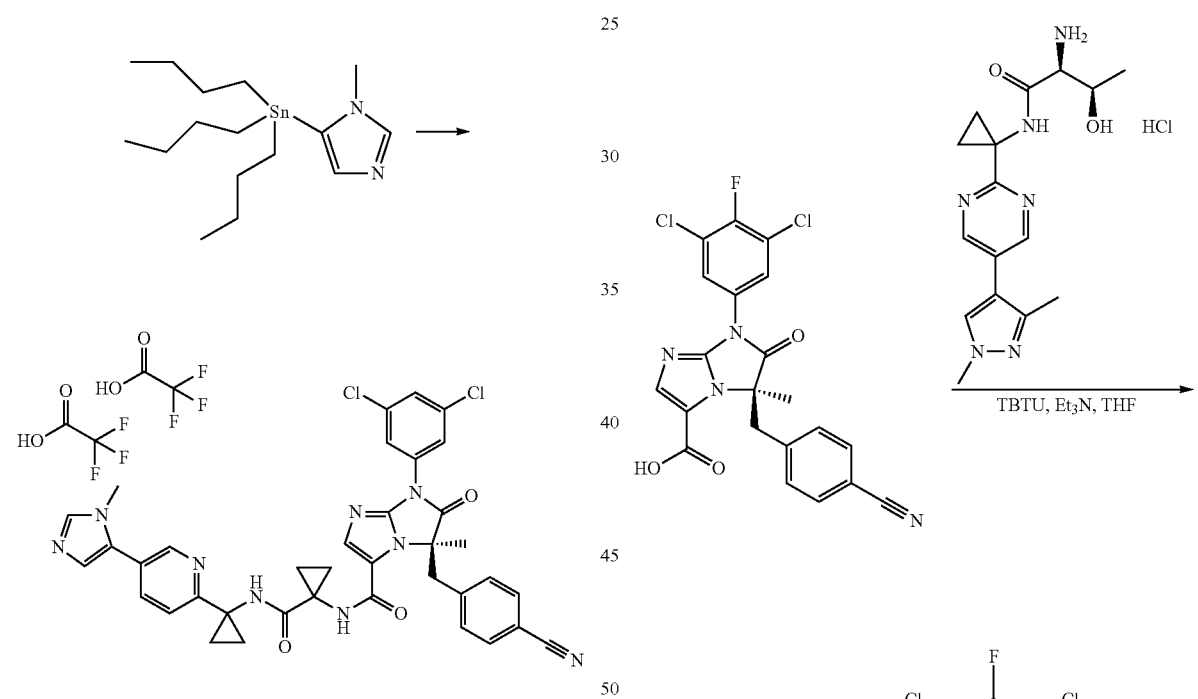

(R)-5-(4-Cyano-benzyl)-7-(3,5-dichloro-4-fluoro-phenyl)-5-methyl-6-oxo-6,7-dihydro-5H-imidazo[1,2-a]imidazole-3-carboxylic acid{1-[1-(5-iodo-pyridin-2-yl)-cyclopropylcarbamoyl]-cyclopropyl}-amide (50 mg, 0.07 mmol), 1-methyl-5-tributylstannanyl-1H-imidazole (48 mg, 0.13 mmol) and THF (2 mL) were combined and argon was bubbled through the reaction mixture for 15 minutes. Pd(dppf)Cl$_2$.dichloromethane complex (11 mg, 0.013 mmol) was then added to the solution and degassing was continued for 10 minutes. The reaction was then heated at 80° C. After 18 h, the solvent was evaporated. The solid residue was dissolved in DMSO (1 mL) and purified by reverse phase HPLC yielding 36 mg of the title compound as a white solid, m/z=720.7 [M+H]$^+$.

The following compounds were prepared using procedures similar to those described above using the appropriate intermediates:

| Compound | m/z |
|---|---|
| 22 | 735.8 |
| 85 | 777.7 |
| 91 | 723.6 |
| 92 | 723.7 |

Example 5

(R)-5-(4-Cyano-benzyl)-7-(3,5-dichloro-4-fluoro-phenyl)-5-methyl-6-oxo-6,7-dihydro-5H-imidazo[1,2-a]imidazole-3-carboxylic acid((1S,2R)-1-{1-[5-(1,3-dimethyl-1H-pyrazol-4-yl)-pyrimidin-2-yl]-cyclopropylcarbamoyl}-2-hydroxy-propyl)-amide
(Compound 145)

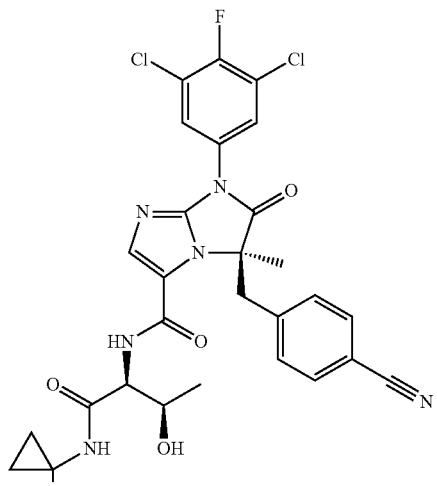

-continued

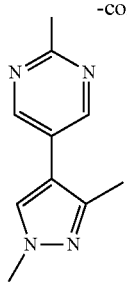

To a flask was added (R)-5-(4-cyano-benzyl)-7-(3,5-dichloro-4-fluoro-phenyl)-5-methyl-6-oxo-6,7-dihydro-5H-imidazo[1,2-a]imidazole-3-carboxylic acid (0.80 g, 2.18 mmol), TBTU (0.73 g, 2.28 mmol) and Et$_3$N (0.91 mL, 6.54 mmol) and THF (10 mL). The mixture was allowed to stir at RT for 30 min. The mixture was transferred to a separate flask containing (2S,3R)-2-amino-N-{1-[5-(1,3-dimethyl-1H-pyrazol-4-yl)-pyrimidin-2-yl]-cyclopropyl}-3-hydroxy-butyramide hydrochloride (1.0 g, 2.18 mmol) in THF (30 mL). The mixture was stirred at RT for 24 h. The mixture was concentrated and purified by silica gel chromatography to provide 1.45 g of the title compound as a white solid following removal of the solvent, m/z=771.8 [M+H]$^+$.

The following compounds were prepared using procedures similar to those described above using the appropriate intermediates:

| Compound | m/z |
|---|---|
| 5 | 727.8 |
| 6 | 757.9 |
| 7 | 816.8 |
| 17 | 865.6 |
| 28 | 785.9 |
| 30 | 755.7 |
| 44 | 713.8 |
| 45 | 743.8 |
| 46 | 772.8 |
| 47 | 802.8 |
| 48 | 852.8 |
| 49 | 812.8 |
| 50 | 753.8 |
| 78 | 754.6 |
| 87 | 752.8 |
| 88 | 726.7 |
| 90 | 753.7 |
| 93 | 712.7 |
| 104 | 815.8 |
| 106 | 753.8 |
| 107 | 726.8 |
| 117 | 741.8 |
| 118 | 800.8 |
| 119 | 771.8 |
| 120 | 830.8 |
| 121 | 758.7 |
| 125 | 843.7 |
| 151 | 770.7 |
| 152 | 756.7 |
| 153 | 801.9 |
| 154 | 756.7 |
| 155 | 770.8 |
| 159 | 760.7 |

Description of Biological Properties

The biological properties of representative compounds of the formula I were investigated by way of the experimental protocol described below.

Assay to Determine Inhibition of LFA-1 Binding to ICAM-1

Purpose of Assay:

This assay protocol is designed to study the direct antagonism, by a test compound, of the interaction of ICAM-1 with the Leukointegrin CD18/CD11a (LFA-1).

Description of Assay Protocol:

The LFA-1/Biotin-sICAM-1 molecular assay measures the ability of test compounds to inhibit binding of LFA-1 to Biotinylated-sICAM using AlphaScreen technology (Ref: Wilson, J, Rossi, C P, Carboni, S, Fremaux, C, Perrin, D, Soto, C, Kosco-Vilbois, M, and Scheer, A: A Homogeneous 384-Well High-Throughput Binding Assay for a TNF Receptor Using Alphascreen Technology. J Biomol Screen 2003; 8:522-532) that uses TS2/4(anti-LFA-1)-custom conjugated AlphaLisa acceptor beads and streptavidin-coated donor beads from PerkinElmer. The assay was performed in white OptiPlates-384 in a volume of 60 µL using assay buffer (Dulbecco's PBS containing calcium and magnesium, 2 mM MgCl2, 0.1 mM PMSF, 0.1% BSA, pH 7.1). To each well, Biotin-sICAM was added followed by purified LFA-1 (in buffer of 50 mM triethylamine, 150 mM NaCl, 1% beta octylglucoside, 2 mM MgCl$_2$ neutralized to pH with 1M Tris-HCl, pH 7.5). For compound testing, compound was added in 5 uL to the above in 25 uL. LFA-1 and Biotin-sICAM-1 were used at concentrations that would yield a signal to background ratio of 8-10. The highest concentration of compound was 1 µM in 1% DMSO. Positive controls were wells without compound containing LFA-1, while blanks were wells without both compound and LFA-1. Plates were mixed and incubated at 37° C. for 90 minutes. This was followed by addition of 15 µL/well TS2/4-conjugated acceptor beads diluted in PBS containing 0.1% BSA for a final concentration of 10 µg/mL. The plates were mixed and incubated in the dark for 30 minutes at room temperature followed by addition of 15 µL/well streptavidin-coated donor beads diluted in PBS containing 0.1% BSA at a final concentration of 15 µg/mL. The plates were mixed and incubated in the dark for 60 minutes at room temperature and then read on an EnVision Multilabel Reader using AlphaScreen 384-well OptiPlate protocol.

Compounds made in the above examples were tested in this assay and each was found to have an IC$_{50}$<1 µM. Data from this assay is provided in the table below:

| Compound # | Alphascreen IC$_{50}$ (nM) |
|---|---|
| 1 | 0.88 |
| 2 | 1.1 |
| 4 | 1.5 |
| 5 | 1.2 |
| 6 | 0.44 |
| 7 | 1.4 |
| 8 | 1.3 |
| 10 | 1 |
| 11 | 1.2 |
| 12 | 1.1 |
| 13 | 1.8 |
| 14 | 1.1 |
| 15 | 1.6 |
| 16 | 1 |
| 18 | 1.4 |
| 20 | 1.5 |
| 21 | 0.51 |
| 23 | 0.8 |
| 27 | 1.5 |
| 28 | 2.9 |
| 30 | 0.61 |
| 31 | 0.51 |
| 32 | 1.4 |

| Compound # | Alphascreen IC$_{50}$ (nM) |
|---|---|
| 33 | 0.57 |
| 34 | 1 |
| 35 | 0.48 |
| 37 | 0.89 |
| 38 | 1.7 |
| 39 | 1.8 |
| 40 | 1.7 |
| 41 | 1.2 |
| 42 | 1.3 |
| 43 | 0.62 |
| 44 | 0.53 |
| 45 | 0.38 |
| 46 | 0.77 |
| 47 | 1.2 |
| 49 | 1.3 |
| 50 | 1.3 |
| 51 | 1.2 |
| 52 | 0.72 |
| 54 | 0.53 |
| 56 | 0.67 |
| 58 | 0.71 |
| 60 | 0.96 |
| 61 | 1 |
| 62 | 1.1 |
| 64 | 0.61 |
| 65 | 0.53 |
| 66 | 1.3 |
| 68 | 0.6 |
| 69 | 0.99 |
| 70 | 0.8 |
| 72 | 0.83 |
| 75 | 1.2 |
| 78 | 1.2 |
| 87 | 1.9 |
| 88 | 0.89 |
| 89 | 0.58 |
| 90 | 0.28 |
| 93 | 0.7 |
| 96 | 0.97 |
| 100 | 1.3 |
| 101 | 1.1 |
| 103 | 1.3 |
| 104 | 1.2 |
| 105 | 0.68 |
| 106 | 1.1 |
| 108 | 1.1 |
| 109 | 1.4 |
| 110 | 0.65 |
| 111 | 1.6 |
| 112 | 0.54 |
| 115 | 1.8 |
| 116 | 1.3 |
| 117 | 0.58 |
| 118 | 0.86 |
| 119 | 0.85 |
| 120 | 0 |
| 121 | 1.1 |
| 123 | 1.4 |
| 125 | 0 |
| 127 | 0.34 |
| 129 | 0.22 |
| 131 | 0.99 |
| 132 | 0.72 |
| 133 | 1.5 |
| 134 | 0.64 |
| 135 | 0.64 |
| 136 | 0.56 |
| 138 | 0.64 |
| 141 | 0.53 |
| 142 | 1.7 |
| 143 | 1.9 |
| 145 | 0 |
| 146 | 1.6 |
| 149 | 0.33 |
| 150 | 0.68 |
| 151 | 1.2 |
| 152 | 1.1 |
| 153 | 0.93 |
| 154 | 0.76 |
| 155 | 0.56 |
| 156 | 0.77 |
| 157 | 0.91 |
| 158 | 1.3 |
| 159 | 0.44 |
| 160 | 0.59 |

Assay to Determine Inhibition IL-2 Production in Whole Blood

Purpose of Assay:

This assay protocol is designed to study the functional antagonism, by a test compound, of the interaction of ICAM-1 with the Leukointegrin CD18/CD11a (LFA-1).

Description of Assay Protocol:

Compounds were evaluated for their ability to inhibit the production of IL-2 by cells present in freshly drawn heparinized human whole blood after stimulation ex vivo by staphylococcal enterotoxin B (SEB). Compounds were diluted in human AB serum to 11× their final assay concentration. Following further dilution for concentration response curves in human AB serum containing 1.12% DMSO, human whole blood was added to the compounds. Following a 30 minute incubation of blood and compound, SEB was then added to yield a final concentration of 600 ng/mL SEB and a final DMSO concentration of 0.1%. After overnight incubation (37° C. humidified $CO_2$ incubator), plasma samples were collected and analyzed for the presence of IL-2 using an electrochemiluminescence protocol. For this assay a biotinylated anti-human IL-2 antibody (R&D Systems BAF202), an MSD Sulfo-TAG (MSD R91AN-2) labeled anti-human IL-2 monoclonal antibody (R&D Systems MAB602), and MSD Standard Avidin plates were employed to measure IL-2 in plasma samples.

Representative compounds made in the above examples were tested in this assay and most were found to have an IC$_{50}$<10 µM.

Assay to Determine Metabolic Stability by Human Liver Microsomes

Purpose of Assay:

This assay protocol is designed to study the stability of a test compound toward metabolic oxidation by human liver microsomes.

Description of Assay Protocol:

Compounds were incubated in human liver microsomes to estimate the disappearance $t_{1/2}$ of the parent compound. Assay was performed in 50 mM potassium phosphate buffer, pH 7.4 and 2.5 mM NADPH. Compounds were tested at a final assay concentration of 1 µM. The protein concentration was 1 mg/mL. The reaction was pre-incubated at 37° C. for 5 min, and the metabolic reactions were initiated by the addition of NADPH. Aliquots were removed at 0, 5, and 30 minutes and were precipitated with acetonitrile containing internal standard. The samples were filtered through 0.25 mm glass fiber filter plates and the supernatant was analyzed by LC/MS/MS. Percent loss of parent compound was calculated from the peak area ratio (compound/internal standard) at each time point in comparison to the peak area ratio of the zero minute sample to determine the $t_{1/2}$ in minutes. The half life in minutes using 1 mg of microsomal protein was converted into intrinsic clearance (CLint) by scaling up the data for mg of microsomal protein/g liver and for g liver/kg body weight using the following:

$$CLint(\text{in mL/min/kg}) = 0.693/T_{1/2} * \text{mL}/1 \text{ mg} * 45 \text{ mg}$$
$$LM/\text{g liver} * 25.7 \text{ g liver/kg b.w.}$$

Clint was then scaled up to estimate a whole body clearance using the well-stirred model using the following:

$$CL_H(\text{in mL/min/kg}) = Q_H * CLint/(Q_H + CLint)$$

where $Q_H$ is hepatic blood flow, 20.7 mL/min/kg in a human. $CL_H$ can then be expressed as a percent of $Q_H$ (% $Q_H$).

Representative compounds made in the above examples were tested in this assay and most compounds were found to be metabolized at a low to moderate rate of <75% $Q_H$.

Description of Therapeutic Use

The novel small molecules of formula I provided by the invention inhibit the ICAM-1/LFA-1 dependent homotypic aggregation of human lymphocytes and human lymphocyte adherence to ICAM-1. These compounds have therapeutic utility in the modulation of immune cell activation/proliferation, e.g., as competitive inhibitors of intercellular ligand/receptor binding reactions involving CAMs and Leukointegrins. To be more specific, the compounds of the invention may be used to treat certain inflammatory conditions, including conditions resulting from a response of the specific immune system in a mammal (e.g., asthma, psoriasis, organ/tissue transplant rejection, graft vs. host reactions and autoimmune diseases including Raynaud's syndrome, autoimmune thyroiditis, dermatitis, multiple sclerosis, rheumatoid arthritis, insulin-dependent diabetes mellitus, uveitis, inflammatory bowel disease including Crohn's disease and ulcerative colitis, and systemic lupus erythematosus) and conditions resulting from a response of the non-specific immune system in a mammal (e.g., adult respiratory distress syndrome, shock, oxygen toxicity, multiple organ injury syndrome secondary to septicemia, multiple organ injury syndrome secondary to trauma, reperfusion injury of tissue due to cardiopulmonary bypass, myocardial infarction, acute glomerulonephritis, vasculitis, reactive arthritis, dermatosis with acute inflammatory components, stroke, thermal injury, hemodialysis, leukapheresis, necrotizing enterocolitis and granulocyte transfusion associated syndrome). Preferably, the compounds of the invention can be used to treat psoriasis and multiple sclerosis.

Thus, another aspect of the invention is directed to a compound of formula I for use as a medicament and, in a particular aspect, for use as a medicament for the treatment of inflammation or an inflammatory condition. In another particular aspect, the invention is directed to a compound of formula I for use as a medicament for the treatment of any of the diseases or conditions listed in the previous paragraph. In another aspect, the invention is directed to the use of a compound of formula I for the manufacture of a medicament for the treatment of any of the diseases or conditions listed in the previous paragraph.

Thus, another aspect of the invention is the provision of a method for the treatment or prophylaxis of the above-described conditions through the administration of therapeutic or prophylactic amounts of one or more compounds of the formula I.

In accordance with the method provided by the invention, the novel compounds of formula I may be administered for either a prophylactic or therapeutic purpose either alone or with other immunosuppressive or antiinflammatory agents. When provided prophylactically, the immunosuppressive compound(s) are provided in advance of any inflammatory response or symptom (for example, prior to, at, or shortly after the time of a relapse in multiple sclerosis). The prophylactic administration of a compound of the formula I serves to prevent or attenuate any subsequent inflammatory response (such as, for example, a relapse in multiple sclerosis). The therapeutic administration of a compound of the formula I serves to attenuate any actual inflammation (such as, for example, a relapse in multiple sclerosis). Thus, in accordance with the invention, a compound of the formula I can be administered either prior to the onset of inflammation (so as to suppress an anticipated inflammation) or after the initiation of inflammation.

The novel compounds of the formula I may, in accordance with the invention, be administered in single or divided doses by the oral, parenteral or topical routes. A suitable oral dosage for a compound of formula I would be in the range of about 0.1 mg to 10 g per day, preferably in the range of 1 mg to 100 mg per day. In parenteral formulations, a suitable dosage unit may contain from 0.1 to 250 mg of said compounds, whereas for topical administration, formulations containing 0.01 to 1% active ingredient are preferred. It should be understood, however, that the dosage administration from patient to patient will vary and the dosage for any particular patient will depend upon the clinician's judgement, who will use as criteria for fixing a proper dosage the size and condition of the patient as well as the patient's response to the drug.

When the compounds of the present invention are to be administered by the oral route, they may be administered as medicaments in the form of pharmaceutical preparations which contain them in association with a compatible pharmaceutical carrier material. Such carrier material can be an inert organic or inorganic carrier material suitable for oral administration. Examples of such carrier materials are water, gelatin, talc, starch, magnesium stearate, gum arabic, vegetable oils, polyalkylene-glycols, petroleum jelly and the like.

The pharmaceutical preparations can be prepared in a conventional manner and finished dosage forms can be solid dosage forms, for example, tablets, dragees, capsules, and the like, or liquid dosage forms, for example solutions, suspensions, emulsions and the like. The pharmaceutical preparations may be subjected to conventional pharmaceutical operations such as sterilization. Further, the pharmaceutical preparations may contain conventional adjuvants such as preservatives, stabilizers, emulsifiers, flavor-improvers, wetting agents, buffers, salts for varying the osmotic pressure and the like. Solid carrier material which can be used include, for example, starch, lactose, mannitol, methyl cellulose, microcrystalline cellulose, talc, silica, dibasic calcium phosphate, and high molecular weight polymers (such as polyethylene glycol).

For parenteral use, a compound of formula I can be administered in an aqueous or non-aqueous solution, suspension or emulsion in a pharmaceutically acceptable oil or a mixture of liquids, which may contain bacteriostatic agents, antioxidants, preservatives, buffers or other solutes to render the solution isotonic with the blood, thickening agents, suspending agents or other pharmaceutically acceptable additives. Additives of this type include, for example, tartrate, citrate and acetate buffers, ethanol, propylene glycol, polyethylene glycol, complex formers (such as EDTA), antioxidants (such as sodium bisulfite, sodium metabisulfite, and ascorbic acid), high molecular weight polymers (such as liquid polyethylene oxides) for viscosity regulation and polyethylene derivatives of sorbitol anhydrides. Preservatives may also be added if necessary, such as benzoic acid, methyl or propyl paraben, benzalkonium chloride and other quaternary ammonium compounds.

The compounds of this invention may also be administered as solutions for nasal application and may contain in addition to the compounds of this invention suitable buffers, tonicity adjusters, microbial preservatives, antioxidants and viscosity-increasing agents in an aqueous vehicle. Examples of agents used to increase viscosity are polyvinyl alcohol, cellulose derivatives, polyvinylpyrrolidone, polysorbates or glycerin. Microbial preservatives added may include benzalkonium chloride, thimerosal, chloro-butanol or phenylethyl alcohol.

Additionally, the compounds provided by the invention can be administered topically or by suppository.

We claim:

1. A compound of formula I:

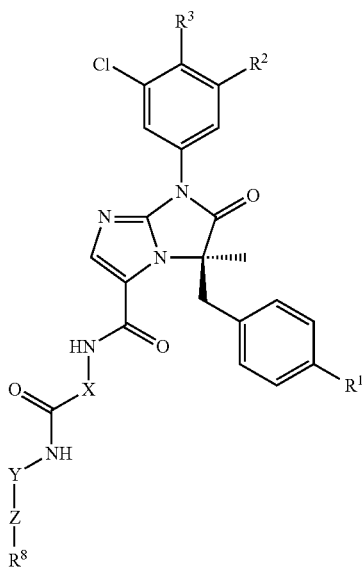

wherein:
$R^1$ is selected from —CN, —OCF$_3$, —CF$_3$, halogen, heteroaryl optionally substituted with halogen or $C_{1-3}$ alkyl and phenyl optionally substituted with halogen;
$R^2$ is —Cl or —CF$_3$;
$R^3$ is H or halogen;
X is a group

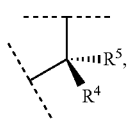

wherein
$R^4$ is selected from:
(A) -H;
(B) $C_{1-3}$ alkyl optionally substituted with one or two groups selected from:
a) $C_{3-6}$cycloalkyl;
b) —OR$^9$;
c) —NR$^9$R$^{10}$;
d) —SOR$^9$;
e) —SO$_2$R$^9$;
f) —C(O)NR$^9$R$^{10}$;
g) —C(O)OR$^9$;
h) heteroaryl, optionally substituted with $C_{1-3}$ alkyl;
i) heterocycyl, optionally substituted with $C_{1-3}$ alkyl; and
j) phenyl optionally substituted with $C_{1-3}$ alkyl;
(C) $C_{3-6}$cycloalkyl;
(D) heteroaryl; and
(E) phenyl, optionally substituted with halogen, —OR$^9$, —CN or —CF$_3$;
$R^5$ is H or $C_{1-3}$alkyl; or
$R^4$ and $R^5$, together with the carbon they are bonded to, form a saturated hydrocarbon ring with 3-7 carbon atoms and wherein one carbon atom in said hydrocarbon ring may be optionally replaced by —O—, —S—, —S(O)—, —SO$_2$—, —NH—, —NCH$_3$—, or —NC(O)CH$_3$—;
Y is a group

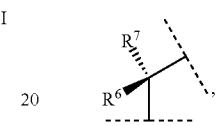

wherein
$R^6$ is H or $C_{1-3}$alkyl;
$R^7$ is H or $C_{1-3}$alkyl; or
$R^6$ and $R^7$, together with the carbon they are bonded to, form a saturated hydrocarbon ring with 3-7 carbon atoms wherein one carbon atom in said hydrocarbon ring may be optionally replaced by —O—, —S—, —S(O) —, —SO$_2$—, —NH—, —NCH$_3$—, or —NC(O)CH$_3$—;
Z is aryl or heteroaryl;
$R^8$ is selected from:
(A) aryl optionally substituted with one or two groups selected from:
(a) $C_{1-3}$alkyl optionally substituted with —OR$^9$, —NR$^9$R$^{10}$ or —NR$^9$SO$_2$R$^{10}$;
(b) $C_{3-7}$cycloalkyl optionally substituted with —OR$^9$ or —NR$^9$R$^{10}$;
(a) —OR$^9$;
(c) halogen;
(d) —C(O)NR$^9$R$^{10}$;
(e) —SO$_2$NR$^9$R$^{10}$;
(f) —NR$^9$(CO)R$^{10}$;
(g) —SO$_2$R$^9$;
(h) —NR$^9$R$^{10}$;
(i) —CN;
(j) —C(O)OR$^9$;
(k) —NR$^9$SO$_2$R$^{10}$; and
(l) —C(O)R$^9$; and
(B) heteroaryl optionally substituted with one to two groups selected from:
(a) $C_{1-3}$alkyl optionally substituted with —OR$^9$, NR$^9$R$^{10}$ or halogen;
(b) $C_{3-7}$cycloalkyl optionally substituted with —OR$^9$, NR$^9$R$^{10}$;
(a) —OR$^9$;
(c) halogen;
(d) —C(O)NR$^9$R$^{10}$;
(e) —SO$_2$NR$^9$R$^{10}$;
(f) —NR$^9$(CO)R$^{10}$;
(g) —SO$_2$R$^9$;
(h) —NR$^9$R$^{10}$; and
(i) —CN;
$R^9$ is selected from H, $C_{1-5}$alkyl or $C_{3-7}$cycloalkyl;
$R^{10}$ is selected from H, $C_{1-5}$alkyl or $C_{3-7}$cycloalkyl;
or a pharmaceutically acceptable salt thereof.

2. A compound of formula I according to claim 1 wherein:
$R^1$ is selected from —CN, —OCF$_3$, —Br, —Cl or —CF$_3$;
$R^2$ is —Cl or —CF$_3$;
$R^3$ is —F or H;
X is a group

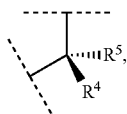

wherein
$R^4$ is selected from:
(A) C$_{1-2}$alkyl optionally substituted with —OH;
(B) (1-methyl-1H-imidazol-5-yl)methyl; and
(C) (1-methyl-1H-imidazol-4-yl)methyl;
$R^5$ is H, or —CH$_3$; or
$R^4$ and $R^5$, together with the carbon they are bonded to, form a saturated hydrocarbon ring of 3 atoms;
Y is a group

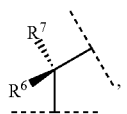

wherein
$R^6$ is H or —CH$_3$;
$R^7$ is H, or —CH$_3$; or
$R^6$ and $R^7$, together with the carbon they are bonded to, form a saturated hydrocarbon ring of 3 or 4 atoms;
Z is selected from:
(A) pyridinyl;
(B) pyrimidinyl;
(C) naphthyridinyl;
(D) pyridazinyl; and
(E) oxadiazolyl;
$R^8$ is selected from:
(A) phenyl optionally substituted with one or two groups selected from:
 (a) —OR$^9$;
 (b) —CH$_2$OR$^9$;
 (c) —C(O)OH;
 (d) —C(O)NR$^9$R$^{10}$;
 (e) —SO$_2$CH$_3$;
 (f) —NHSO$_2$CH$_3$;
 (g) —SO$_2$NR$^9$R$^{10}$;
 (h) —F;
 (i) —NHC(O)CH$_3$;
 (j) —CH$_2$NHSO$_2$CH$_3$;
 (k) —C(O)CH$_3$;
 (l) —Cl;
 (m) —CN;
 (n) —CH$_3$;
 (o) —CH$_2$N(CH$_3$)$_2$; and
 (p) 1-hydroxycyclopropyl;
(B) pyridinyl optionally mono or di substituted with —CH$_3$, —CH$_2$OH, —NH$_2$, —OH, —Cl, —F, —CN, —CF$_3$ or cyclopropyl;
(C) 1H-pyrazolyl optionally mono, di or tri substituted with —CH$_3$ or cyclopropyl;
(D) pyrimidinyl optionally substituted with —CH$_3$;
(E) isoxazolyl optionally substituted with —CH$_3$;
(F) imidazo[1,2-a]pyridinyl optionally substituted with —CH$_3$;
(G) 1H-pyrrolo[2,3-b]pyridinyl;
(H) thiazolyl optionally mono or di substituted with —CH$_3$ or —Cl;
(I) oxadiazolyl optionally substituted with cyclopropyl;
(J) furanyl;
(K) quinolinyl;
(L) 1H-imidazolyl optionally substituted with —CH$_3$;
(M) 1H-triazolyl;
(N) 1H-pyrrolyl optionally substituted with —CH$_3$;
(O) oxazolyl;
(P) 2-oxo-2H-pyridin-1-yl; and
(Q) 1H-indolyl;
$R^9$ is H or —CH$_3$;
$R^{10}$ is H or —CH$_3$;
or a pharmaceutically acceptable salt thereof.

3. A compound of formula I according to claim 1, wherein:
$R^1$ is selected from —CN, —OCF$_3$, —Br, —Cl or —CF$_3$;
$R^2$ is —Cl or —CF$_3$;
$R^3$ is —F or —H;
X is a group

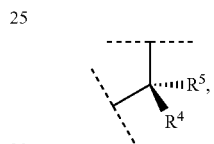

wherein
$R^4$ is selected from:
(A) —CH$_3$;
(B) —CH$_2$OH;
(C) —CH(OH)CH$_3$;
(D) (1-methyl-1H-imidazol-5-yl)methyl; and
(E) (1-methyl-1H-imidazol-4-yl)methyl;
$R^5$ is H or —CH$_3$; or
$R^4$ and $R^5$, together with the carbon they are bonded to, form a saturated hydrocarbon ring of 3 atoms;
Y is a group

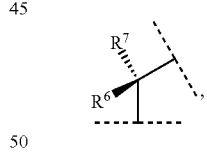

wherein
$R^6$ is —CH$_3$;
$R^7$ is H or —CH$_3$; or
$R^6$ and $R^7$, together with the carbon they are bonded to, form a saturated hydrocarbon ring of 3 or 4 atoms;
Z is selected from:

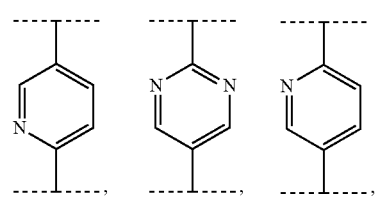

-continued

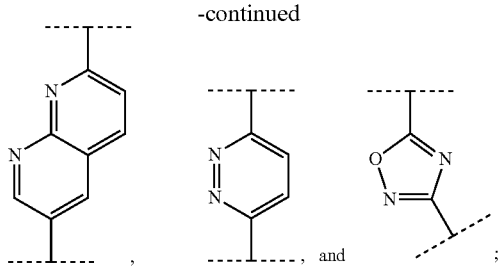

R⁸ is selected from:
(A) phenyl substituted with one group selected from:
   (a) —OH;
   (b) —CH₂OR⁹;
   (c) —C(O)OH;
   (d) —C(O)NR⁹R¹⁰;
   (e) —SO₂CH₃;
   (f) —NHSO₂CH₃;
   (g) —SO₂NH₂;
   (h) —F;
   (i) —NHC(O)CH₃;
   (j) —CH₂NHSO₂CH₃; and
   (k) —C(O)CH₃;
(B) pyridinyl optionally substituted with —CH₃, —CH₂OH, —NH₂, —OH, —F; —CN or cyclopropyl;
(C) 1H-pyrazol-4-yl optionally mono, di or tri substituted with —CH₃ or cyclopropyl;
(D) pyrimidin-5-yl optionally substituted with —CH₃;
(E) isoxazol-4-yl optionally substituted with —CH₃;
(F) 2-imidazo[1,2-a]pyridin-6-yl optionally substituted with —CH₃;
(G) 1H-pyrrolo[2,3-b]pyridin-5-yl;
(H) 1H-pyrazol-3-yl;
(I) thiazol-5-yl optionally substituted with —CH₃;
(J) thiazol-4-yl;
(K) 2-cyclopropyl-1,3,4-oxadiazol-5-yl;
(L) furan-3-yl;
(M) quinolin-3-yl;
(N) 1H-imidazol-2-yl optionally substituted with —CH₃;
(O) 1-methyl-1H-imidazol-5-yl;
(P) 1H-imidazolyl; and
(Q) 1H-1,2,4-triazolyl;
R⁹ is H or —CH₃;
R¹⁰ is H or —CH₃;
or a pharmaceutically acceptable salt thereof.

4. A compound of formula I according to claim 1, wherein:
R¹ is selected from —CN, —OCF₃ or —Br;
R² is —Cl or —CF₃;
R³ is —F or H;
X is a group

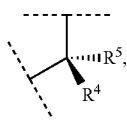

wherein
R⁴ is selected from:
(A) —CH₃;
(B) —CH₂OH; and
(C) —CH(OH)CH₃;

R⁵ is H; or
R⁴ and R⁵, together with the carbon they are bonded to, form a saturated hydrocarbon ring of 3 atoms;
Y is a group

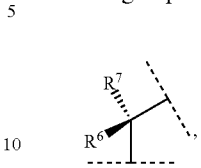

wherein
R⁶ is —CH₃;
R⁷ is H; or
R⁶ and R⁷, together with the carbon they are bonded to, form a saturated hydrocarbon ring of 3 or 4 atoms;
Z is selected from:

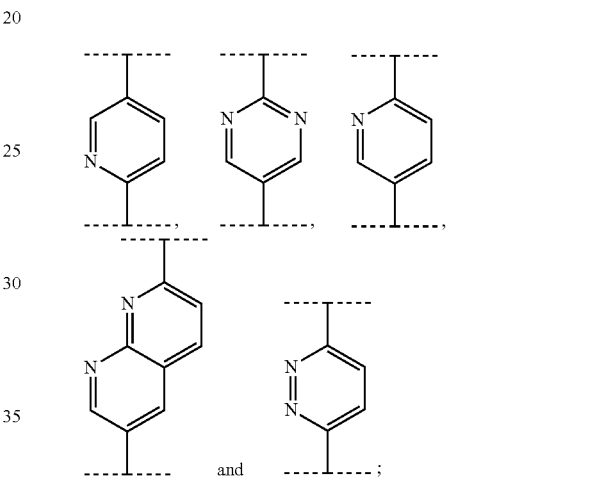

R⁸ is selected from:
(A) phenyl substituted with one group selected from:
   (a) —OH;
   (b) —CH₂OH;
   (c) —C(O)OH;
   (d) —C(O)NR⁹R¹⁰;
   (e) —SO₂CH₃;
   (f) —NHSO₂CH₃; and
   (g) —SO₂NH₂;
(B) pyridinyl optionally substituted with —CH₃, —CH₂OH, —NH₂, —OH, —Cl, or —F;
(C) 1H-pyrazol-4-yl optionally mono, di or tri substituted with —CH₃ or cyclopropyl;
(D) 2-methyl-pyrimidin-5-yl;
(E) isoxazol-4-yl;
(F) imidazo[1,2-a]pyridin-6-yl; and
(G) 1H-pyrrolo[2,3-b]pyridin-5-yl;
R⁹ is H or —CH₃;
R¹⁰ is H or —CH₃;
or a pharmaceutically acceptable salt thereof.

5. A compound of formula I according to claim 1, wherein:
R¹ is selected from —CN and —OCF₃;
R² is —Cl;
R³ is —F;

X is a group

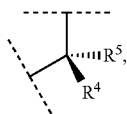

wherein $R^4$ is —CH$_3$ or —CH(OH)CH$_3$;

$R^5$ is H; or $R^4$ and $R^5$, together with the carbon they are bonded to, form a saturated hydrocarbon ring of 3 atoms;

Y is a group

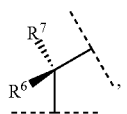

wherein $R^6$ is —CH$_3$;

$R^7$ is H; or $R^6$ and $R^7$, together with the carbon they are bonded to, form a saturated hydrocarbon ring of 3 or 4 atoms;

Z is selected from:

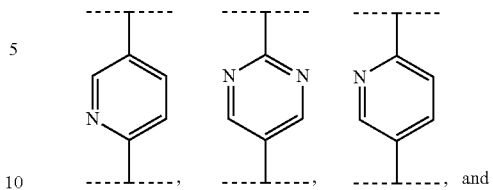

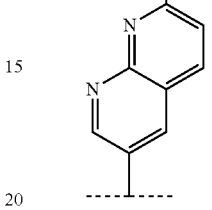

$R^8$ is selected from:
(A) phenyl substituted with one group selected from:
   (a) —OH; and
   (b) —CH$_2$OH;
(B) pyridin-3-yl substituted in the 6-position with —CH$_3$ or —CH$_2$OH; and
(C) 1H-pyrazol-4-yl optionally mono or disubstituted with —CH$_3$;

or a pharmaceutically acceptable salt thereof.

6. A compound selected from the compounds in the following Table 1:

TABLE 1

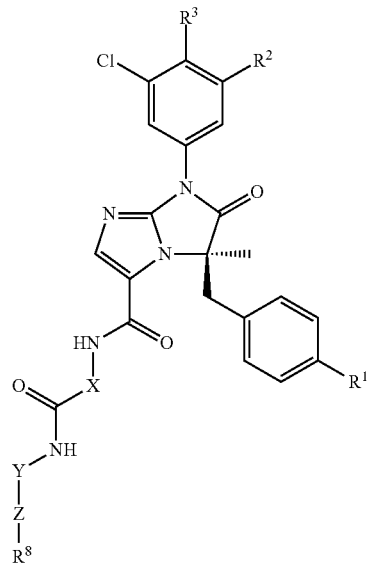

| Compound | R$^1$ | R$^2$ | R$^3$ | X | Y | Z | R$^8$ |
|---|---|---|---|---|---|---|---|
| 1 | CN | Cl | F | | | | |

TABLE 1-continued
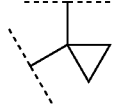
| Compound | R¹ | R² | R³ | X | Y | Z | R⁸ |
|---|---|---|---|---|---|---|---|
| 2 | CN | Cl | F | 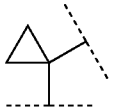 | 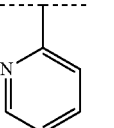 | 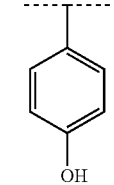 | 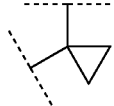 |
| 3 | CN | Cl | F | 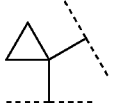 | 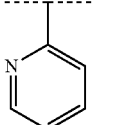 | 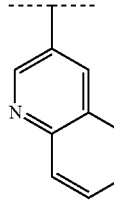 | 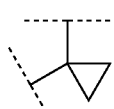 |
| 4 | OCF₃ | Cl | F |  | 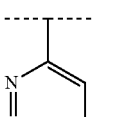 | 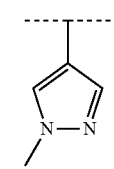 | 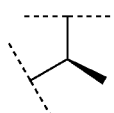 |
| 5 | CN | Cl | F |  | 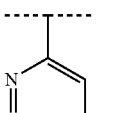 | 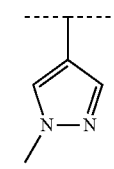 | 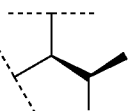 |
| 6 | CN | Cl | F | 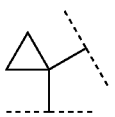 | 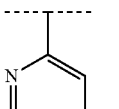 | 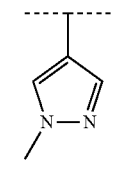 | |

TABLE 1-continued

| Compound | R¹ | R² | R³ | X | Y | Z | R⁸ |
|---|---|---|---|---|---|---|---|
| 7 | OCF₃ | Cl | F | CH(OH)CH(CH₃)- | 1,1-cyclopropyl | pyridazine-3,6-diyl | 1-methyl-1H-pyrazol-4-yl |
| 8 | OCF₃ | Cl | F | 1,1-cyclopropyl | 1,1-cyclopropyl | pyridine-2,5-diyl | 1-methyl-1H-pyrazol-4-yl |
| 9 | CN | Cl | H | 1,1-cyclopropyl | 1,1-cyclopropyl | pyridine-2,6-diyl | 1H-pyrazol-3-yl |
| 10 | CN | Cl | F | 1,1-cyclopropyl | 1,8-naphthyridine-2,6-diyl | pyridine-2,5-diyl | 1H-pyrazol-4-yl |
| 11 | CN | Cl | F | 1,1-cyclopropyl | 1,1-cyclopropyl | pyridine-2,5-diyl | 1H-pyrazol-4-yl |

TABLE 1-continued

| Compound | R¹ | R² | R³ | X | Y | Z | R⁸ |
|---|---|---|---|---|---|---|---|
| 12 | OCF₃ | Cl | F | cyclopropyl | cyclopropyl | pyridine | pyrazole |
| 13 | CN | Cl | F | cyclopropyl | cyclopropyl | pyridine | 5-cyclopropyl-1-methyl-pyrazole |
| 14 | CN | Cl | F | cyclopropyl | cyclopropyl | pyridine | 3-cyclopropyl-1-methyl-pyrazole |
| 15 | CN | Cl | F | cyclopropyl | cyclopropyl | pyridazine | 3-cyclopropyl-1-methyl-pyrazole |
| 16 | CN | Cl | F | cyclopropyl | cyclopropyl | pyridine | imidazo[1,2-a]pyridine |

TABLE 1-continued
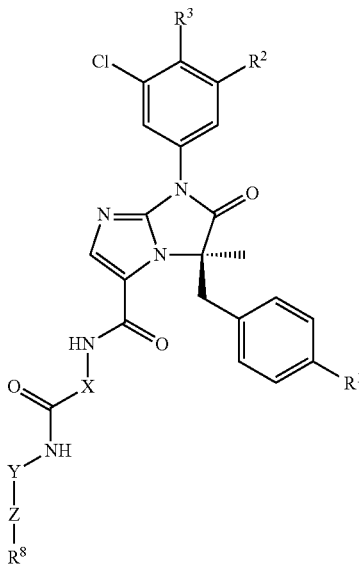
| Compound | R¹ | R² | R³ | X | Y | Z | R⁸ |
|---|---|---|---|---|---|---|---|
| 17 | OCF₃ | Cl | F | 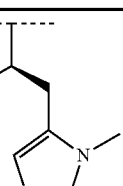 | 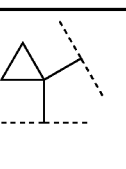 | 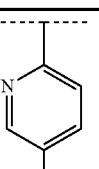 | 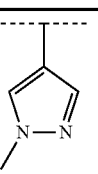 |
| 18 | CN | Cl | F | 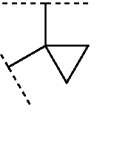 | 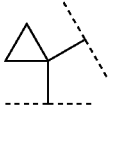 | 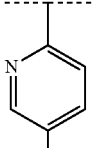 | 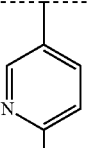 |
| 19 | CN | Cl | F |  | 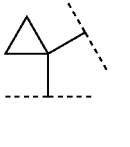 | 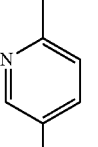 | 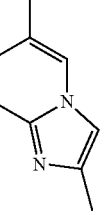 |
| 20 | OCF₃ | Cl | F | 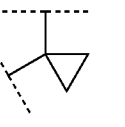 | 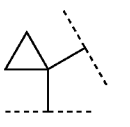 | 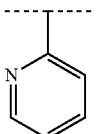 | 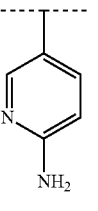 |
| 21 | CN | Cl | F | 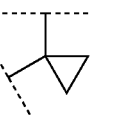 | 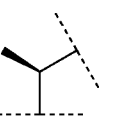 | 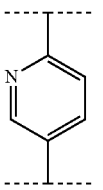 | 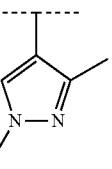 |

TABLE 1-continued
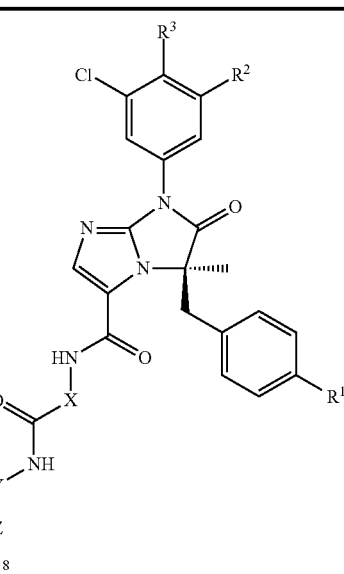
| Compound | R¹ | R² | R³ | X | Y | Z | R⁸ |
|---|---|---|---|---|---|---|---|
| 22 | CN | Cl | H | 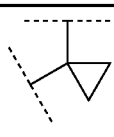 | 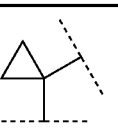 | 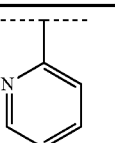 | 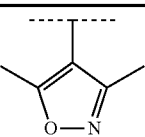 |
| 23 | CN | Cl | F | 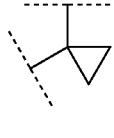 | 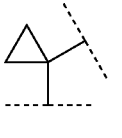 | 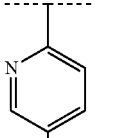 | 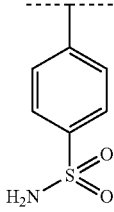 |
| 24 | OCF₃ | Cl | H | 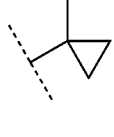 | 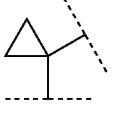 | 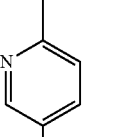 | 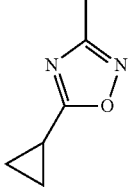 |
| 25 | CN | Cl | F | 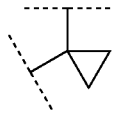 | 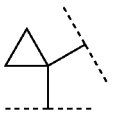 | 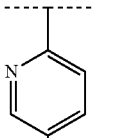 | 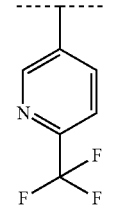 |
| 26 | CF₃ | Cl | H | 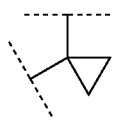 | 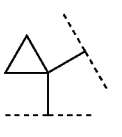 | 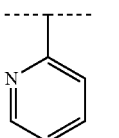 | 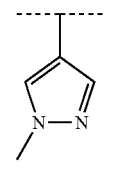 |

TABLE 1-continued

| Compound | R¹ | R² | R³ | X | Y | Z | R⁸ |
|---|---|---|---|---|---|---|---|
| 27 | CN | Cl | F | cyclopropane-1,1-diyl | cyclopropane-1,1-diyl | pyridine-2,5-diyl | 2-methylpyrimidine-5-yl |
| 28 | OCF₃ | Cl | F | CH(CH₃) | cyclopropane-1,1-diyl | pyridine-2,5-diyl | 1-methyl-1H-pyrazol-4-yl |
| 29 | CN | Cl | F | cyclopropane-1,1-diyl | cyclopropane-1,1-diyl | pyridazine-3,6-diyl | 6-(hydroxymethyl)pyridin-3-yl |
| 30 | CN | Cl | F | CH(CH₃)CH(OH) | CH(CH₃) | pyridine-2,5-diyl | 6-methylpyridin-3-yl |
| 31 | CN | Cl | F | cyclopropane-1,1-diyl | cyclopropane-1,1-diyl | pyrimidine-2,5-diyl | 1-methyl-1H-pyrazol-4-yl |

TABLE 1-continued

| Compound | R¹ | R² | R³ | X | Y | Z | R⁸ |
|---|---|---|---|---|---|---|---|
| 32 | CN | Cl | F | spiro-cyclopropyl | spiro-cyclopropyl | pyrimidine-2,5-diyl | 4-(hydroxymethyl)phenyl |
| 33 | CN | Cl | F | spiro-cyclopropyl | spiro-cyclopropyl | pyrimidine-2,5-diyl | 1H-pyrazol-4-yl |
| 34 | CN | Cl | F | spiro-cyclopropyl | spiro-cyclopropyl | pyrimidine-2,5-diyl | 4-hydroxyphenyl |
| 35 | CN | Cl | F | spiro-cyclopropyl | spiro-cyclopropyl | pyridazine-3,6-diyl | 1-methyl-1H-pyrazol-4-yl |
| 36 | CN | Cl | F | spiro-cyclopropyl | spiro-cyclopropyl | pyridazine-3,6-diyl | 4-fluorophenyl |

TABLE 1-continued
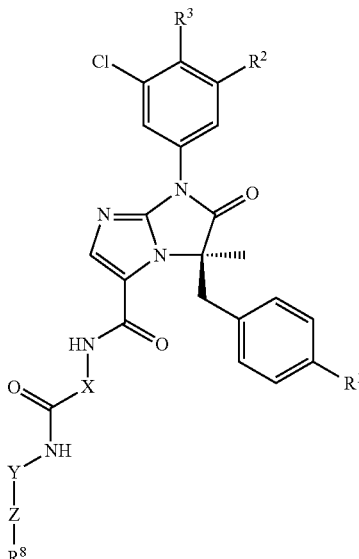
| Compound | R¹ | R² | R³ | X | Y | Z | R⁸ |
|---|---|---|---|---|---|---|---|
| 37 | CN | Cl | F | 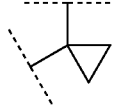 | 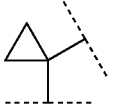 | 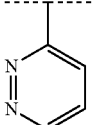 | 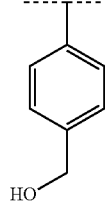 |
| 38 | CN | Cl | F | 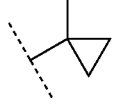 | 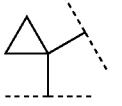 | 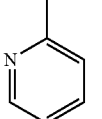 | 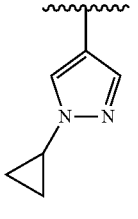 |
| 39 | OCF₃ | Cl | F | 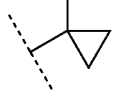 | 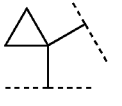 | 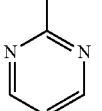 | 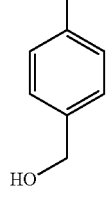 |
| 40 | OCF₃ | Cl | F | 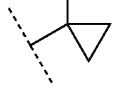 | 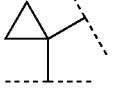 | 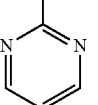 | 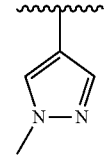 |

TABLE 1-continued

| Compound | R¹ | R² | R³ | X | Y | Z | R⁸ |
|---|---|---|---|---|---|---|---|
| 41 | OCF₃ | Cl | F | cyclopropyl | cyclopropyl | pyridine | pyridine-CH₂OH |
| 42 | OCF₃ | Cl | F | cyclopropyl | cyclopropyl | pyridazine | pyrazole |
| 43 | CN | Cl | F | cyclopropyl | cyclopropyl | pyridine | pyridine-CH₂OH |
| 44 | CN | Cl | F | CH(CH₃) | cyclopropyl | pyridazine | pyrazole |
| 45 | CN | Cl | F | CH(CH₃)CH(OH) | cyclopropyl | pyridazine | pyrazole |

TABLE 1-continued
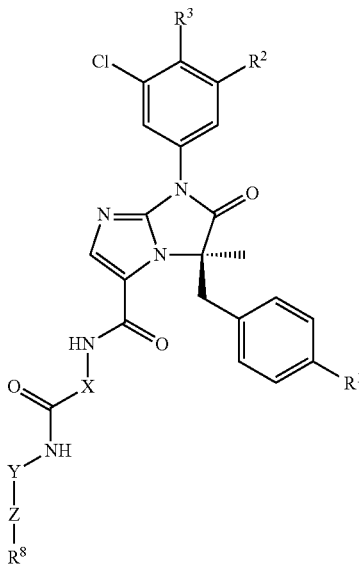
| Compound | R¹ | R² | R³ | X | Y | Z | R⁸ |
|---|---|---|---|---|---|---|---|
| 46 | OCF$_3$ | Cl | F | 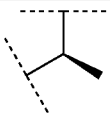 | 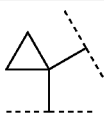 | 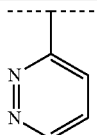 | 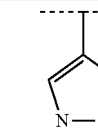 |
| 47 | OCF$_3$ | Cl | F | 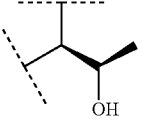 | 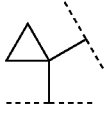 | 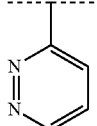 | 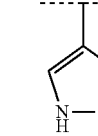 |
| 48 | OCF$_3$ | Cl | F | 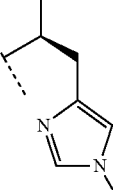 | 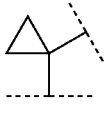 | 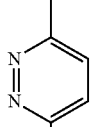 | 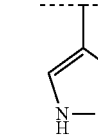 |
| 49 | OCF$_3$ | Cl | F | 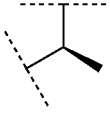 | 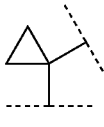 | 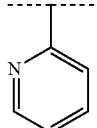 | 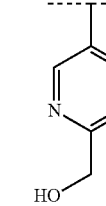 |
| 50 | CN | Cl | F | 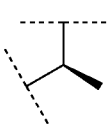 |  | 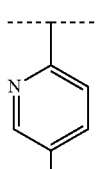 | 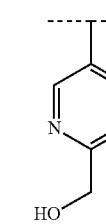 |

TABLE 1-continued

| Compound | R¹ | R² | R³ | X | Y | Z | R⁸ |
|---|---|---|---|---|---|---|---|
| 51 | CN | CF₃ | H | cyclopropyl | cyclopropyl | pyridine | 1-methylpyrazol-4-yl |
| 52 | CN | Cl | H | cyclopropyl | cyclopropyl | pyridine | 3-carboxyphenyl |
| 53 | CN | Cl | H | cyclopropyl | cyclopropyl | pyridine | 3-acetylphenyl |
| 54 | CN | Cl | H | cyclopropyl | cyclopropyl | pyridine | 2-methylpyridin-4-yl |
| 55 | CN | Cl | H | cyclopropyl | cyclopropyl | pyridine | 2-fluoropyridin-3-yl |

TABLE 1-continued

| Compound | R¹ | R² | R³ | X | Y | Z | R⁸ |
|---|---|---|---|---|---|---|---|
| 56 | CN | Cl | H | cyclopropyl | cyclopropyl | pyridine | 3-(N,N-dimethylcarbamoyl)phenyl |
| 57 | CN | Cl | H | cyclopropyl | cyclopropyl | pyridine | 4-methylpyridin-3-yl |
| 58 | CN | Cl | H | cyclopropyl | cyclopropyl | pyridine | 6-fluoropyridin-3-yl |
| 59 | CN | Cl | H | cyclopropyl | cyclopropyl | pyridine | 3-(N-methylcarbamoyl)phenyl |
| 60 | CN | Cl | H | cyclopropyl | cyclopropyl | pyridine | 3,5-dimethyl-1H-pyrazol-4-yl |

TABLE 1-continued

| Compound | R¹ | R² | R³ | X | Y | Z | R⁸ |
|---|---|---|---|---|---|---|---|
| 61 | CN | Cl | H | cyclopropyl | cyclopropyl | pyridin-2,5-diyl | 6-chloropyridin-3-yl |
| 62 | CN | Cl | H | cyclopropyl | cyclopropyl | pyridin-2,5-diyl | 6-methylpyridin-3-yl |
| 63 | CN | Cl | H | cyclopropyl | cyclopropyl | pyridin-2,5-diyl | 5-fluoropyridin-3-yl |
| 64 | CN | Cl | F | cyclopropyl | CH(CH₃) | pyridin-2,5-diyl | 1H-pyrazol-4-yl |
| 65 | CN | Cl | F | cyclopropyl | CH(CH₃) | pyridin-2,5-diyl | 6-(hydroxymethyl)pyridin-3-yl |

TABLE 1-continued

| Compound | R¹ | R² | R³ | X | Y | Z | R⁸ |
|---|---|---|---|---|---|---|---|
| 66 | CN | Cl | H | 1,1-cyclopropyl | 1,1-cyclopropyl | pyridin-2,5-diyl | 3-carbamoylphenyl |
| 67 | CN | Cl | H | 1,1-cyclopropyl | 1,1-cyclopropyl | pyridin-2,5-diyl | furan-3-yl |
| 68 | CN | Cl | F | 1,1-cyclopropyl | 1,1-cyclopropyl | pyridin-2,5-diyl | pyridin-4-yl |
| 69 | CN | Cl | F | 1,1-cyclopropyl | 1,1-cyclopropyl | pyridin-2,5-diyl | phenyl |
| 70 | CN | Cl | F | 1,1-cyclopropyl | 1,1-cyclopropyl | pyridin-2,5-diyl | 3-carbamoylphenyl |

TABLE 1-continued

| Compound | R¹ | R² | R³ | X | Y | Z | R⁸ |
|---|---|---|---|---|---|---|---|
| 71 | CN | Cl | H | cyclopropane-1,1-diyl | cyclopropane-1,1-diyl | pyridine-2,5-diyl | 5-cyanopyridin-3-yl |
| 72 | CN | Cl | F | cyclopropane-1,1-diyl | cyclopropane-1,1-diyl | pyridine-2,5-diyl | 4-carbamoylphenyl |
| 73 | CN | Cl | F | cyclopropane-1,1-diyl | cyclopropane-1,1-diyl | pyridine-2,5-diyl | 6-cyclopropylpyridin-3-yl |
| 74 | CN | Cl | F | cyclopropane-1,1-diyl | cyclopropane-1,1-diyl | pyridine-2,5-diyl | 6-cyanopyridin-3-yl |

TABLE 1-continued

| Compound | R¹ | R² | R³ | X | Y | Z | R⁸ |
|---|---|---|---|---|---|---|---|
| 75 | Br | Cl | H | cyclopropyl | cyclopropyl | pyridine (2,5) | 1-methylpyrazol-4-yl |
| 76 | Cl | Cl | H | cyclopropyl | cyclopropyl | pyridine (2,5) | 1-methylpyrazol-4-yl |
| 77 | CN | Cl | F | cyclopropyl | cyclopropyl | oxazole | 1-methylpyrazol-4-yl |
| 78 | CN | Cl | F | CH(CH₃) | cyclopropyl | pyrimidine (2,5) | 6-(hydroxymethyl)pyridin-3-yl |
| 79 | CN | Cl | H | cyclopropyl | cyclopropyl | pyridine (2,5) | 1H-imidazol-2-yl |

TABLE 1-continued

| Compound | R¹ | R² | R³ | X | Y | Z | R⁸ |
|---|---|---|---|---|---|---|---|
| 80 | CN | Cl | H | cyclopropyl | cyclopropyl | pyridine | 1-methylimidazol-2-yl |
| 81 | CN | Cl | H | cyclopropyl | cyclopropyl | pyridine | 1,2,4-triazol-1-yl |
| 82 | CN | Cl | H | cyclopropyl | cyclopropyl | pyridine | pyrazol-1-yl |
| 83 | CN | Cl | H | cyclopropyl | cyclopropyl | pyridine | imidazol-1-yl |
| 84 | CN | Cl | H | cyclopropyl | cyclopropyl | pyridine | 1-methylimidazol-5-yl |

TABLE 1-continued

| Compound | R¹ | R² | R³ | X | Y | Z | R⁸ |
|---|---|---|---|---|---|---|---|
| 85 | CN | Cl | F | 1,1-cyclopropyl | 1,1-cyclopropyl | pyridin-2,5-diyl | 2-chlorothiazol-5-yl |
| 86 | OCF₃ | Cl | F | 1,1-cyclopropyl | 1,1-cyclopropyl | pyridin-2,5-diyl | 2-oxopyridin-1-yl |
| 87 | CN | Cl | F | isopropyl (CHMe) | 1,1-cyclopropyl | pyridin-2,5-diyl | 4-(hydroxymethyl)phenyl |
| 88 | CN | Cl | F | isopropyl (CHMe) | 1,1-cyclopropyl | pyridin-2,5-diyl | 1-methylpyrazol-4-yl |
| 89 | OCF₃ | Cl | F | 1,1-cyclopropyl | 1,1-cyclopropyl | pyridin-3,6-diyl | 6-(hydroxymethyl)pyridin-3-yl |

TABLE 1-continued
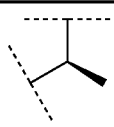
| Compound | R¹ | R² | R³ | X | Y | Z | R⁸ |
|---|---|---|---|---|---|---|---|
| 90 | CN | Cl | F | 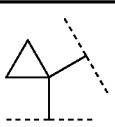 | 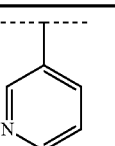 | 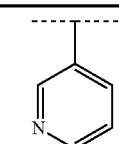 | 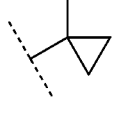 |
| 91 | CN | Cl | H | 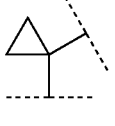 | 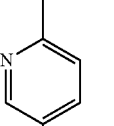 | 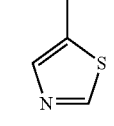 | 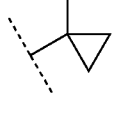 |
| 92 | CN | Cl | H | 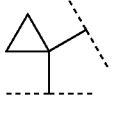 | 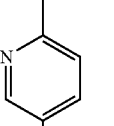 | 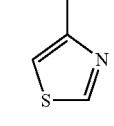 | 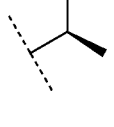 |
| 93 | CN | Cl | F | 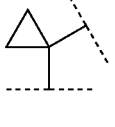 | 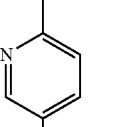 | 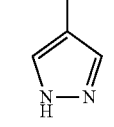 | 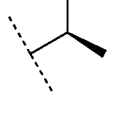 |
| 94 | CN | Cl | F | 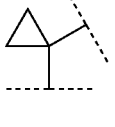 | 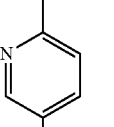 | 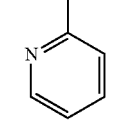 | |

TABLE 1-continued

| Compound | R¹ | R² | R³ | X | Y | Z | R⁸ |
|---|---|---|---|---|---|---|---|
| 95 | CN | Cl | F | isopropyl | cyclopropyl | pyridinyl | 4-methylthiazol-5-yl |
| 96 | CN | Cl | F | isopropyl | cyclopropyl | pyridinyl | 6-(hydroxymethyl)pyridin-3-yl |
| 97 | OCF₃ | Cl | H | isopropyl | cyclopropyl | pyridinyl | 3-cyclopropyl-1,2,4-oxadiazol-5-yl |
| 98 | CN | Cl | H | isopropyl | cyclopropyl | pyridinyl | 5-cyclopropyl-1,3,4-oxadiazol-2-yl |
| 99 | OCF₃ | Cl | F | isopropyl | cyclopropyl | pyridinyl | 1H-pyrazol-3-yl |

TABLE 1-continued
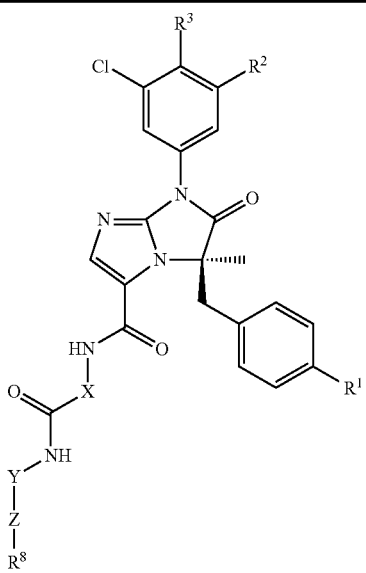
| Compound | R¹ | R² | R³ | X | Y | Z | R⁸ |
|---|---|---|---|---|---|---|---|
| 100 | CN | Cl | F | | | | |
| 101 | CN | Cl | F | | | | |
| 102 | CN | Cl | F | | | | |
| 103 | OCF₃ | Cl | H | | | | |
| 104 | OCF₃ | Cl | F | | | | |

TABLE 1-continued

| Compound | R¹ | R² | R³ | X | Y | Z | R⁸ |
|---|---|---|---|---|---|---|---|
| 105 | CN | Cl | F | CH(CH₃) | cyclopropyl | pyridine-2,5-diyl | 2-oxo-1,2-dihydropyridin-5-yl |
| 106 | CN | Cl | F | CH(CH₃) | cyclopropyl | pyridazine-3,6-diyl | 4-(hydroxymethyl)phenyl |
| 107 | CN | Cl | F | CH(CH₃) | cyclopropyl | pyridine-2,5-diyl | 1-methyl-1H-pyrazol-4-yl |
| 108 | OCF₃ | Cl | F | cyclopropyl | cyclopropyl | pyridine-2,5-diyl | 2-oxo-1,2-dihydropyridin-5-yl |
| 109 | CN | Cl | F | cyclopropyl | cyclopropyl | pyrimidine-2,5-diyl | 6-(hydroxymethyl)pyridin-3-yl |

TABLE 1-continued

| Compound | R¹ | R² | R³ | X | Y | Z | R⁸ |
|---|---|---|---|---|---|---|---|
| 110 | OCF₃ | Cl | F | cyclopropyl | cyclopropyl | pyrimidine | 6-(hydroxymethyl)pyridin-3-yl |
| 111 | CN | Cl | F | cyclopropyl | cyclopropyl | pyrimidine | 1,3-dimethyl-1H-pyrazol-4-yl |
| 112 | CN | Cl | F | cyclopropyl | cyclopropyl | pyrimidine | 6-methylpyridin-3-yl |
| 113 | CN | Cl | F | cyclopropyl | spiro[3.3]cyclobutyl-cyclopropyl | pyridine | 1H-pyrazol-4-yl |
| 114 | CN | Cl | F | cyclopropyl | cyclopropyl | pyrimidine | 4-(methoxymethyl)phenyl |

TABLE 1-continued
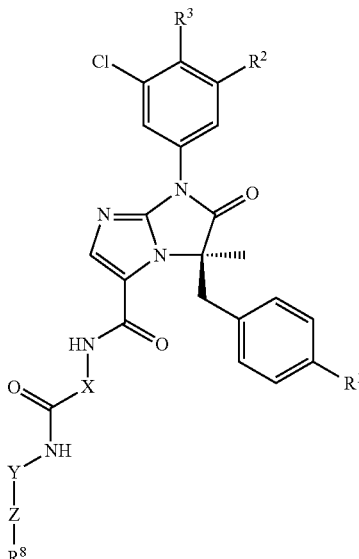
| Compound | R¹ | R² | R³ | X | Y | Z | R⁸ |
|---|---|---|---|---|---|---|---|
| 115 | CN | Cl | F | 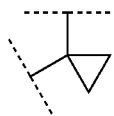 | 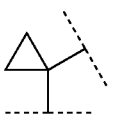 | 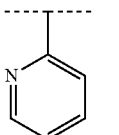 | 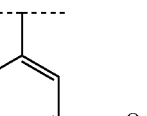 |
| 116 | OCF₃ | Cl | F | 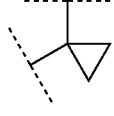 | 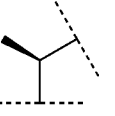 | 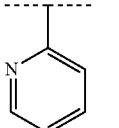 | 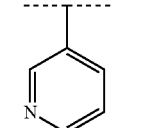 |
| 117 | CN | Cl | F | 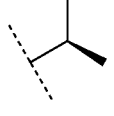 | 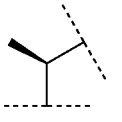 | 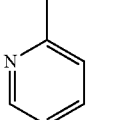 | 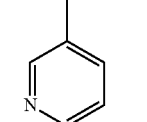 |
| 118 | OCF₃ | Cl | F | 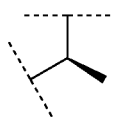 | 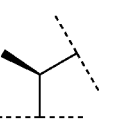 | 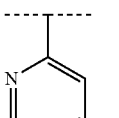 | 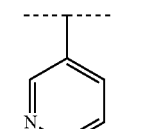 |

TABLE 1-continued

| Compound | R¹ | R² | R³ | X | Y | Z | R⁸ |
|---|---|---|---|---|---|---|---|
| 119 | CN | Cl | F | CH(OH)CH(CH₃) | CH(CH₃) | pyridine-2,5-diyl | 6-(hydroxymethyl)pyridin-3-yl |
| 120 | OCF₃ | Cl | F | CH(OH)CH(CH₃) | CH(CH₃) | pyridine-2,5-diyl | 6-(hydroxymethyl)pyridin-3-yl |
| 121 | CN | Cl | F | CH(OH)CH(CH₃) | CH(CH₃) | pyridine-2,5-diyl | 1,3-dimethyl-1H-pyrazol-4-yl |
| 122 | CN | Cl | F | 1,1-cyclopropyl | CH(CH₃) | pyridine-2,5-diyl | 1,3-dimethyl-1H-pyrazol-4-yl |
| 123 | CN | Cl | F | 1,1-cyclopropyl | 1,1-cyclopropyl | pyridine-2,5-diyl | 1,3-dimethyl-1H-pyrazol-4-yl |

TABLE 1-continued

| Compound | R¹ | R² | R³ | X | Y | Z | R⁸ |
|---|---|---|---|---|---|---|---|
| 124 | CN | Cl | H | 1,1-cyclopropyl | cyclopropyl | pyridin-2,4-diyl | 1H-pyrazol-4-yl |
| 125 | OCF₃ | Cl | F | CH(OH)CH(CH₃) | cyclopropyl | pyrimidin-2,5-diyl | 6-(hydroxymethyl)pyridin-3-yl |
| 126 | CN | Cl | H | 1,1-cyclopropyl | cyclopropyl | pyridin-2,5-diyl | 3-((dimethylamino)methyl)phenyl |
| 127 | CN | Cl | H | 1,1-cyclopropyl | spiro-cyclopropyl | pyridin-2,5-diyl | isoxazol-4-yl |
| 128 | CN | Cl | H | 1,1-cyclopropyl | cyclopropyl | pyridin-2,5-diyl | 1-methyl-1H-pyrrol-2-yl |

TABLE 1-continued

| Compound | R¹ | R² | R³ | X | Y | Z | R⁸ |
|---|---|---|---|---|---|---|---|
| 129 | CN | Cl | H | cyclopropyl | cyclopropyl | pyridin-2,5-diyl | 1H-pyrazol-4-yl |
| 130 | CN | Cl | H | cyclopropyl | cyclopropyl | pyridin-2,5-diyl | 4-chlorophenyl |
| 131 | CN | Cl | H | cyclopropyl | cyclopropyl | pyridin-2,5-diyl | 4-carbamoylphenyl |
| 132 | CN | Cl | H | cyclopropyl | cyclopropyl | pyridin-2,5-diyl | 4-sulfamoylphenyl |

TABLE 1-continued
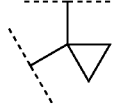
| Compound | R¹ | R² | R³ | X | Y | Z | R⁸ |
|---|---|---|---|---|---|---|---|
| 133 | CN | Cl | H | 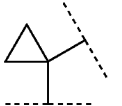 | 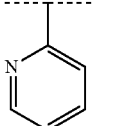 | 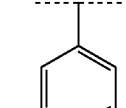 |  |
| 134 | CN | Cl | H | 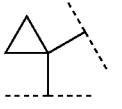 | 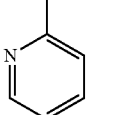 | 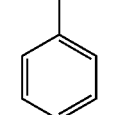 | 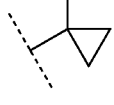 |
| 135 | CN | Cl | H | 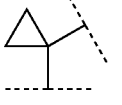 | 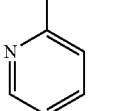 | 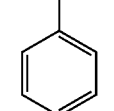 | 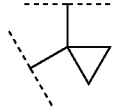 |
| 136 | CN | Cl | H | 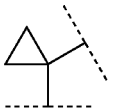 | 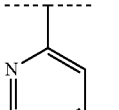 | 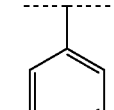 |  |

TABLE 1-continued

| Compound | R¹ | R² | R³ | X | Y | Z | R⁸ |
|---|---|---|---|---|---|---|---|
| 137 | CN | Cl | H | cyclopropyl | cyclopropyl | pyridine | 4-cyanophenyl |
| 138 | CN | Cl | H | cyclopropyl | cyclopropyl | pyridine | 3-sulfamoylphenyl |
| 139 | CN | Cl | H | cyclopropyl | cyclopropyl | pyridine | 4-acetamidophenyl |
| 140 | CN | Cl | H | cyclopropyl | cyclopropyl | pyridine | 3-methanesulfonamidophenyl |

TABLE 1-continued

| Compound | R¹ | R² | R³ | X | Y | Z | R⁸ |
|---|---|---|---|---|---|---|---|
| 141 | CN | Cl | H | cyclopropyl-gem-disubstituted | cyclopropyl-gem-disubstituted | pyridin-2,5-diyl | 3-(methylsulfonyl)phenyl |
| 142 | CN | Cl | H | cyclopropyl-gem-disubstituted | cyclopropyl-gem-disubstituted | pyridin-2,5-diyl | 3-hydroxyphenyl |
| 143 | CN | Cl | H | cyclopropyl-gem-disubstituted | cyclopropyl-gem-disubstituted | pyridin-2,5-diyl | 3-(hydroxymethyl)phenyl |
| 144 | CN | Cl | H | cyclopropyl-gem-disubstituted | cyclopropyl-gem-disubstituted | pyridin-2,5-diyl | 3-(methylsulfonamidomethyl)phenyl |
| 145 | CN | Cl | F | CH(OH)CH(CH₃) | cyclopropyl-gem-disubstituted | pyrimidin-2,5-diyl | 1,3-dimethylpyrazol-4-yl |

TABLE 1-continued
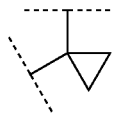
| Compound | R¹ | R² | R³ | X | Y | Z | R⁸ |
|---|---|---|---|---|---|---|---|
| 146 | CN | Cl | H | 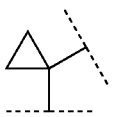 | 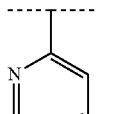 | 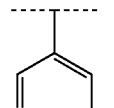 | 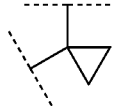 |
| 147 | CN | Cl | H | 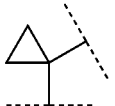 | 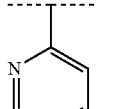 | 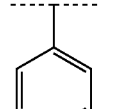 | 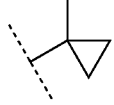 |
| 148 | CN | Cl | H | 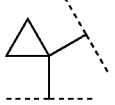 | 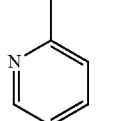 | 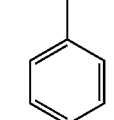 | 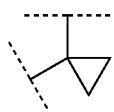 |
| 149 | CN | Cl | H |  | 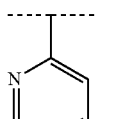 | 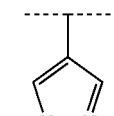 | 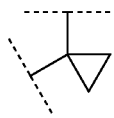 |
| 150 | OCF₃ | Cl | F | 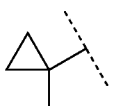 | 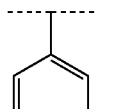 | 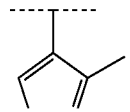 | |

TABLE 1-continued
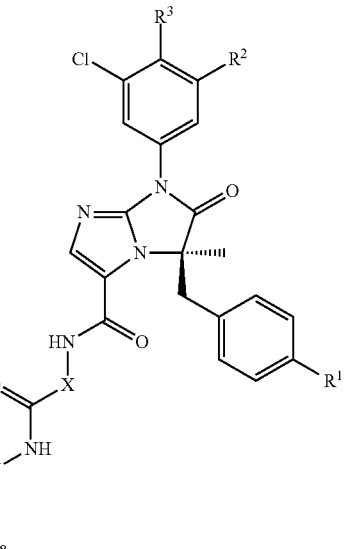
| Compound | R¹ | R² | R³ | X | Y | Z | R⁸ |
|---|---|---|---|---|---|---|---|
| 151 | CN | Cl | F | 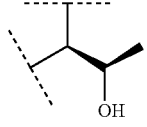 | 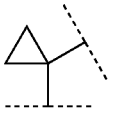 | 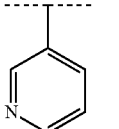 | 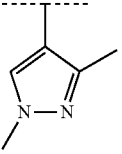 |
| 152 | CN | Cl | F | 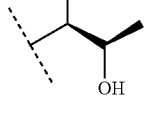 | 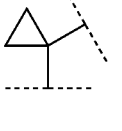 | 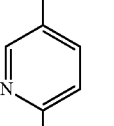 | 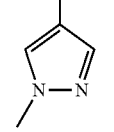 |
| 153 | OCF₃ | Cl | F | 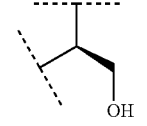 | 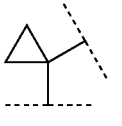 | 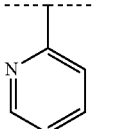 | 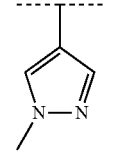 |
| 154 | CN | Cl | F | 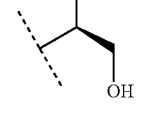 | 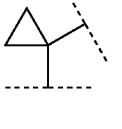 | 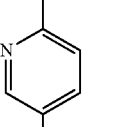 | 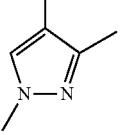 |
| 155 | CN | Cl | F | 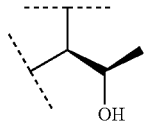 | 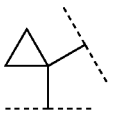 | 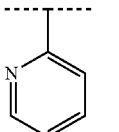 | 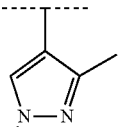 |

TABLE 1-continued

| Compound | R¹ | R² | R³ | X | Y | Z | R⁸ |
|---|---|---|---|---|---|---|---|
| 156 | CN | Cl | F | cyclopropyl | cyclopropyl | pyridine (2,5) | 1,3-dimethylpyrazol-4-yl |
| 157 | CN | Cl | F | cyclopropyl | cyclopropyl | pyridine (2,5) | 3,5-dimethyl-1H-pyrazol-4-yl |
| 158 | CN | Cl | F | cyclopropyl | cyclopropyl | pyridine (2,5) | 4-(methylsulfonyl)phenyl |
| 159 | CN | Cl | F | CH(OH)CH(CH₃) | cyclopropyl | pyrimidine (2,5) | 1-methylpyrazol-4-yl |

TABLE 1-continued

| Compound | R¹ | R² | R³ | X | Y | Z | R⁸ |
|---|---|---|---|---|---|---|---|
| and 160 | CN | Cl | F | (1,1-cyclopropyl) | (isopropyl, stereo) | (pyridin-2,5-diyl) | (6-(hydroxymethyl)pyridin-3-yl) | or a pharmaceutically acceptable salt thereof.

7. A compound according to claim 6, selected from compounds 1, 2, 4-8, 10-16, 18, 20, 21, 23, 27, 28, 30-35, 37-47, 49-52, 54, 56, 58, 60-62, 64-66, 68-70, 72, 75, 78, 87-90, 93, 96, 100, 101, 103-106, 108-112, 115-121, 123, 125, 127, 129, 131-136, 138, 141-143, 145, 146 and 149-160 or a pharmaceutically acceptable salt thereof.

8. A pharmaceutical composition comprising a compound in accordance with claim 1, or a pharmaceutically acceptable salt thereof, and at least one pharmaceutically acceptable carrier or adjuvant.

9. A method for treating adult respiratory distress syndrome, shock, oxygen toxicity, multiple organ injury syndrome secondary to septicemia, multiple organ injury syndrome secondary to trauma, reperfusion injury of tissue due to cardiopulmonary bypass, myocardial infarction, acute glomerulonephritis, vasculitis, reactive arthritis, dermatosis with acute inflammatory components, stroke, thermal injury, hemodialysis, leukapheresis, necrotizing enterocolitis or granulocyte transfusion associated syndrome, psoriasis, organ/tissue transplant rejection, graft vs. host reaction, Raynaud's syndrome, autoimmune thyroiditis, dermatitis, multiple sclerosis, rheumatoid arthritis, insulin-dependent diabetes mellitus, uveitis, inflammatory bowel disease, Crohn's disease, ulcerative colitis, systemic lupus erythematosus or asthma in a patient comprising administering to said patient a therapeutically effective amount of a compound according to claim 1, or a pharmaceutically acceptable salt thereof.

10. A method according to claim 9, where the condition to be treated is multiple sclerosis.

11. A method according to claim 9, where the condition to be treated is psoriasis.

12. A method according to claim 9, where the condition to be treated is organ/tissue transplant rejection.

13. A method according to claim 9, where the condition to be treated is graft vs. host reaction.

14. A method according to claim 9, where the condition to be treated is systemic lupus erythematosus.

15. The compound 4 according to claim 6, or a pharmaceutically acceptable salt thereof.

16. The compound 8 according to claim 6, or a pharmaceutically acceptable salt thereof.

17. The compound 18 according to claim 6, or a pharmaceutically acceptable salt thereof.

18. The compound 38 according to claim 6, or a pharmaceutically acceptable salt thereof.

19. The compound 40 according to claim 6, or a pharmaceutically acceptable salt thereof.

20. The compound 41 according to claim 6, or a pharmaceutically acceptable salt thereof.

21. The compound 43 according to claim 6, or a pharmaceutically acceptable salt thereof.

22. The compound 78 according to claim 6, or a pharmaceutically acceptable salt thereof.

23. The compound 87 according to claim 6, or a pharmaceutically acceptable salt thereof.

24. The compound 88 according to claim 6, or a pharmaceutically acceptable salt thereof.

25. The compound 89 according to claim 6, or a pharmaceutically acceptable salt thereof.

26. The compound 93 according to claim 6, or a pharmaceutically acceptable salt thereof.

27. The compound 110 according to claim 6, or a pharmaceutically acceptable salt thereof.

28. The compound 111 according to claim 6, or a pharmaceutically acceptable salt thereof.

29. The compound 116 according to claim 6, or a pharmaceutically acceptable salt thereof.

30. The compound 118 according to claim 6, or a pharmaceutically acceptable salt thereof.

31. The compound 121 according to claim 6, or a pharmaceutically acceptable salt thereof.

32. The compound 125 according to claim 6, or a pharmaceutically acceptable salt thereof.

33. The compound 145 according to claim 6, or a pharmaceutically acceptable salt thereof.

34. The compound 156 according to claim 6, or a pharmaceutically acceptable salt thereof.

* * * * *